US009464273B2

United States Patent
Reijo Pera et al.

(10) Patent No.: US 9,464,273 B2
(45) Date of Patent: *Oct. 11, 2016

(54) PLURIPOTENT CELL LINES AND METHODS OF USE THEREOF

(71) Applicants: Parkinson's Institute, Sunnyvale, CA (US); The Board of Trustees of the Leland Stanford Junior University, Palo Alto, CA (US)

(72) Inventors: Renee Ann Reijo Pera, Los Altos, CA (US); J. William Langston, Los Altos Hills, CA (US); Birgitt Schule, Menlo Park, CA (US); Theodore D. Palmer, Stanford, CA (US); Blake Byers, San Francisco, CA (US); Ha Nam Nguyen, San Francisco, CA (US); James Anthony Byrne, Palo Alto, CA (US); Branden John Cord, East Palo Alto, CA (US)

(73) Assignees: PARKINSON'S INSTITUTE, Sunnyvale, CA (US); THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/098,890

(22) Filed: Dec. 6, 2013

(65) Prior Publication Data
US 2014/0356455 A1    Dec. 4, 2014

Related U.S. Application Data

(63) Continuation of application No. 12/459,019, filed on Jun. 24, 2009, now Pat. No. 8,669,048.

(60) Provisional application No. 61/075,323, filed on Jun. 24, 2008, provisional application No. 61/084,249, filed on Jul. 28, 2008.

(51) Int. Cl.
| C12N 5/0793 | (2010.01) |
| G01N 33/50 | (2006.01) |
| C12Q 1/68 | (2006.01) |
| A61K 35/12 | (2015.01) |

(52) U.S. Cl.
CPC ........... C12N 5/0619 (2013.01); C12Q 1/6883 (2013.01); G01N 33/5023 (2013.01); G01N 33/5058 (2013.01); A61K 35/12 (2013.01); C12N 2500/25 (2013.01); C12N 2500/46 (2013.01); C12N 2501/01 (2013.01); C12N 2501/115 (2013.01); C12N 2501/119 (2013.01); C12N 2501/13 (2013.01); C12N 2501/15 (2013.01); C12N 2501/392 (2013.01); C12N 2501/41 (2013.01); C12N 2501/602 (2013.01); C12N 2501/603 (2013.01); C12N 2501/604 (2013.01); C12N 2503/02 (2013.01); C12N 2506/1307 (2013.01); C12N 2506/45 (2013.01); C12Q 2600/136 (2013.01); G01N 2333/47 (2013.01)

(58) Field of Classification Search
CPC .............. C12N 5/0619; C12Q 1/6883; G01N 33/5023

See application file for complete search history.

(56) References Cited

U.S. PATENT DOCUMENTS

| 5,654,183 | A | 8/1997 | Anderson et al. |
| 5,766,948 | A | 6/1998 | Gage et al. |
| 5,776,683 | A | 7/1998 | Smith et al. |
| 5,807,680 | A | 9/1998 | Sutcliffe et al. |
| 5,843,780 | A | 12/1998 | Thomson |
| 5,849,553 | A | 12/1998 | Anderson et al. |
| 5,851,832 | A | 12/1998 | Weiss et al. |
| 5,968,829 | A | 10/1999 | Carpenter |
| 6,040,180 | A | 3/2000 | Johe |
| 7,029,913 | B2 | 4/2006 | Thomson |
| 8,669,048 | B2 | 3/2014 | Pera et al. |
| 2005/0081257 | A1 | 4/2005 | Eggan et al. |
| 2006/0101527 | A1 | 5/2006 | Pallanck et al. |
| 2006/0141519 | A1 | 6/2006 | Millonig et al. |
| 2008/0280362 | A1 | 11/2008 | Jaenisch et al. |
| 2009/0047263 | A1 | 2/2009 | Yamanaka et al. |
| 2009/0191159 | A1 | 7/2009 | Sakurada et al. |
| 2010/0021437 | A1 | 1/2010 | Isacson et al. |
| 2010/0167286 | A1 | 7/2010 | Pera et al. |

FOREIGN PATENT DOCUMENTS

| WO | WO 98/50526 A1 | 11/1998 | |
| WO | WO 99/01159 A1 | 1/1999 | |
| WO | WO2007/069666 | * 6/2007 | ............ C12N 15/09 |
| WO | WO 2007/069666 | 6/2007 | |
| WO | WO 2009/006930 A1 | 1/2009 | |
| WO | WO 2009/006997 A1 | 1/2009 | |
| WO | WO 2009/007852 A2 | 1/2009 | |
| WO | WO 2009/007852 A3 | 8/2009 | |

OTHER PUBLICATIONS

Wood-Kaczmar et al. (Trends in Molecular Medicine. 2006; 12(11): 521-528).*

(Continued)

Primary Examiner — Scott Long
(74) Attorney, Agent, or Firm — Wilson Sonsini Goodrich & Rosati

(57) ABSTRACT

Methods of generating cell lines with a sequence variation or copy number variation of a gene of interest, methods of use thereof, and cell lines with a sequence variation or copy number variation of a gene of interest are provided.

21 Claims, 33 Drawing Sheets

(56) References Cited

OTHER PUBLICATIONS

Kaji et al. (Nature, Apr. 9, 2009 [published online Mar. 1, 2009]; 458: 771-776).*

Rovelet-Lecrux et al. (Nature Genetics, Jan. 2006; 38(11): 24-26).*

Adewumi et al. Characterization of human embryonic stem cell lines by the International Stem Cell Initiative. Nature Biotechnology. 2007;25:803-816.

Amir, et al. Rett syndrome is caused by mutations in X-linked MECP2, encoding methyl-CpG-binding protein 2. Nat Genet. Oct. 1999;23(2):185-8.

Andreotti, et al. Chemosensitivity testing of human tumors using a microplate adenosine triphosphate luminescence assay: clinical correlation for cisplatin resistance of ovarian carcinoma. Cancer Res. Nov. 15, 1995;55(22):5276-82.

Aoi et al. Generation of Pluripotent Stem Cells from Adult Mouse Liver and Stomach Cells. Science. Aug. 1, 2008;321(5889):699-702.

Beckers, et al. Application of intracellular ATP determination in lymphocytes for HLA-typing. J Biolumin Chemilumin. Sep. 1986;1(2):47-51.

Bongso, et al. Improved quality of human embryos when co-cultured with human ampullary cells. Hum Reprod. 1989; 4(6): 706-713.

Brooks, et al. Astrocytes as a primary locus for the conversion MPTP into MPP+. J Neural Transm. 1989;76(1):1-12.

Brooks, et al. Paraquat elicited neurobehavioral syndrome caused by dopaminergic neuron loss. Brain Res. Mar. 27, 1999;823(1-2):1-10.

Chamberlain, et al. Induced pluripotent stem (iPS) cells as in vitro models of human neurogenetic disorders. Neurogenetics. Oct. 2008;9(4):227-35.

Chartier-Harlin et al. Alpha-synuclein locus duplication as a cause of familial Parkinson's disease. The Lancet. 2004;364(9440):1167-1169.

Crouch, et al. The use of ATP bioluminescence as a measure of cell proliferation and cytotoxicity. J Immunol Methods. Mar. 15, 1993;160(1):81-8.

Daley, et al. Prospects for stem cell-based therapy. Cell. Feb. 22, 2008;132(4):544-8.

D'Amato, et al., Selectivity of the Parkinsonian Neurotoxin MPTP: Toxic Metabolite MPP+ Binds to Neuromelanin. Science. Feb. 28, 1986;231(4741):987-9.

Deb-Rinker et al. Sequential DNA methylation of the Nanog and Oct-4 upstream regions in human NT2 cells during neuronal differentiation. The Journal of biological chemistry. 2005;(280):6257-6260.

Decipher v5.0. Available at https://decipher.sanger.ac.uk. Accessed Sep. 22, 2010.

Di Monte, et al. Comparative studies on the mechanisms of paraquat and 1-methyl-4-phenylpyridine (MPP+) cytotoxicity. Biochem Biophys Res Commun. May 29, 1986;137(1):303-9.

Di Monte, et al. Production and disposition of 1-methyl-4-phenylpyridinium in primary cultures of mouse astrocytes. Glia. 1992;5(1):48-55.

Dorsey, et al. Projected number of people with Parkinson disease in the most populous nations, 2005 through 2030. Neurology. Jan. 30, 2007;68(5):384-6.

Evans, et al. Early onset seizures and Rett-like features associated with mutations in CDKL5. Eur J Hum Genet. Oct. 2005;13(10):1113-20.

Farrer. Genetics of Parkinson disease: paradigm shifts and future prospects. Nat Rev Genet. Apr. 2006;7(4):306-18.

Filipov, et al. Dopaminergic toxicity of the herbicide atrazine in rat striatal slices. Toxicology. Mar. 22, 2007;232(1-2):68-78.

Formon, et al. Nosology of Parkinson's disease: looking for the way out of a quagmire. Neuron. Aug. 18, 2005;47(4):479-82.

Fuchs et al. Phenotypic variation in a large Swedish pedigree due to SNCA duplication and triplication. Neurology. 2007;916-922.

Gardner, et al. Culture and transfer of human blastocysts increases implantation rates and reduces the need for multiple embryo transfers. Fertil Steril. Jan. 1998;69(1):84-8.

Hanna, et al. Treatment of sickle cell anemia mouse model with iPS cells generated from autologous skin. Science. Dec. 21, 2007;318(5858):1920-3.

Hazell, et al., 1-Methyl-4-phenyl-1,2,3,6-tetrahydropyridine (MPTP) Decreases Glutamate Uptake in Cultured Astrocytes. J Neurochem. May 1997;68(5):2216-9.

Ibáñez et al. Causal relation between alpha-synuclein gene duplication and familial Parkinson's disease. The Lancet. 2004;364(9440):1169-1171.

International search report dated Feb. 17, 2010 for PCT Application No. US2009/003783.

Joutel et al. Notch 3 mutations in CADASIL, a hereditary adult-onset condition causing stroke and dementia. Nature. 1996;383:707-710.

Kaelin. von Hippel-Lindau disease. Annual Review of Pathology. 2007;2:145-173.

Kehrer-Sawatzki. What a difference a copy number variation makes. BioEssays. 2007;29:311-313.

Kopin. Features of the dopaminergic neurotoxin MPTP. Ann N Y Acad Sci. May 11, 1992;648:96-104.

Langer. New methods of drug delivery. Science. 1990; 249:1527-1533.

Langston. The Parkinson's Complex: Parkinsonism is just the tip of the iceberg. Annals of Neurology. Apr. 2006; 59(4):591-596.

Litvan, et al. The etiopathogenesis of Parkinson disease and suggestions for future research. Part I. J Neuropathol Exp Neurol. Apr. 2007;66(4):251-7.

Litvan, et al. The etiopathogenesis of Parkinson disease and suggestions for future research. Part II. J Neuropathol Exp Neurol. May 2007;66(5):329-36.

Lowry et al. Generation of human induced pluripotent stem cells from dermal fibroblasts. Proc Natl Acad Sci U S A. Feb. 26, 2008;105(8):2883-8.

Lupski. Genome structural variation and sporadic disease traits. Nat Genet. Sep. 2006;38(9):974-6.

Marchetto, et al. Induced pluripotent stem cells (iPSCs) and neurological disease modeling: progress and promises. Hum Mol Genet. Oct. 15, 2011;20(R2):R109-15. doi: 10.1093/hmg/ddr336. Epub Aug. 9, 2011.

Masaki et al. Tendency of pluripotential marker gene expression in colonies derived from human neonatal fibroblasts induced by the human iPS cell method. Stem Cell Research. 2008. doi:10.1016/j.scr.2008.01.001.

McNaught, et al., Effects of Isoquinoline Derivatives Structurally Related to 1-methyl-4-phenyl-1,2,3,6-tetrahydropyridine (MPTP) on Mitochondrial Respiration. Biochem Pharmacol. Jun. 14, 1996;51(11):1503-11.

Muhle, et al. The genetics of autism. Pediatrics. May 2004;113(5):e472-86.

Murry et al. Differentiation of embryonic stem cells to clinically relevant populations: lessons from embryonic development. Cell. 2008;132(4):661-680.

Nakagawa et al. Generation of induced pluripotent stem cells without Myc from mouse and human fibroblasts. Nat Biotechnol. 2008;26:101-106.

Nicklas, et al., MPTP, MPP+ and Mitochondrial Function, Life Sci. 1987; 40:72129.

Nilaver, et al. Delivery of herpesvirus and adenovirus to nude rat intracerebral tumors after osmotic blood-brain barrier disruption. Proc Natl Acad Sci U S A. Oct. 10, 1995;92(21):9829-33.

Notice of allowance dated Oct. 10, 2013 for U.S. Appl. No. 12/459,019.

Notice of allowance dated Dec. 17, 2013 for U.S. Appl. No. 12/459,019.

O'Brien, et al. Investigation of the Alamar Blue (resazurin) fluorescent dye for the assessment of mammalian cell cytotoxicity. Eur J Biochem. Sep. 2000;267(17):5421-6.

Office action dated May 24, 2013 for U.S. Appl. No. 12/459,019.
Office action dated Jun. 27, 2011 for U.S. Appl. No. 12/459,019.
Office action dated Sep. 22, 2011 for U.S. Appl. No. 12/459,019.

(56) References Cited

OTHER PUBLICATIONS

Office action dated Nov. 16, 2012 for U.S. Appl. No. 12/459,019.
Outeiro, et al. Sirtuin 2 inhibitors rescue alpha-synuclein-mediated toxicity in models of Parkinson's disease. Science. Jul. 27, 2007;317(5837):516-9.
Park et al. Disease-Specific Induced Pluripotent Stem Cells. Cell. 2008;134(5):877-886.
Park et al. Reprogramming of human somatic cells to pluripotency with defined factors. Nature. Jan. 10, 2008;451(7175):141-6.
Park, et al. Efficient generation of dopamine neurons from human embryonic stem cells. Methods Mol Biol. 2007;407:311-22.
PDGene. Available at www.pdgene.org. Accessed Sep. 22, 2010.
Pellecchia, et al. The diverse phenotype and genotype of pantothenate kinase-associated neurodegeneration. Neurology. 2005; 64 (10): 1810-2.
Peng, et al. Nigrostriatal dopaminergic neurodegeneration in the weaver mouse is mediated via neuroinflammation and alleviated by minocycline administration. J Neurosci. Nov. 8, 2006;26(45):11644-51.
Redon et al. Global variation in copy number in the human genome. Nature. 2006;23:444-454.
Reubinoff, et al. Embryonic stem cell lines from human blastocysts: somatic differentiation in vitro. Nat Biotechnol. Apr. 2000;18(4):399-404.
Riss, et al.. Use of multiple assay endpoints to investigate effects of incubation time, dose of toxin and plating density in cell-based cytotoxicity assays. Assay Drug Dev. Technol. 2004; 2:51-62.
Rubin, L. Stem cells and drug discovery: the beginning of a new era? Cell. Feb. 22, 2008;132(4):549-52.
Sebat et al. Strong association of de novo copy number mutations with autism. Science. 2007;316:445-459.
Singleton et al. alpha-Synuclein locus triplication causes Parkinson's disease. Science. 2003;302:841.
Smeyne, et al. Strain-dependent susceptibility to MPTP and MPP(+)-induced parkinsonism is determined by glia. Glia. Apr. 15, 2001;34(2):73-80.
Soldner et al. Parkinson's Disease Patient-Derived Induced Pluripotent Stem Cells Free of Viral Reprogramming Factors. Cell. 2009;136(5):964-977.
Solter, et al. Immunosurgery of mouse blastocyst. Proc Natl Acad Sci U S A. Dec. 1975;72(12):5099-102.
Szatmari et al. Mapping autism risk loci using genetic linkage and chromosomal rearrangements. Nature Genetics. 2007;39(3):319-328.
Tagami, et al. Processes of beta-amyloid and intracellular cytoplasmic domain generation by presenilin/gamma-secretase. Neurodegener Dis. 2008;5(3-4):160-2.
Takahashi et al. Induction of pluripotent stem cells from adult human fibroblasts by defined factors. Cell. Nov. 30, 2007;131(5):861-72.
Takahashi et al. Induction of pluripotent stem cells from mouse embryonic and adult fibroblast cultures by defined factors. Cell. Aug. 25, 2006;126(4):663-76.
Thomas, et al. The Wilson disease gene: spectrum of mutations and their consequences, Nat Genet. 1995; 9(2):210-7.
Thomson et al. Embryonic stem cell lines derived from human blastocysts. Science. Nov. 6, 1998;282(5391):1145-7.
Thomson, et al. Isolation of a primate embryonic stem cell line. Proc Natl Acad Sci U S A. Aug. 15, 1995;92(17):7844-8.
Thomson, et al. Primate embryonic stem cells. Curr. Top. Dev. Biol. 1998; 38:133-165.
Treat, et al. Liposomes in the Therapy of infectious Disease and Cancer, Lopez-Berestein and Fidler (eds.), Liss, New York, pp. pp. 317-327 and 353-365 (1989).
Velculescu, et al. Serial analysis of dream expression. Science. 1995; 270:484-487.
Wernig et al. In vitro reprogramming of fibroblasts into a pluripotent ES-cell-like state. Nature. 2007;448:318-324.
Willard, et al. Breaking the silence in Rett syndrome. Nat Genet. Oct. 1999;23(2):127-8.
Wisniewski, et al.Apolipoprotein E: binding to soluble Alzheimer's beta-amyloid. Biochem Biophys Res Commun. Apr. 30, 1993;192(2):359-65.
Wood-Kaczmar, et al. Understanding the molecular causes of Parkinson's disease. Trends Mol Med. Nov. 2006;12(11):521-8.
Wszolek et al. Rapidly progressive autosomal dominant parkinsonism and dementia with pallido-ponto-nigral degeneration. Annals of Neurology. 1992. 32(3):312-320.
Yan, et al. Directed differentiation of dopaminergic neuronal subtypes from human embryonic stem cells. Stem Cells. Jun.-Jul. 2005;23(6):781-90.
Yu et al. Induced pluripotent stem cell lines derived from human somatic cells. Science. Dec. 21, 2007;318(5858):1917-20.

\* cited by examiner

Figure 2
Fig. 2A
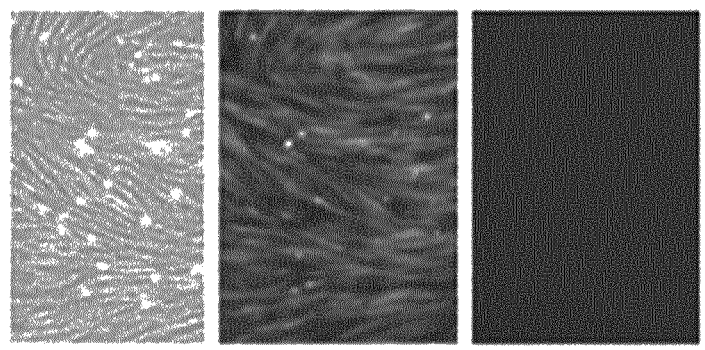
Fig. 2B
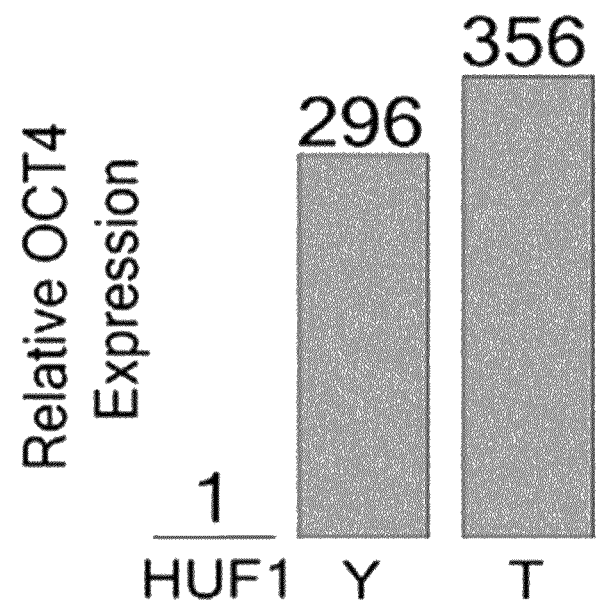
Fig. 2C
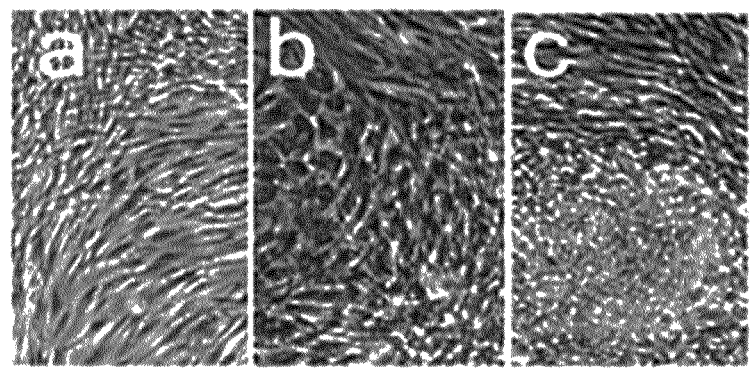

Fig. 4A
HUF1 not transduced with FUGW-UbC-GFP viral supernatant (negative control)
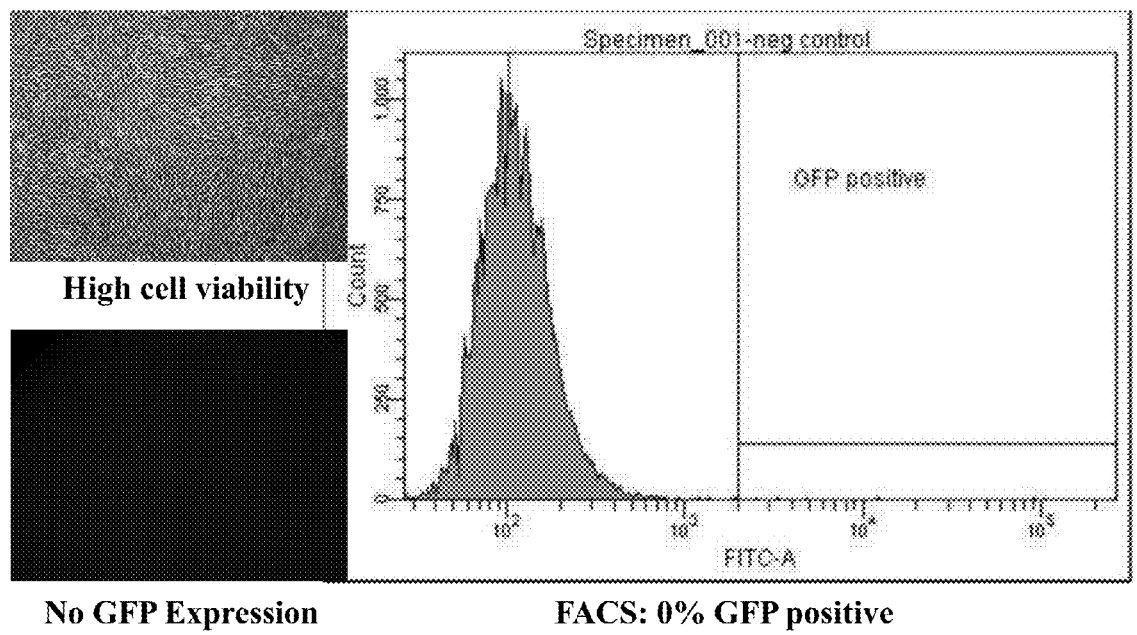
Fig. 4B
HUF1 transduced with 4-fold dilution of fresh FUGW-UbC-GFP viral supernatant
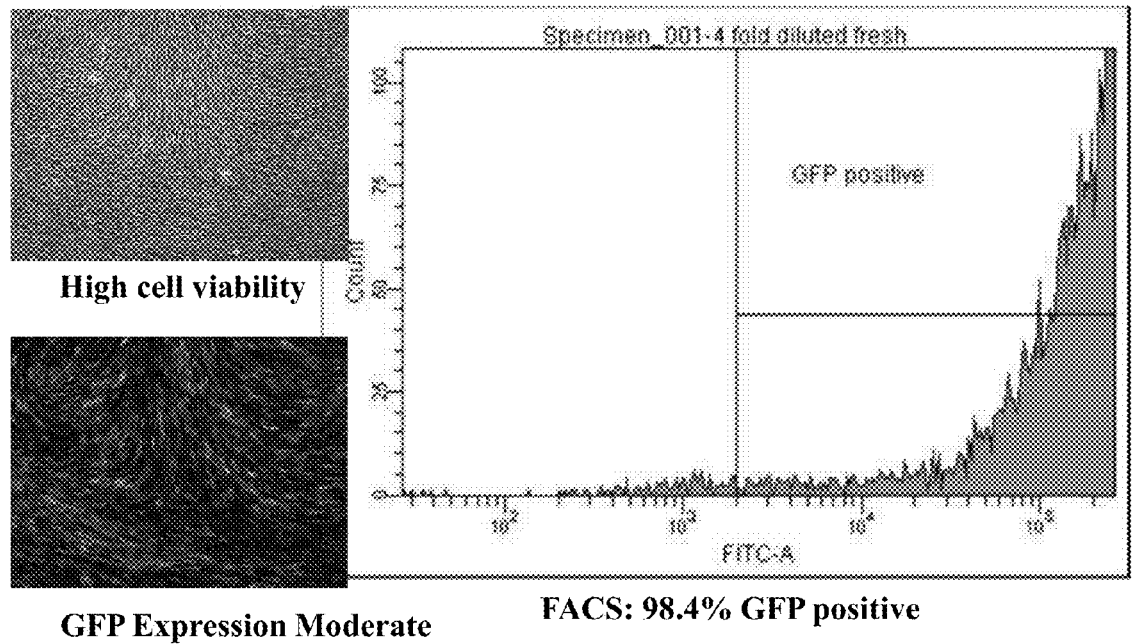
Figure 4

IPS01 (Thomson factors – cMyc/Klf4)

IPS02 (Thomson factors – cMyc/Klf4)

IPS03 (Thomson factors – cMyc/Klf4)

IPS04 (Thomson factors – cMyc/Klf4)

IPS05 (Thomson factors – cMyc/Klf4)

IPS06 (Thomson factors – cMyc/Klf4)

IPS07 (Thomson factors – cMyc/Klf4)

IPS08 (Thomson factors – cMyc/Klf4)

IPS09 (Thomson factors + cMyc/Klf4)

IPS10 (Thomson factors + cMyc/Klf4)

IPS11 (Thomson factors + cMyc/Klf4)

IPS12 (Thomson factors + cMyc/Klf4)

Figure 9
Fig. 9A
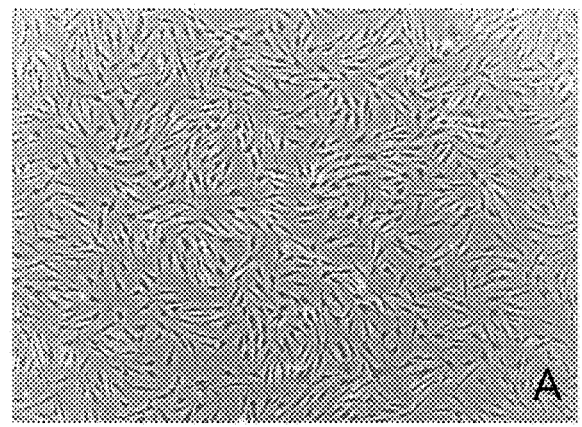
Fig. 9B
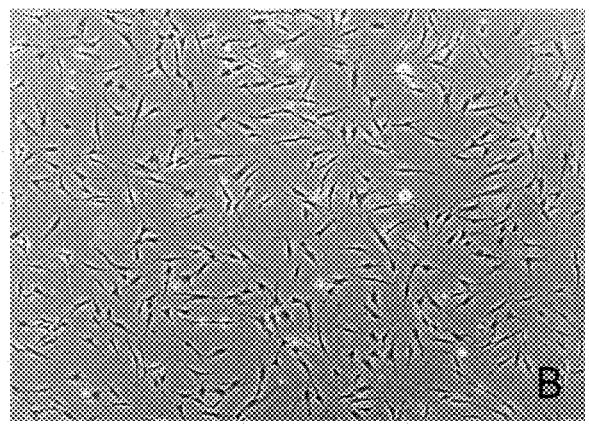

46,XX

Expansion of HUF6-iPS in Matrigel and xCFI1 Feeders

Matrigel xCF1 Feeder

PLURIPOTENT CELL LINES AND METHODS OF USE THEREOF

CROSS-REFERENCE

This application is a Continuation application which claims the benefit of U.S. application Ser. No. 12/459,019, filed Jun. 24, 2009; which claims the benefit of U.S. Provisional Application No. 61/075,323, filed Jun. 24, 2008, and U.S. Provisional Application No. 61/084,249, filed Jul. 28, 2008, which applications are incorporated herein by reference.

BACKGROUND OF THE INVENTION

The examination of the disease progression of complex diseases such as Parkinson's disease is hindered by inaccessibility of neurons and largely limited to use of postmortem samples. Primary cells from postmortem brain samples have short life-spans in vitro and the disease itself reduces in number one cell type of interest—the midbrain dopamine neuron. To date, it has been virtually impossible to use disease-affected neural tissues to screen for therapeutic agents useful for disease modification, predict disease progression and phenotype, and elucidate complex disease mechanisms. A model that replicates the fundamental features of the disease at the cellular level is needed.

Complex diseases such as Parkinson's disease, as well as many others, can involve genetic variations such as mutations and/or copy number variation (CNV) or can be idiopathic/sporadic. Induced pluripotent stem cells (iPSCs), developed from patients presenting with genetic and complex diseases, further differentiated into specific cell types, known to be affected in the natural progression of disease, will provide hertofore unavailable cellular tools for identification of disease mechanisms, therapeutic agent screening, and disease diagnosis.

SUMMARY OF THE INVENTION

The invention described herein provides methods and compositions for generating induced pluripotent stem cells (iPSCs) specific to a disease of interest, wherein the iPSCs are further differentiated to adopt a cell fate involved in the disease. The differentiated iPSCs can be used for screening, diagnostics, and the like. In a preferred embodiment, patient-specific iPSCs related to Parkinson's disease or Parkinson's-like disease are generated. The patients can have a genetic form of the disease or a sporadic form of the disease. The Parkinson's disease and Parkinson's disease-related iPSCs are further differentiated into cell types, such as dopaminergic neurons, involved in the progression disease. The differentiated iPSCs, relevant to Parkinson's disease and Parkinson's-like disease, are a valuable cellular model for elucidating basic disease mechanisms, screening for therapeutics, and for use in diagnostic, prognostic, and theranostic applications.

In one aspect the invention described herein provides a method of producing dopaminergic cells from a patient having a diagnosis of Parkinson's disease or Parkinson's-like disease, the method comprising obtaining fibroblasts from the patient, dedifferentiating the fibroblasts into pluripotent stem cells, and differentiating the stem cells towards a dopaminergic cell fate. In one aspect the invention described herein provides a method of producing dopaminergic cells from a patient having a diagnosis of Parkinson's disease or Parkinson's-like disease, the method comprising obtaining fibroblasts from the patient, dedifferentiating the fibroblasts into pluripotent stem cells, and differentiating the stem cells towards a dopaminergic cell fate. In one embodiment the fibroblasts are dermal fibroblasts. In another embodiment the stem cells are differentiated towards a midbrain dopaminergic cell fate. In particular embodiments, the dedifferentiating of the fibroblasts induces pluripotency.

In some embodiments, the patient carries a genetic variation or mutation known to be associated with Parkinson's disease or Parkinson's-like disease. In other embodiments the genetic variation of interest is a copy number variation of a gene of interest. In specific embodiments, the cell line has three copies of the gene of interest. The genetic variation or mutation can be a deletion, an insertion, a complex multi-state variant, a deletion, a substitution, a transition, a transversion, or a duplication, of one or more nucleotides in the gene of interest. In exemplary embodiments, the gene of interest is selected from PARK1 (SNCA or α-synuclein), PARK2 (Parkin), PARK5 (UCHL1), PARK6 (PINK1), PARK7 (DJ-1), PARK8 (LRRK2), and PARK 11 (GIGFY2). In specific embodiments the gene of interest is PARK1 (SNCA or α-synuclein). In other specific embodiments, the gene of interest is PARK8 (LRRK2). In one embodiment the patient carries a homozygous mutation of LRRK2 and the mutation comprises a G2019S mutation. In some embodiments, the patient has Parkinson's disease. In a specific embodiment the patient has an idiopathic form of Parkinson's disease.

In another aspect the invention described herein provides a method of determining whether an agent is useful in the treatment of Parkinson's disease or Parkinson's-like disease, the method comprising contacting dopaminergic cells produced from induced pluripotent stem cells derived from a patient with Parkinson's disease or Parkinson's-like disease, detecting the presence or absence of a response in the cells, and determining whether the agent is useful in the treatment based on the detected response. In one embodiment, the detected response is a change in cell viability, cellular chemistry, cellular function, mitochondrial function, cell aggregation, cell morphology, cellular protein aggregation, gene expression, cellular secretion, or cellular uptake. In a related embodiment, the agent is selected from a small molecule, a drug, an antibody, a hybrid antibody, an antibody fragment, a siRNA, an antisense RNA, an aptamer, a protein, or a peptide. In a related embodiment, the agent corrects an α-synuclein dysfunction. In specific embodiments, the agent is selected from the group consisting of apomorphine, pyrogallol, 1,4-naphthoquinone, cisplatin, isoproterenol, pyrogallin, cianidanol, sulfasalazine, quinalizarin, benserazide, hexachlorophene, pyrvinium pamoate, dobutamine, methyl-dopa, curcumin, berberine chloride, daidzein, merbromin, norepinephrine, dopamine hydrochloride, carbidopa, ethylnorepinephrine hydrochloride, tannic acid, elaidyphosphocholine, hydroquinone, chlorophyllide Cu complex Na salt, methyldopa, isoproterenol hydrochloride, benserazide hydrochloride, dopamine, dobutamine hydrochloride, thyroid hormone, purpurin, sodium beta-nicotinamide adenine dinucleotide phosphate, lansoprazole, dyclonine hydrochloride, pramoxine hydrochloride, azobenzene, cefamandole sodium, cephaloridine, myricetin, 6,2',3'-trihydroxyflavone, 5,7,3',4',5'-pentahydroxyflavone, 7,3',4',5'-tetrahydroxyflavone, (5,6,7,4'-tetrahydroxyflavone), baicalein, eriodictyol, 7,3',4'-trihydroxyisoflavone, epigallocatechin gallate, quercetin, gossypetin (3,5,7,8,3',4'-hexahydroxyflavone), 2',3'-dihydroxyflavone, 3',4'-dihydroxyflavone, 5,6-dihydroxy-7-methoxyflavone, baicalein-7-methyl ether, 1-dopa, DOPAC, homogentisic acid, 6-hydroxydopamine, epinephrine, 3,4-dihydroxycinnamic acid, 2,3-dihydroxynaphthalene, 3,4-dihydroxybenzoic acid, 3,4,5-trihydroxybenzoic acid, 1,2,3-trihydroxybenzoic acid, gallate (gallic acid), benzoquinone, catechol, rifampicin, rosmarinic acid, baicalin, tanshinones I and II, emodin, procyanidin B4, resveratrol, rutin, fisetin, luteolin, fustin, epicatechin gallate, catechin, alizarin, tannic acid, eriodyctol, carboplatin, purpurogallin-4-carboxylic acid, koparin, 2,3,4-trihydroxy-4'-ethexybenzophenone, baeomycesic acid, hamtoxylin, iriginol hexaaceatate, 4-acetoxyphenol, theaflavin monogallate, theaflavin digallate, stictic acid, purpurogallin, 2,5-dihydroxy-3,4-dimethoxy-4'-ethoxybenzophenone, promethazine hydrochloride, oxidopamine hydrochloride, pyrantel pamoate, elaidylphosphocholine, amphotericin B, gallic acid, fumarprotocetraric acid, theaflavin, haematoxylin pentaacetate, 4-methoxydalbergione, epigallocatechin-3-monogallate, rolitetracycline, 7,3'-dimethoxyflavone, liquiritigenin dimethyl ether, catechin pentaacetate, apigenin, 3,4-dedesmethyl-5-deshydroxy-3'-ethoxyscleroin, derivatives and analogs thereof.

In one embodiment the induced pluripotent stem cells are derived from human fibroblasts. In a related embodiment the induced pluripotent stem cells are produced without the use of a retrovirus or a lentivirus. In a specific embodiment the induced pluripotent stem cells are produced with a method comprising the use of three factors. The three factors can be OCT4, SOX2, and KLF4. In another embodiment, the induced pluripotent stem cells are further differentiated to adopt a midbrain dopaminergic cell fate. In some cases, the induced pluripotent stem cells are differentiated to adopt the cell fate in about 20 days.

In another embodiment, the patient carries a genetic variation or mutation known to be associated with Parkinson's disease or Parkinson's-like disease. In a related embodiment the genetic variation of interest is a copy number variation of a gene of interest. In specific embodiments, the cell line has three copies of the gene of interest. The genetic variation or mutation can be a deletion, an insertion, a complex multi-state variant, a deletion, a substitution, a transition, a transversion, or a duplication, of one or more nucleotides in the gene of interest. In a specific embodiment the gene of interest is selected from PARK1 (SNCA or α-synuclein), PARK2 (Parkin), Park5 (UCHL1), PARK6 (PINK1), PARK7 (DJ-1), PARK8 (LRRK2), and PARK 11 (GIGFY2). In related embodiments the gene of interest is PARK1 (SNCA or α-synuclein). In other related embodiments, the gene of interest is PARK8 (LRRK2). In a specific related embodiment, the patient carries a homozygous mutation of LRRK2. The LRRK2 mutation can comprise a G2019S mutation. In some embodiments the patient has Parkinson's disease. In other embodiments, the patient has an idiopathic form of Parkinson's disease.

In yet another aspect, the invention provides for an induced pluripotent cell line from a patient with Parkinson's disease or Parkinson's-like disease, produced by obtaining fibroblasts from a patient with Parkinson's disease or Parkinson's-like disease carrying a genetic mutation which causes the disease, dedifferentiating the fibroblasts, whereby producing induced pluripotent stem cells, and differentiating the stem cells towards a dopaminergic cell fate, whereby producing an induced pluripotent cell line from a patient with Parkinson's disease or Parkinson's-like disease. In one embodiment, the fibroblasts are dermal fibroblasts. In another embodiment the pluripotent stem cells are differentiated towards a midbrain dopaminergic cell fate. In a related embodiment the patient carries a genetic variation or mutation known to be associated with Parkinson's disease or Parkinson's-like disease. In a specific embodiment, the genetic variation of interest is a copy number variation of a gene of interest. In a related specific embodiment, the cell line has three copies of the gene of interest. In another related embodiment the genetic variation or mutation is a deletion, an insertion, a complex multi-state variant, a deletion, a substitution, a transition, a transversion, or a duplication, of one or more nucleotides in the gene of interest. In one embodiment the gene of interest is selected from PARK1 (SNCA or α-synuclein), PARK2 (Parkin), PARK5 (UCHL1), PARK6 (PINK1), PARK7 (DJ-1), PARK8 (LRRK2), and PARK 11 (GIGFY2). In another embodiment the gene of interest is PARK1 (SNCA or α-synuclein). In a specific embodiment the gene of interest is PARK8 (LRRK2). In a specific related embodiment, the patient carries a homozygous mutation of LRRK2, with a G2019S mutation. In one embodiment the patient has Parkinson's disease. In another embodiment the patient has an idiopathic form of Parkinson's disease. In a related embodiment, the induced pluripotent cell line is produced without the use of a retrovirus or a lentivirus, or produced with a method comprising the use of three factors. The three factors can be OCT4, SOX2, and KLF4. In a related embodiment, the induced pluripotent cell line is differentiated to adopt the cell fate in about 20 days.

In a related aspect the invention provides for a human induced pluripotent cell line from a patient with Parkinson's disease wherein the cell line comprises a genetic variation related to Parkinson's disease. In one embodiment, the variation is triplication of the SNCA gene. In another embodiment, the variation is a homozygous mutation of the LRRK2 gene. In a specific embodiment, the induced pluripotent cell line is produced from fibroblasts of a patient with Parkinson's disease. In another embodiment the induced pluripotent cell line is produced without the use of a retrovirus or a lentivirus or with a method comprising the use of three factors. The three factors can be OCT4, SOX2, and KLF4. In a specific embodiment, the induced pluripotent cell line is further differentiated to adopt a midbrain dopaminergic cell fate. In a related embodiment, the induced pluripotent cell line is differentiated to adopt the cell fate in about 20 days.

In yet another related aspect, the invention provides a human induced pluripotent cell line from a patient with Parkinson's disease, wherein the cell line comprises either a genetic variation comprising a variation in the SNCA gene or the LRRK2 gene.

Methods of generating cell lines with genetic variations of a gene of interest, methods of use thereof, and cell lines with sequence and/or copy number variations of a gene of interest are also provided herein.

In some aspects, the methods include providing cells with sequence variations or multiple copies of the gene of interest, and inducing pluripotency, multipotency or totipotency in the cells to make a cell line with the variation of the gene of interest. The methods may also include identifying a subject with a variation of the gene of interest and obtaining one or more cells from the subject. The subject-derived cells may be fibroblast cells, tumor cells, bone marrow cells, stomach cells, blood cells (such as white blood cells, blood progenitor cells), liver cells, etc. or any convenient or relevant source of cells to be obtained from the subject. The methods of generating cell lines with a copy number variation of a gene of interest may also include inducing differentiation of the cell line. The cell lines may be differentiated into any cell type of interest including endodermal, ectodermal, mesodermal, for example neural, such as neuronal cell lines, epithelial cell lines, cardiac cell lines, etc.

In some aspects, the cell lines and methods of their use include cell lines with a genetic copy number variation that is at least one duplication, for example, two or three multiple copies of a gene. In other aspects, the copy number variation is one or more deletion, insertion, or complex multi-state variant of the gene of interest.

In some aspects, the cell lines and methods of their use include cell lines with a genetic variation that is a mutation of the gene of interest. For example, the mutation may be a deletion, substitution, transition, transversion, or duplication of one or more nucleotides in the gene of interest. In some embodiments, the mutation is a point mutation.

In some aspects, the cell lines and methods of their use include cell lines with a genetic variation that is associated with a disorder, such as a genetic disease.

Methods of screening cell lines with variations of a gene of interest for an agent to treat a disorder or disease are also provided herein. The methods include contacting the agent with a cell line or its progeny made by the methods described herein, observing a change or lack of change in the cells, and correlating a change or lack of change with the ability of the agent to treat the disease. Such changes may be observed, for example, by staining for one or more markers. The methods may further comprise comparing the cell line or its progeny with a cell line or its progeny without the variation in the gene of interest, that is, a normal cell line, or a cell line correlated to the same disorder of interest, but without the variation in the gene of interest present in the first cell line.

Methods of studying the mechanism of a disease of interest are also provided herein. The methods include identifying a molecular determinant of the disorder or disease by contacting a cell line or its progeny made by the methods described herein with an agent or condition which affects a cellular pathway of interest and observing a change or lack of change in the cells.

Methods of treating or preventing disorders are also provided herein. The methods include administering to a subject an agent identified by the screening methods described herein an effective amount to treat or prevent the disorder. Disorders include diseases and susceptibilities, for example, Parkinson's disease, Alzheimer's disease, dementia, an autism spectrum disorder, susceptibility to viral infection, diffuse Lewy body disease or any other Lewy body disorder or synucleinopathy, corticobasal degeneration, encephalitis lethargica, multiple system atrophy, pantothenate kinase-associated neurodegeneration (Hallervorden-Spatz syndrome), progressive supranuclear palsy, vascular Parkinsonism, Wilson disease, hereditary pancreatitis, glomerulonephritis, human systemic lupus erythematosus, paraneoplastic syndrome, frontotemporal dementia with Parkinsonism chromosome 17, Huntington's disease, spinocerebellar ataxias, amytropic lateral sclerosis, Creutzfeld Jakob disease, and other conditions resulting from genetic variations.

DESCRIPTION OF THE DRAWINGS

FIG. 2 illustrates (FIG. 2A) Human fibroblast cells (HUF1 cell line); middle panel shows expression of GFP from the ubiquitin promoter; (FIG. 2B) expression of OCT4 post-infection with a lentivirus:OCT4 cDNA; (FIG. 2C) generation of colonies; (a) no factors, (b) Yamanaka factors with granular colony, (c) Thomson factors with hESC-like colony.

(FIG. 3A) Differentiation involved a multi-step procedure where cells are first neutralized in embryoid body microaggregates and then plated under midbrain induction conditions that include FGF-8 and sonic hedgehog. Further differentiation leads to cultures containing aggregates of NeuN and doublecortin (Dcx) positive neurons (FIG. 3B, FIG. 3C), many of which are tyrosine hydroxlase positive (TH). Nuclei are stained with DAPI. (FIG. 3D) and (FIG. 3E) are magnifications of boxed area in the lower left of panel (FIG. 3C).

FIG. 4 illustrates the expression of GFP in primary human fibroblasts (HUF1 cell line) before (FIG. 4A) and following transduction with FUGW UbC-GFP lentivirus (FIG. 4B).

FIG. 9 illustrates the untransduced fibroblasts used for the generation of the HUF4 (FIG. 9A) and HUF5 lines (FIG. 9B).

(FIG. 33A) Inhibition of fibrillation of .alpha.-synuclein upon incubation with a specific inhibitor, detected by Thioflavin T fluorescein and (FIGS. 33B-C) confirmed by electron microscopy of .alpha.-synuclein fibrils. (FIGS. 33D-E). Diminished Thioflavin S deposits (which label aggregate protein) detected in paraquat-treated mouse brain with Catechol (250 uM), indicative of treatment-induced dissolution of aggregate structure.

INCORPORATION BY REFERENCE

Figure 1:
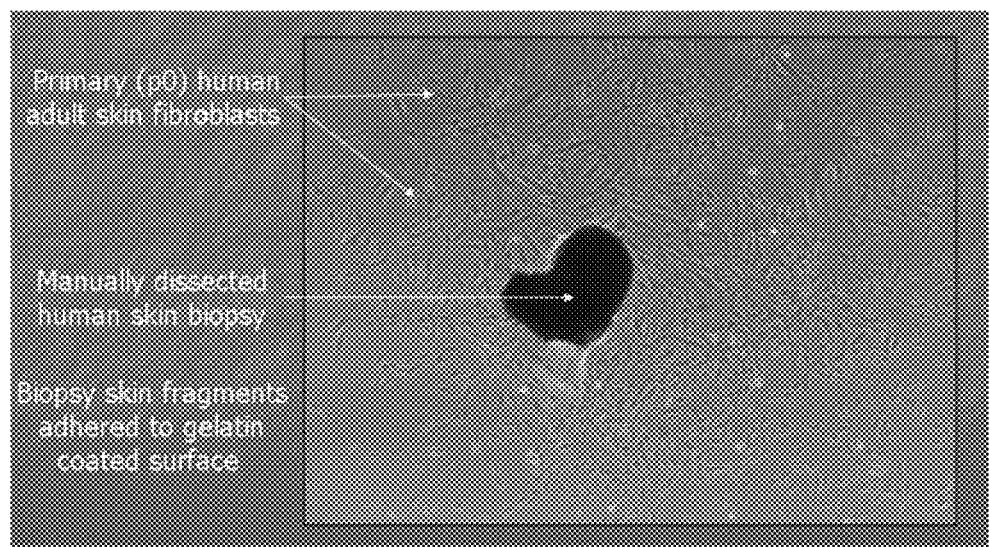
FIG. 1 illustrates the results of derivation of primary human fibroblasts from human subjects.

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Creation of Induced Pluripotent Stem Cell Lines Specific to Diseases and Disorders Overview:

Methods of generating cell lines with genetic variations of a gene of interest, methods of use thereof including differentiation of the cells to a lineage of interest, the use of cell lines in identifying agents to treat a disorder, use of cell lines in studying mechanism of disease, and cell lines with sequence and/or copy number variations of a gene of interest are provided herein. In preferred embodiments, these methods are used to generate Parkinson's disease-specific cell lines, for use in elucidating Parkinson's disease mechanisms, diagnosis of Parkinson's disease, and screening for agents useful in the treatment or prevention of Parkinson's disease.

Starting with cells, such as human cells, induced pluripotent stem (iPS) cells are generated, for example, using combinations of transcription factors. In some embodiments, human cells obtained from a subject, for example, for the purpose of inducing dedifferentiation may be chosen from any human cell type, including fibroblast cells, tumor cells, bone marrow cells, stomach cells, liver cells, epithelial cells, nasal epithelial cells, mucosal epithelial cells, follicular cells, connective tissue cells, muscle cells, bone cells, cartilage cells, gastrointestinal cells, splenic cells, kidney cells, lung cells, testicular cells, nervous tissue cells, and lymphocytic cells transformed with Epstein-Barr virus. In some embodiments, the human cell type is a fibroblast, which may be conveniently obtained from a subject by a punch biopsy. In certain embodiments, the cells are obtained from subjects known or suspected to have a copy number variation (CNV) or mutation of the gene of interest. In other embodiments, the cells are from a patient presenting with idiopathic/sporadic form of the disease. In yet other embodiments, the cells are from a non-human subject. The cells are then differentiated to adopt a specific cell fate, such as neuronal cells, for example dopaminergic, cholinergic, serotonergic, GABAergic, or glutamatergic neuronal cell fates.

Somatic cells, with a combination of three, four, five, six, or more factors can be dedifferentiated/reprogrammed to a state apparently indistinguishable from embryonic stem cells (ESCs); these reprogrammed cells are termed "induced pluripotent stem cells" (iPSCs, iPCs, iPSCs) and can be produced from a variety of tissues.

The factors appear to reverse epigenetic landmarks thereby introducing pluripotency in the cells. iPSCs possess the ability to differentiate into the cell types of all three germ layers; in the mouse, contribution to the germ line has been observed. Therefore, patient-specific cell lines can be established for various applications, including the study of disease mechanisms and screening for potential therapeutics.

Using the methods described herein, human iPSCs may be generated from patients with specific diseases, for example Parkinson's disease, for example due to a triplication of the SNCA gene or due to a mutation in the LRRK2 gene and used for further applications such as screening or disease diagnostics.

Dedifferentiation/Reprogramming of Cells to Induced Pluripotency:

Differentiation of a cell is the process by which cells become structurally and functionally specialized, for example, during embryonic development or in vitro. By dedifferentiation or reprogramming, cells are restored to an unspecialized state. Dedifferentiation allows for respecialization into other cell types distinct from that of the cell which has undergone the dedifferentiation.

Once obtained, cells may be dedifferentiated by exposure to transcription factors such as, for example OCT4, SOX2, KL4, and optionally cMyc, NANOG, and/or LIN28. The induction of dedifferentiation includes exposing cells to characterized factors which are known to produce a specific lineage outcome in cells exposed to the factors, so as to target the dedifferentiation to that of a specific desired lineage and/or cell type of interest. The exposure to transcription factors may be accomplished, e.g., by viral or non-viral method of application or transduction. The outcome of the dedifferentiation is a cell line, i.e., a cell or cells that have the capacity to be propagated indefinitely or for long periods of time, including months to years in continuous culture.

Dedifferentiation is the induction of pluripotency, multipotency, or totipotency, whereby a cell is restored to a more undifferentiated condition such as pluripotency (having the potential to differentiate into any of the three germ layers (endoderm, ectoderm, mesoderm)); multipotency (having the potential to differentiate into some, but not all, tissue types); or totipotency (having the potential to rise to all the cell types that make up an organism plus all of the cell types that make up the extraembryonic tissues, such as the placenta). Using the established dedifferentiation protocols of Takahashi and others, one of skill in the art may produce a pluripotent cell and differentiate therefrom any cell derived from the three primary germ layers. One of skill in the art will appreciate, however, that, depending upon the cells obtained from the subject which are to be dedifferentiated, the desired cell line, and the desired lineage following differentiation of the cell line, varying degrees of dedifferentiation may be sufficient, where the varying degrees of dedifferentiation may optionally be effected by, for example, exposure of the cells to different combinations of transcription factors, the use of a combination of transcription factors in different proportions, exposure thereto for different periods of time, etc., such that full dedifferentiation is not performed where it is not required to produce the desired cell line. However, the protocols of Takahashi and others as discussed may be utilized to give rise to endodermal, ectodermal or mesodermal cell lines, or their progeny.

This invention can also be practiced using stem cells of various types, which may include the following non-limiting examples.

U.S. Pat. No. 5,851,832 reports multipotent neural stem cells obtained from brain tissue. U.S. Pat. No. 5,766,948 reports producing neuroblasts from newborn cerebral hemispheres. U.S. Pat. Nos. 5,654,183 and 5,849,553 report the use of mammalian neural crest stem cells. U.S. Pat. No. 6,040,180 reports in vitro generation of differentiated neurons from cultures of mammalian multipotential CNS stem cells. WO 98/50526 and WO 99/01159 report generation and isolation of neuroepithelial stem cells, oligodendrocyte-astrocyte precursors, and lineage-restricted neuronal precursors. U.S. Pat. No. 5,968,829 reports neural stem cells obtained from embryonic forebrain and cultured with a medium comprising glucose, transferrin, insulin, selenium, progesterone, and several other growth factors.

Except where otherwise required, the invention can be practiced using stem cells or induced pluripotent stem cells of any vertebrate species. Included are stem cells from humans; as well as non-human primates, domestic animals, livestock, and other non-human mammals.

Among the stem cells suitable for use in this invention are mammalian pluripotent and multipotent stem cells derived from tissue formed after gestation, such as a blastocyst, or fetal or embryonic tissue taken any time during gestation. Non-limiting examples are primary cultures or established lines of embryonic stem cells or embryonic germ cells.

Establishment of Embryonic Stem Cell Lines:

Embryonic stem cells can be isolated from blastocysts of members of the primate species (Thomson et al., Proc. Natl. Acad. Sci. USA 92:7844, 1995). Human embryonic stem (hES) cells can be prepared from human blastocyst cells using the techniques described by Thomson et al. (U.S. Pat. No. 5,843,780; Science 282:1145, 1998; Curr. Top. Dev. Biol. 38:133 ff., 1998) and Reubinoff et al, Nature Biotech. 18:399, 2000.

Briefly, human blastocysts are obtained from human in vivo preimplantation embryos. Alternatively, in vitro fertilized (IVF) embryos can be used, or one-cell human embryos can be expanded to the blastocyst stage (Bongso et al., Hum Reprod 4: 706, 1989). Embryos are cultured to the blastocyst stage in G1.2 and G2.2 medium (Gardner et al., Fertil. Steril. 69:84, 1998). The zona pellucida is removed from developed blastocysts by brief exposure to pronase (Sigma). The inner cell masses are isolated by immunosurgery, in which blastocysts are exposed to a 1:50 dilution of rabbit anti-human spleen cell antiserum for 30 min, then washed for 5 min three times in DMEM, and exposed to a 1:5 dilution of Guinea pig complement (Gibco) for 3 min (Solter et al., Proc. Natl. Acad. Sci. USA 72:5099, 1975). After two further washes in DMEM, lysed trophectoderm cells are removed from the intact inner cell mass (ICM) by gentle pipetting, and the ICM plated on mEF feeder layers.

After 9 to 15 days, inner cell mass-derived outgrowths are dissociated into clumps, either by exposure to calcium and magnesium-free phosphate-buffered saline (PBS) with 1 mM EDTA, by exposure to dispase or trypsin, or by mechanical dissociation with a micropipette; and then replated on mEF in fresh medium. Growing colonies having undifferentiated morphology are individually selected by micropipette, mechanically dissociated into clumps, and replated. ES-like morphology is characterized as compact colonies with apparently high nucleus to cytoplasm ratio and prominent nucleoli. Resulting ES cells are then routinely split every 1-2 weeks by brief trypsinization, exposure to Dulbecco's PBS (containing 2 mM EDTA), exposure to type IV collagenase (.about.200 U/mL; Gibco) or by selection of individual colonies by micropipette. Clump sizes of about 50 to 100 cells are optimal.

Genetic Variations:

The methods described herein include dedifferentiation of cells in order to produce a cell line with a genetic variation. Genetic variations include differences in DNA sequence (within coding and/or non-coding regions); differences in gene expression and heritable variances that exist among members of a species; polymorphisms, including, for example, nucleotide polymorphisms, restriction site polymorphisms, transitions, transversions, deletions, insertions, and duplications of one or more nucleotides; deletions, insertions, transpositions, and duplications of one or more genes; and gene copy number variations. Other types of genetic variations are known in the art.

In some embodiments, the genetic variation of interest is a copy number variation (CNV), also known as a copy number polymorphism (CNP). CNV encompasses the variation of the number of copies of a gene, or of sequences of DNA, in the genome of an individual. The CNV of the gene of interest may be of any type. Nonlimiting examples include duplication, triplication, deletion, insertion, complex multi-state variant of the gene of interest, and combinations thereof. Copy number variation has been linked to disease susceptibility and disease resistance.

The gene of interest may be any gene known or suspected to have a CNV or other genetic variation such as a mutation. Genes known to have a CNVs or mutations include α-synuclein (PARK1, SNCA), Parkin (PARK2), UCHL1 (PARK5), PINK1 (PARK6), DJ-1 (PARK7), LRRK2 (PARK5), GIGFY2 (PARK 11), SLC4A10, FHIT, FHIT, FLJ16237, A2BP1, and CCL3L1. One of skill in the art can readily determine which genes have a CNV using known techniques, or by reference to published sources.

For example, the Wellcome Trust Sanger Institute has developed DECIPHER (Database of Chromosomal Imbalance and Phenotype in Humans Using Ensembl Resources), a database of CNVs associated with clinical conditions, available online at https://decipher.sanger.ac.uk/. See also Lupski, J, Genome structural variation and sporadic disease traits, *Nat. Genet.* 38, 974-76 (2006). Foundations related to research on a disease condition frequently make available databases of genes associated with the disease. In the case of Parkinson's disease, the Michael J. Fox Foundation provides access to a comprehensive and regularly updated collection of genetic association studies performed on Parkinson's disease (PD) phenotypes, accessible by entering in a browser the URL http://www(dot)pdgene(dot)org/.

In further embodiments, the genetic variation of interest may be a variation in the nucleotide sequence of a gene, i.e., a mutation. The variation in the nucleotide sequence of the gene of interest includes any alteration in a polynucleotide and may be of any type. Nonlimiting examples include a deletion, substitution, transition, transversion, or duplication of one or more nucleotides in the gene of interest, and combinations thereof. One of skill in the art can readily determine which genes have a mutation of interest using known techniques, or by reference to published sources. For example, databases related to diseases associated with genetic mutations accessible by entering a URL into a browser include: medicalgenetics(dot)med(dot)ualberta (dot)ca/wilson/index(dot)php, molgen(dot)ua(dot)ac(dot) be/ADMutations/, bioinf(dot)uta(dot)fi/KinMutBase/, www (dot)humgen(dot)rwth-aachen(dot)de/index(dot) asp?subform=database(dot)html&nav=database_nav(dot) html, cooke(dot)gsf(dot)de/asthmaGen, life2(dot)tau(dot)ac (dot)il/GeneDis/, fmf(dot)igh(dot)cnrs(dot)fr/infevers/, imgt (dot)cines(dot)fr, www(dot)tmgh(dot)metro(dot)tokyo(dot) jp/jg-snp/english/E_top(dot)html, mutview(dot)dmb(dot) med(dot)keio(dot)ac(dot)jp/MutationView/jsp/mutview/ index(dot)jsp, www(dot)med(dot)mun(dot)ca/mmrvariant/, www(dot)thepi(dot)org/altruesite/files/parkinson/Mutations/new_page_1(dot)html, www(dot)pdgene(dot)org/, www(dot)retina-international(dot)org/sci-news/mutation (dot)htm, www(dot)ucl(dot)ac(dot)uk/ncl/mutation(dot) shtml, pkdb(dot)mayo(dot)edu/, www(dot)pathology(dot) washington(dot)edu/research/werner/database/ and www (dot)genet(dot)sickkids(dot)on(dot)ca/cftr/Home(dot)html.

In some embodiments, the present methods include identifying a subject with a genetic variation of interest, and obtaining one or more cells from the subject to obtain one or more cells with the genetic variation of interest. Suitable subjects include, for example, any species from which at least one cell can be utilized for dedifferentiation, such as humans, non-human primates, and non-primate mammals such as (but not limited to) rodents. Genetic variations of interest may include, for example, genetic variations associated with diseases, disorders, or antigens of interest.

In some embodiments, the genetic variation of interest is associated with a disorder, e.g., a disease. The genetic variation may be a variation in a gene or gene product, cellular pathway, etc., which is causative, symptomatic, or diagnostic of any disease, disorder, illness and the like. Disease-associated genes include, but are not limited to, a gene, a genomic region about 10 kb upstream and 10 kb downstream of such gene, regulatory regions that modulate the expression of the gene, and all associated gene products (e.g., isoforms, splicing variants, and/or modifications, derivatives, etc.). The sequence of a disease-associated gene may contain one or more disease-related sequence polymorphisms. For example, the sequence of a Parkinson's disease-related gene in an individual may contain one or more reference (i.e. "normal") or alternate alleles, or may contain a combination of reference and alternate alleles, or may contain alleles in linkage disequilibrium with one or more polymorphic regions. The genetic variation of interest may include a CNV or a variation in the nucleotide sequence of a gene, i.e., a mutation. One of skill in the art can readily identify genetic variations associated with a disorder using known techniques, or by reference to published sources.

In some embodiments, the subject with the genetic variation of interest has been diagnosed with a disorder or a predisposition to a disorder. In some embodiments, the subject has been diagnosed with a genetic disorder or a predisposition to a genetic disorder. In certain embodiments, the subject has been diagnosed with a neurodegenerative disorder. Disorders include, but are not limited to, Parkinson's disease (PD), PD-related diseases, toxicity-induced Parkinsonism, Alzheimer's disease, dementia, an autism spectrum disorder, susceptibility to viral infection such as HIV, and CHARGE Syndrome. Autism spectrum disorders include Asperger syndrome, autism, pervasive developmental delay (PDD) not otherwise specified, and Rett disorder. A PD-related disease refers to one or more diseases, conditions or symptoms or susceptibilities to diseases, conditions or symptoms, that involve, directly or indirectly, neurodegeneration including but not limited to the following: Alzheimer's disease, amyotrophic lateral sclerosis (ALS), Alpers' disease, Batten disease, Cockayne syndrome, corticobasal ganglionic degeneration, Huntington's disease, Lewy body disease, Pick's disease, motor neuron disease, multiple system atrophy, olivopontocerebellar atrophy, Parkinson's disease, postpoliomyelitis syndrome, prion diseases, progressive supranuclear palsy, Rett syndrome, Shy-Drager syndrome and tuberous sclerosis. In certain aspects, a PD-related disease is a neurodegenerative disease the affects neurons in the brain. A PD-related disease may be e.g. a condition that is a risk factor for developing PD, or may be a condition for which PD is a risk factor, or both.

Other known disorders which are related to CNV wherein the present methods may find use include but are not limited to: 12q14 microdeletion syndrome, 15q13.3 microdeletion syndrome, 15q24 recurrent microdeletion syndrome, 16p11.2-p12.2 microdeletion syndrome, 17q21.3 microdeletion syndrome, 1p36 microdeletion syndrome, 1q21.1 recurrent microdeletion, 1q21.1 recurrent microduplication, 1q21.1 susceptibility locus for Thrombocytopenia-Absent Radius (TAR) syndrome, 22q11 deletion syndrome (Velocardiofacial/DiGeorge syndrome), 22q11 duplication syndrome, 22q11.2 distal deletion syndrome, 22q13 deletion syndrome (Phelan-Mcdermid syndrome), 2p15-16.1 microdeletion syndrome, 2q33.1 deletion syndrome, 2q37 monosomy, 3q29 microdeletion syndrome, 3q29 microduplication syndrome, 6p deletion syndrome, 7q11.23 duplication syndrome, 8p23.1 deletion syndrome, 9q subtelomeric deletion syndrome, adult-onset autosomal dominant leukodystrophy (ADLD), Angelman syndrome (Type 1), Angelman syndrome (Type 2), ATR-16 syndrome, AZFa, AZFb, AZFb+AZFc, AZFc, Cat-Eye Syndrome (Type I), Charcot-Marie-Tooth syndrome type 1A (CMT1A), Cri du Chat Syndrome (5p deletion), early-onset Alzheimer disease with cerebral amyloid angiopathy, familial adenomatous polyposis, hereditary liability to pressure palsies (HNPP), Leri-Weill dyschondrostosis (LWD)-SHOX deletion, Miller-Dieker syndrome (MDS), NF1-microdeletion syndrome, Pelizaeus-Merzbacher disease, Potocki-Lupski syndrome (17p11.2 duplication syndrome), Potocki-Shaffer syndrome, Prader-Willi syndrome (Type 1), Prader-Willi syndrome (Type 2), RCAD (renal cysts and diabetes), Rubinstein-Taybi syndrome, Smith-Magenis syndrome, Sotos syndrome, split hand/foot malformation 1 (SHFM1), steroid sulphatase deficiency (STS), WAGR 11p13 deletion syndrome, Williams-Beuren syndrome (WBS), Wolf-Hirschhorn syndrome, and Xq28 (MECP2) duplication.

In some embodiments, the subject with the genetic variation of interest has been diagnosed with a disorder or predisposition to a disorder associated with protein aggregation. Protein aggregation includes nonspecific coalescence of misfolded proteins, driven by interactions between solvent-exposed hydrophobic surfaces that are normally buried within a protein's interior. Normal interactions between misfolded proteins with normal cellular constituents have been proposed to underlie the toxicity associated with protein aggregates in many neurodegenerative disorders. Such disorders include, for example, Alzheimer's disease, Parkinson's disease, dementia, autism spectrum disorders, susceptibility to viral infection, diffuse Lewy body disease, other Lewy body disorders, synucleinopathy, corticobasal degeneration, encephalitis lethargica, multiple system atrophy, pantothenate kinase-associated neurodegeneration (Hallervorden-Spatz syndrome), progressive supranuclear palsy, vascular Parkinsonism, Wilson disease, hereditary pancreatitis, glomerulonephritis, human systemic lupus erythematosus, paraneoplastic syndrome, frontotemporal dementia with Parkinsonism chromosome 17, Huntington's disease, spinocerebellar ataxias, amytropic lateral sclerosis, and Creutzfeldt-Jakob disease.

Differentiation of Cell Lines:

In some embodiments, the methods described herein further include inducing differentiation of the cell line with the genetic variation of interest. Differentiation of cells is accomplished by exposing cells to characterized factors which are known to produce a specific lineage outcome in the cells so exposed, so as to target their differentiation to that of a specific, desired lineage and/or cell type of interest. Cells which are terminally differentiated display phenotypic characteristics of specialization and often lose the capacity to undergo indefinite culturing, exhibiting slowed proliferation.

The iPSCs as described herein may be differentiated into various cell types including any cell type of interest including endodermal (giving rise to cells of the endoderm, which gives rise to inner tissues and organs such as the alimentary canal, gut, digestive glands, respiratory system, and intestines/bladder), ectodermal (giving rise to cells of the ectoderm, which gives rise to the nervous system, skin, and other outermost specialized tissues and organs), mesodermal (giving rise to cells of the mesoderm; mesoderm is the middle germ layer of an embryo coming from the inner cell mass of the blastocyst; it gives rise to bone, muscle, connective tissues, including the dermis, the blood vascular system, the urogenital system except the bladder, and contributes to some glands), neuroectodermal (giving rise to any cells of the neuroectoderm, which gives rise to neurons, supporting cells, and ependyma of the central nervous system and the neural crest cells that form peripheral ganglia and a wide variety of other tissues), neural (giving rise to any cells of the nervous system peripheral and central; autonomic and somatic, including all neurons, support cells/glia, etc). In some embodiments, the cell line is differentiated into a population of cells, for example, a cobblestone-like cell line, a cardiomyocytic cell population, an epithelial cell population such as a keratin-containing or gut-like epithelial cell population, a gastrointestinal cell population, a respiratory cell population, a hepatic cell population, a pancreatic cell population, an endocrinic cell population, an epidermal cell population, a myogenic cell population, a cartilage cell population, a mucosal cell population, a skeletal cell population, a cartilage cell population, a nephritic cell population, a lymphatic cell population, a splenic cell population, or the precursors of any of the preceding.

In some embodiments, the cell population derived from the iPSCs is a multipotent cell population. In some embodiments, the cell population derived from the iPSCs is a monopotent cell population. In some embodiments, the cell population derived from the iPSCs is a terminally differentiated cell population. In some embodiments, the cell population derived from the iPSCs is capable of undergoing passage in culture without observed replicative crisis, up to and including days, weeks, months and years of passage in cell culture. In some embodiments, the cell population derived from the iPSCs is incapable of undergoing passage in culture without observed replicative crisis. In each case, the ordinarily skilled artisan can readily assess the viability and lineage potency of the derived cell population using methods known in the art.

In certain embodiments, the cell line is differentiated into a neuroectodermal, neuronal, neuroendocrine, dopaminergic, cholinergic, serotonergic (5-HT), glutamatergic, GABAergic, adrenergic, noradrenergic, sympathetic neuronal, parasympathetic neuronal, sympathetic peripheral neuronal, or glial cell population, such as a microglial (amoeboid, ramified, activated phagocytic, activated non-phagocytic) or macroglial (central nervous system (CNS): astrocytes, oligodendrocytes, ependymal cells, radial glia; peripheral nervous system (PNS): Schwann cells, satellite cells) cell population, or the precursors of any of the preceding, including neural stem and progenitor cells.

Characterization of Cell Lines:

In some embodiments, the methods further include phenotypic characterization of the cell lines produced by the present methods, or of their progeny. For example, cells obtained from a subject with a genetic variation of interest and induced to pluripotency according to the present methods may be characterized, prior to any further use, for their capacity to support teratoma formation in a murine model as a confirmation of pluripotency. Following differentiation, the resulting progeny cells may be, for example, stained for markers of differentiation and subject to a teratoma formation assay to demonstrate completion of differentiation. The phenotypic characterization can comprise exposing the cell line to an agent or condition and observing any change or lack of change in the cell line.

Prior to and following differentiation of the subject iPSCs, the phenotypic characterization frequently comprises staining for one or more markers according to methods known in the art and discussed above. In many embodiments, the one or more markers are lineage markers such as Map2, type III beta tubulin, doublecortin, NeuN, glial fibrillary acidic protein, S100-beta, NG2, GalC, tyrosine hydroxylase, aromatic amino acid decarboxylase, Grk2, glutamate transporter, GAD, dopamine beta hydroxylase, cellular uptake system molecules, etc. See, e.g. Peng et al., supra. Lineage markers corresponding to other terminally differentiated neural subtypes, as well as to stem, progenitor and other cells, are known in the art and may be used as well.

In some embodiments, the cell derived from iPSCs according to the present methods is a neural cell; in certain embodiments, the cell line is differentiated into a neuroectodermal cell, neuronal cell, neuroendocrine cell, dopaminergic cell, cholinergic cell, serotonergic (5-HT) cell, glutamatergic cell, GABAergic cell, adrenergic cell, noradrenergic cell, sympathetic neuronal cell, parasympathetic neuronal cell, sympathetic peripheral neuronal cell, or glial cell, such as a microglial (amoeboid, ramified, activated phagocytic, activated non-phagocytic) or macroglial (CNS: astrocytes, oligodendrocytes, ependymal cells, radial glia; PNS: Schwann cells, satellite cells) cell, or precursors of any of the preceding.

In some embodiments, the change or lack of change is observed by staining for one or more markers of cytotoxicity, oxidative stress, cellular transport, apoptosis, mitochondrial function, ubiquitin function, and proteasomal function according to standard methods, as discussed herein. In some embodiments, the change or lack of change is observed by testing for one or more of ATP production, LDH release, activated caspase levels, and expression of alpha-synuclein. In some embodiments, the change or lack of change is observed by one or more of flow cytometry, quantitative real-time PCR, and induction of teratomas in mice. Those of skill in the art will be able to determine how to observe a change or lack of change with no more than routine skill.

Disorders with Genetic Variations:

In some embodiments, the subject with the genetic variation of interest has been diagnosed with a disorder or a predisposition to a disorder. Disorders wherein the present methods and compositions find use are described below, though one of skill in the art will appreciate that the methods described herein are generally applicable to all diseases and disorders involving CNV and other genetic variations.

Parkinson's Disease:

Parkinson's disease is one of the most common neurodegenerative diseases of aging. Approximately 1-2% of the population over 65 years is affected by this disorder, and it is estimated that the number of prevalent cases of Parkinson's disease will double by the year 2030 (Dorsey, E. R. et al. Projected number of people with Parkinson disease in the most populous nations, 2005 through 2030. *Neurology* 68, 384-6 (2007). The disease is slowly progressive with the cardinal features of rigidity, resting tremor, bradykinesia, and asymmetric onset, although it is now becoming apparent that the disease is widespread in the central and peripheral nervous system. Clinical manifestation of motor symptoms of Parkinson's disease starts when ~40-60% of the dopaminergic neurons in the substantia nigra of the midbrain have died. Neuropathologically, the key features include loss of dopaminergic neurons in the substantia nigra and other areas in the brain, and intracytoplasmic inclusions known as Lewy bodies, of which α-synuclein is a major component (Langston, J. W. The Parkinson's complex: parkinsonism is just the tip of the iceberg. *Ann Neurol* 59, 591-6 (2006).; Forman, M. S., Lee, V. M. & Trojanowski, J. Q. Nosology of Parkinson's disease: looking for the way out of a quagmire. *Neuron* 47, 479-82 (2005); Litvan, I. et al. The etiopathogenesis of Parkinson disease and suggestions for future research. Part II. *J Neuropathol Exp Neurol* 66, 329-36 (2007); Litvan, I. et al. The etiopathogenesis of Parkinson disease and suggestions for future research. Part I. *J Neuropathol Exp Neurol* 66, 251-7 (2007)). Currently there is no cure for the disease, nor is the cause of the disease known.

There are several other conditions that have the features of Parkinson's disease and are interchangeably referred to as Parkinson's-like disease, Parkinson's-related disease, secondary Parkinsonism, Parkinson's syndrome, or atypical Parkinson's disease. These are neurological syndromes that can be characterized by tremor, hypokinesia, rigidity, and postural instability. The underlying causes of Parkinson's-like disease are numerous, and diagnosis can be complex. A wide-range of etiologies can lead to a similar set of symptoms, including some toxins, a few metabolic diseases, and a handful of non-Parkinson's disease neurological conditions. A common cause is as a side effect of medications, mainly neuroleptic antipsychotics especially the phenothiazines (such as perphenazine and chlorpromazine), thioxanthenes (such as flupenthixol and zuclopenthixol) and butyrophenones (such as haloperidol (Haldol)), piperazines (such as ziprasidone), and rarely, antidepressants. Other causes include but are not limited to olivopontocerebellar degeneration, progressive supranuclear palsy, corticobasal degeneration, temporo-frontal dementia; drug induced like antipsychotics, prochlorperazine, metoclopromide; poisoning with carbon monoxide; head trauma; and Huntington's disease Parkinsonism. In some cases α-synucleinopathies can result in Parkinson's-like disease, secondary Parkinsonism, Parkinson's syndrome, or atypical Parkinson's.

Alzheimer's Disease:

Alzheimer's disease is a progressive neurodegenerative disorder which is the predominant cause of dementia in people over 65 years of age. Clinical symptoms of the disease generally begin with subtle short term memory problems and as the disease progresses, difficulties with memory, language and orientation occur more frequently. In late stage Alzheimer's disease, ventricular enlargement and shrinkage of the brain may be observed by magnetic resonance imaging. Some characteristic changes in the Alzheimer's disease brain include neuronal loss in selected regions; intracellular neurofibrillary tangles (NFTs) in the neurons of the cerebral cortex and hippocampus; and neuritic plaques containing amyloids that may be further surrounded by dystrophic neuriteism reactive astrocytes and microglia. See, e.g., Wisniewski et al., *Biochem. Biophys. Res. Comm.* 192:359 (1993). The NFTs characteristic of Alzheimer's disease consist of abnormal filaments bundled together in neuronal cell bodies. The intracellular neurofibrillary tangles are composed of polymerized tau protein, and abundant extracellular fibrils are comprised largely of beta-amyloid. Beta-amyloid, also known as $A_{beta}$, arises from the proteolytic processing of the amyloid precursor protein (APP) at the beta- and gamma-secretase cleavage sites giving rise to the cellular toxicity and amyloid-forming capacity of the two major forms of $A_{beta}$ ($A_{beta}40$ and $A_{beta}42$). Thus, preventing APP processing into plaque-producing forms of amyloid may critically influence the formation and progression of the disease making BACE1 (including variants thereof, e.g. variants A, B, C, and D) a clinical target for inhibiting or arresting this disease. The presenilins are additional candidate targets for redirecting aberrant processing. See, e.g., Tagami et al., *Neurodegener Dis.* 5(3-4):160-2 (2008). What are referred to as "Ghost" NFTs are also observed in Alzheimer's disease brains, presumably marking the location of dead neurons. Other neuropathic features of Alzheimer's disease include granulovacuolar changes, neural loss, gliosis and the variable presence of Lewy bodies. The identification between genetic loci and neurodegenerative changes or associations between genetic loci and the risk of developing a neurodegenerative disease may be useful in methods of diagnosing, screening and prognosing patients, as well as in therapeutic development methods. An accurate cellular model system for study of the disease would further these goals.

Autism Spectrum Disorders:

Autism spectrum (AS) disorders include three separate diagnoses, which include autism, Asperger's syndrome and Pervasive Developmental Delay (PDD). PDD is characterized by developmental delays of sociability, communication and use of imagination. Asperger's syndrome is a more severe form of PDD but lacks the language and intelligence deficits normally associated with autism. Autism is exemplified by severe communication impairments, social interaction deficits and repetitive/stereotypic behaviors. Each of these disorders has specific diagnostic criteria as outlined by the American Psychiatric Association (APA) in its Diagnostic & Statistical Manual of Mental Disorders (DSM-IV-TR). Autism impacts the normal development of the brain in the areas of social interaction and communication skills Children and adults with autism typically have difficulties in verbal and non-verbal communication, social interactions, and leisure or play activities. Data from whole-genome screens in multiplex families suggest interactions of at least 10 genes in the causation of autism. Thus far, a putative speech and language region at 7q31-q33 seems most strongly linked to autism, with linkages to multiple other loci. Cytogenetic abnormalities at the 15q11-q13 locus are fairly frequent in people with autism, and a "chromosome 15 phenotype" was described in individuals with chromosome 15 duplications. Among other candidate genes are the FOXP2, RAY1/ST7, IMMP2L, and RELN genes at 7q22-q33 and the GABA(A) receptor subunit and UBE3A genes on chromosome 15q11-q13. Variant alleles of the serotonin transporter gene (5-HTT) on 17q11-q12 are more frequent in individuals with autism than in nonautistic populations. See, e.g., Muhle et al., *Pediatrics* 113 (5):e472-86 (2004). A variant allele of the Engrailed gene, which maps to chromosome 7, in particular, to 7q36.3, has been implicated in the autism spectrum disorders. See, for example, US Patent Publication No. 2006/0141519.

Rett Syndrome:

Rett syndrome (or disorder) is a disorder of brain development that occurs almost exclusively in girls. After 6 to 18 months of apparently normal development, girls with the classic form of Rett syndrome develop severe problems with language and communication, learning, coordination, and other brain functions. Early in childhood, affected girls lose purposeful use of their hands and begin making repeated hand wringing, washing, or clapping motions. They tend to grow more slowly than other children and have a small head size (microcephaly). Other signs and symptoms can include breathing abnormalities, seizures, an abnormal curvature of the spine (scoliosis), and sleep disturbances. Researchers have described several variants of Rett syndrome with overlapping signs and symptoms. The atypical forms of this disorder range from a mild type, in which speech is preserved, to a very severe type that has no period of normal development. A form of Rett syndrome called the early-onset seizure variant has most of the characteristic features of classic Rett syndrome, but also causes seizures that begin in infancy. The condition affects an estimated 1 in 10,000-22,000 females.

Mutations in the CDKL5 and MECP2 genes cause Rett syndrome. Most cases of classic Rett syndrome are caused by mutations in the MECP2 (methyl CpG binding protein 2) gene. This gene provides instructions for making a protein (MeCP2) that is critical for normal brain development. The MeCP2 protein likely plays a role in forming connections (synapses) between nerve cells. It is believed that this protein has several functions, including regulating other genes in the brain by switching them off when they are not needed. The MeCP2 protein may also control the production of different versions of certain proteins in nerve cells. Although mutations in the MECP2 gene disrupt the normal function of nerve cells, it is unclear how these mutations lead to the signs and symptoms of Rett syndrome. See, e.g., Amir, et al., *Nat. Genet.* 23(2):127-8 (1999). Males with mutations in the MECP2 gene often die before birth or in infancy. A small number of males with a MECP2 mutation, however, have developed signs and symptoms similar to those of classic Rett syndrome. Some of these boys have an extra X chromosome in many or all of the body's cells. The extra X chromosome contains a normal copy of the MECP2 gene, which produces enough of the MeCP2 protein for the boys to survive. Other males with features of Rett syndrome have mutations in the MECP2 gene that occur after conception and are present in only a fraction of the body's cells. In rare cases, the MECP2 gene is abnormally duplicated in boys with mental retardation and some developmental problems characteristic of Rett syndrome.

Mutations in the CDKL5 (cyclin-dependent kinase-like 5) gene cause an atypical form of Rett syndrome in females called the early-onset seizure variant. See, e.g., Evans et al., *Eur J Hum Genet.* 13(10): 1113-20 (2005). The CDKL5 gene provides instructions for making a protein that appears to be essential for normal brain development. Although the function of this protein is unknown, it may play a role in regulating the activity of other genes. The CDKL5 protein acts as a kinase. At least 10 mutations in the CDKL5 gene, some in the kinase domain, have been identified in girls with atypical form Rett syndrome. This severe form of the disorder includes many of the features of classic Rett syndrome (including developmental problems, loss of language skills, and repeated hand wringing or hand washing movements), but also causes recurrent seizures beginning in infancy. How the identified defects in the CDKL5 gene produce the symptoms remains unclear.

Lewy Body Disease:

Lewy Body disease, or Dementia with Lewy Bodies (DLB) is one of the most common types of progressive dementia. The central feature of DLB is progressive cognitive decline, combined with three additional defining features: (1) pronounced "fluctuations" in alertness and attention, such as frequent drowsiness, lethargy, lengthy periods of time spent staring into space, or disorganized speech; (2) recurrent visual hallucinations, and (3) parkinsonian motor symptoms, such as rigidity and the loss of spontaneous movement. Individuals may also suffer from depression. The symptoms of DLB are caused by the build-up of Lewy bodies, i.e., accumulated bits of alpha-synuclein protein, inside the nuclei of neurons in areas of the brain that control particular aspects of memory and motor control. It is not understood why alpha-synuclein accumulates into Lewy bodies or how Lewy bodies cause the symptoms of DLB.

Alpha-synuclein accumulation is also linked to Parkinson's disease, multiple system atrophy, and several other disorders, which are referred to as the "synucleinopathies." DLB usually occurs sporadically, in people with no known family history of the disease. However, rare familial cases have occasionally been reported. Genes associated with DLB include SNCA, encoding alpha synuclein and GBA, encoding beta-glucocerebrosidase.

Hallervorden-Spatz Syndrome:

Pantothenate kinase-associated neurodegeneration (PKAN), also known as Hallervorden-Spatz syndrome, is a degenerative disease of the brain, which can lead to the display of parkinsonism in the affected individual. Neurodegeneration in PKAN is accompanied by an excess of iron that progressively builds in the brain. Symptoms typically begin in childhood and are progressive, often resulting in death by early adulthood. Symptoms of PKAN begin before middle childhood, and most often are noticed before ten years of age. Symptoms include dystonia, dysphagia & dysarthria due to involvement of muscle groups involved in speech, rigidity/stiffness of limbs, tremor, writhing movements, dementia, spasticity, weakness, seizures and pigmentary retinopathy, another degenerative condition that affects the individual's retina, often causing alteration of retinal color and progressive deterioration of the retina at first causing night blindness and later resulting in a complete loss of vision. 25% of individuals experience an uncharacteristic form of PKAN that develops post-10 years of age and follows a slower, more gradual pace of deterioration than those pre-10 years of age. These individuals face significant speech deficits as well as psychiatric and behavioral disturbances. Being a progressive, degenerative nerve illness, Hallervorden-Spatz leads to early immobility and often death by early adulthood.

PKAN is an autosomal recessive disorder, and those heterozygous for the disorder may not display any atypical characteristics that are considered suggestive of the disorder. The disorder is caused by a mutant PANK2 gene located at the chromosomal locus: 20p13-p12.3. PANK2 encodes pantothenate kinase 2, which in turn is responsible for preventing the accumulation of N-pantothenoyl-cysteine and pantetheine. It is believed that when this accumulation is not suppressed, the result is direct cell toxicity or cell toxicity as a result of free radical damage due to the lack of suppression. PANK2 encodes a 1.85 Kb transcript which is derived from seven exons covering a total distance of approximately 3.5 Mb of genomic DNA. The PANK2 gene also encodes a 50.5-kDa protein that is a functional pantothenate kinase, an essential regulatory enzyme in coenzyme A (CoA) biosynthesis, and catalyzing the phosphorylation of pantothenate (Vitamin B5), N-pantothenoyl-cysteine, and pantetheine (OMIM). Mutant PANK2 gene coded proteins are often caused by null or missense mutations, most notably a 7 bp deletion in the PANK2 gene coding sequence. See, e.g., Pellecchia et al., The diverse phenotype and genotype of pantothenate kinase-associated neurodegeneration, *Neurology* 64 (10): 1810-2 (2005).

Progressive Supranuclear Palsy:

Progressive supranuclear palsy (PSP) is a rare degenerative disorder involving the gradual deterioration and death of selected areas of the brain. The sexes are affected approximately equally and there is no racial, geographical or occupational predilection. Approximately 6 people per 100,000 population have PSP. The initial symptom in two-thirds of cases is loss of balance and falls. Other common early symptoms are changes in personality, general slowing of movement, and visual symptoms. Later symptoms and signs are dementia (typically including loss of inhibition and ability to organize information), slurring of speech, difficulty swallowing, and difficulty moving the eyes, particularly in the vertical direction. The latter accounts for some of the falls experienced by these patients as they are unable to look up or down. Some of the other signs are poor eyelid function, contracture of the facial muscles, a backward tilt of the head with stiffening of the neck muscles, sleep disruption, urinary incontinence and constipation Fewer than 1% of those with PSP have a family member with the same disorder. A variant in the gene for tau protein called the H1 haplotype, located on chromosome 17, has been linked to PSP. Nearly all individuals with PSP bear a copy of that variant from each parent, but this is true of about two-thirds of the general population. Therefore, the H1 haplotype appears to be necessary but not sufficient to cause PSP. Other genes, as well as environmental toxins, are being investigated as causal contributors to PSP.

Wilson Disease:

Wilson disease is a rare autosomal recessive inherited disorder of copper metabolism. The condition is characterized by excessive deposition of copper in the liver, brain, and other tissues. The major physiologic aberration is excessive absorption of copper from the small intestine and decreased excretion of copper by the liver. The genetic defect, localized to chromosome arm 13q, has been shown to affect the copper-transporting adenosine triphosphatase (ATPase) gene ATP7B in the liver. Patients with Wilson disease usually present with liver disease during the first decade of life or with neuropsychiatric illness during the third decade. The diagnosis is confirmed by measurement of serum ceruloplasmin, urinary copper excretion, and hepatic copper content, as well as the detection of Kayser-Fleischer rings. Initially, Wilson postulated that the familial incidence of hepatolenticular degeneration was attributable to environmental factors rather than genetic factors. Nearly a decade later, Hall reported that Wilson disease was more frequent in siblings. In 1953, Bearn discovered an autosomal recessive mode of inheritance confirmed by extended genetic analysis of 30 families. Frydman et al localized the Wilson disease (WD) gene to chromosome 13. The WD gene product is a 1411 amino acid protein with highest levels of expression in the liver, kidneys, and placenta. The WD gene codes for P-type copper-transporting ATPase, now characterized as ATP7B. Many of the gene defects for ATP7B are small deletions, insertions, or missense mutations. Most patients carry different mutations on each of their 2 chromosomes. More than 40 different mutations have been identified, the most common of which is a change from a histidine to a glutamine (H1069Q). See, for example, Thomas, et al., The Wilson disease gene: spectrum of mutations and their consequences, *Nat. Genet.* 9(2):210-7 (1995).

Use of Induced Pluripotent Cell Lines for Screening

Methods of screening the cell lines or cell populations (iPSCs or differentiated iPSCs) with a variation of a gene of interest for an agent to treat a disease or disorder are also provided. The methods comprise contacting an agent to be screened with a cell line or cell population described herein, observing a change or lack of change in the one or more cells, where the change or lack of change is correlated with an ability of the agent to treat the disease or disorder. In other words, the change or lack of change can be indicative of an ability of the agent to treat the disease or disorder. Agents to be screened include potential and known therapeutics. Such therapeutics include, but are not limited to, small molecules; aptamers, antisense molecules; antibodies and fragments thereof; polypeptides; proteins; polynucleotides; organic compounds; cytokines; cells; genetic agents including, for example, shRNA, siRNA, a virus or genetic material in a liposome; an inorganic molecule including salts such as, for example, lithium chloride or carbonate; and the like.

In some embodiments, the methods of screening the cell lines or cell populations with a variation of a gene of interest for an agent to treat a disease or disorder include comparison of the cell lines or populations with another cell line or population. For example, the cell lines or cell populations described herein may be compared to a normal cell line or population, meaning a cell line derived from a patient with no known symptoms or who has not been diagnosed with the disease or disorder of interest. Alternatively, the cell lines or cell populations described herein may be compared to a cell line or population of idiopathic cells, meaning cell lines or populations derived from patients who present with symptoms of the disease or disorder of interest, or have been diagnosed with the disease or disorder, but who do not have a variation of the gene of interest, and where the cause of the disease or disorder may even be unknown (sporadic or idiopathic). In other embodiments, the methods of screening the cell lines or cell populations with a variation of a gene of interest for an agent to treat a disease or disorder involve comparison of the cell lines or cell populations derived from a cell containing a genetic variation of interest to both a normal cell line or cell population and an cell line isolated from a subjecting presenting with an idiopathic/unknown form of disease or population. In some embodiments, the normal cell line or cell population and the idiopathic cell line or population will have been generated using the same protocol as that used to generate the cell line or population containing the genetic variation of interest. Thus, the normal cell line or cell population may serve as a control. As well, any change or lack of change in the control cells, idiopathic cells, and cells with the genetic variation of interest upon contacting with an agent may be compared to one another. Patients or groups of patients with idiopathic disease may thereby be compared to patients with genetic variations of interest with respect to their responsiveness to an agent, to a class of agent, to an amount of agent, and the like. In this way, idiopathic diseases are classified by their responsiveness to agents, yielding information about the etiology of the idiopathic disease and, alternatively or additionally, agents are identified which are effective across one or more classes of disease. It is envisioned that these methods are additionally used to develop treatment regimens for patients or classes of patients with a disease.

In other embodiments cell lines are created from patients presenting with an idiopathic form of disease and such cell lines are used for screening, and identification of disease mechanisms or disease diagnosis, independent of cells lines in which genetic variations exist.

In some embodiments, the cell lines or cell populations are screened by staining for a marker and observing a change. Nonlimiting examples of a change or lack of change include a change or lack of change in cell viability, cellular chemistry, cellular function, mitochondrial function, cell aggregation, cell morphology, cellular protein aggregation, gene expression, cellular secretion, or cellular uptake. Cell stains are known to those of skill in the art. Nonlimiting examples include markers of general cytotoxicity in cell viability assays, markers of apoptosis, markers of oxidative stress, markers of mitochondrial function, and combinations thereof. Alternatively, or additionally, screening may be effected by testing for one or more of ATP production, LDH release, activated caspase levels, expression of the gene of interest. In certain embodiments, the screening is for expression of the gene of interest α-synuclein. See, e.g., Andreotti, P. E. et al. Chemosensitivity testing of human tumors using a microplate adenosine triphosphate luminescence assay: Clinical correlation for cisplatin resistance of ovarian carcinoma. Cancer Res. 55, 5276-82 (1995); Beckers, B. et al. Application of intracellular ATP determination in lymphocytes for HLA typing. *J. Biolumin. Chemilumin.* 1, 47-51 (1986); Crouch, S. P. M. et al. The use of ATP bioluminescence as a measure of cell proliferation and cytotoxicity. J. Immunol. Meth. 160, 81-8 (1993); O'Brien, J. et al. Investigation of the alamar blue (resazurin) fluorescent dye for the assessment of mammalian cell cytotoxicity. *Eur. J. Biochem.* 267, 5421-6 (2000); Riss, T. and Moravec, R. A. Use of multiple assay endpoints to investigate effects of incubation time, dose of toxin and plating density in cell-based cytotoxicity assays. *Assay Drug Dev. Technol.* 2, 51-62 (2004).

The cells of the present method may be used for screening biological response modifiers, i.e., compounds and factors that affect the various signaling pathways, including pathways in dopaminergic neuronal cells. A wide variety of assays may be used for this purpose, including immunoassays for protein production, amount, secretion or binding; determination of cell growth, differentiation and functional activity; production of hormones; production of neurotransmitters; production of neurohormones; measurement of reactive oxygen species and/or free radical-mediated damage; and the like. See, e.g., Filipov et al., *Toxicology* 232 (1-2):68-78 (2007); Peng et al., *J. Neurosci.* 26(45):11644-51 (2006); Yan et al., Analysis of oxidative modification of proteins. *Curr Protoc Cell Biol.*, Chapter 7:Unit 7.9 (2002); Armstrong et al., Measurement of Reactive Oxygen Species in Cells and Mitochondria, *Methods in Cell Biology*, Vol 80, Chapter 18 (2007).

For example, the subject cells may be used to screen for agents that enhance or inhibit apoptosis, or the expression of α-synuclein. Typically the candidate agent will be added to the cells, and the response of the cells monitored through evaluation of cell surface phenotype, functional activity, patterns of gene expression, physiological changes, electrophysiological changes and the like. In some embodiments, screening assays are used to identify agents that have a low toxicity in human cells.

The term "agent" as used herein describes any molecule, e.g., nucleic acid, protein or pharmaceutical, with the capability of affecting a change in a parameter of interest in the cells of the assay. Generally a plurality of assay mixtures are run in parallel with different agent conditions and/or concentrations to obtain a differential response to the various concentrations. Typically, one of these conditions serves as a negative control, i.e., at zero concentration or below the level of detection. Screening may be directed to known pharmacologically active compounds and chemical analogs thereof.

Candidate agents encompass numerous chemical classes, including organic molecules. Candidate agents may comprise functional groups necessary for structural interaction with proteins, such as hydrogen bonding, and may include at least one amine, carbonyl, hydroxyl or carboxyl group. In certain embodiments, the candidate agents have at least two of the functional chemical groups. The candidate agents may comprise cyclical carbon or heterocyclic structures and/or aromatic or polyaromatic structures substituted with one or more functional groups. Candidate agents may also be found among biomolecules including, but not limited to: peptides, saccharides, fatty acids, steroids, purines, pyrimidines, derivatives, structural analogs or combinations thereof.

Candidate agents may be obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g., magnetic particles, and the like. Specific binding molecules include pairs, such as biotin and streptavidin, digoxin and antidigoxin etc. For the specific binding members, the complementary member would often be labeled with a molecule that provides for detection, in accordance with known procedures.

A variety of other reagents may be included in the screening assay. These include reagents like salts, neutral proteins, e.g., albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components is added in any order that provides for binding, delivery or effect. Incubations are performed at any suitable temperature, typically ranging from 4 to 40° C., but may be higher or lower than these temperatures. Incubation periods may be selected for optimum activity, but may also be optimized to facilitate rapid high-throughput screening.

Detection of change or lack of change in the cells may utilize staining of cells, performed in accordance with conventional methods. The antibodies of interest are added to the cell sample, and incubated for a period of time sufficient to allow binding to the epitope, for example, at least about 10 minutes. The antibody may be labeled with a label, for example, chosen from radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc. One exemplary use of staining in the present methods is described below in more detail.

Cellular gene expression may be assessed following a candidate treatment or experimental manipulation. The expressed set of genes may be compared with control cells of interest, e.g., cells also derived according to the present methods but which have not been contacted with the agent. Any suitable qualitative or quantitative methods known in the art for detecting specific mRNAs can be used. mRNA can be detected by, for example, hybridization to a microarray, in situ hybridization in tissue sections, by reverse transcriptase-PCR, or in Northern blots containing poly A+ mRNA. One of skill in the art can readily use these methods to determine differences in the size or amount of mRNA transcripts between two samples. For example, the level of particular mRNAs in cells contacted with agent is compared with the expression of the mRNAs in a control sample.

mRNA expression levels in a sample can be determined by generation of a library of expressed sequence tags (ESTs) from a sample. Enumeration of the relative representation of ESTs within the library can be used to approximate the relative representation of a gene transcript within the starting sample. The results of EST analysis of a test sample may then be compared to EST analysis of a reference sample to determine the relative expression levels of a selected polynucleotide.

Alternatively, gene expression in a test sample may be performed using serial analysis of gene expression (SAGE) methodology (Velculescu et al., Science (1995) 270:484). In short, SAGE involves the isolation of short unique sequence tags from a specific location within each transcript. The sequence tags are concatenated, cloned, and sequenced. The frequency of particular transcripts within the starting sample is reflected by the number of times the associated sequence tag is encountered with the sequence population.

Gene expression in a test sample may also be analyzed using differential display (DD) methodology. In DD, fragments defined by specific sequence delimiters (e.g., restriction enzyme sites) are used as unique identifiers of genes, coupled with information about fragment length or fragment location within the expressed gene. The relative representation of an expressed gene with a sample can then be estimated based on the relative representation of the fragment associated with that gene within the pool of all possible fragments. Methods and compositions for carrying out DD are well known in the art, see, e.g., U.S. Pat. Nos. 5,776,683 and 5,807,680.

Alternatively, gene expression in a sample may be assessed using hybridization analysis, which is based on the specificity of nucleotide interactions. Oligonucleotides or cDNA can be used to selectively identify or capture the DNA or RNA of specific sequence composition, and the amount of RNA or cDNA hybridized to a known capture sequence determined qualitatively or quantitatively, to provide information about the relative representation of a particular RNA message within the pool of cellular RNA messages in a sample. Hybridization analysis may be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry).

In another screening method, the test sample is assayed at the protein level. Methods of analysis may include 2-dimensional gels; mass spectroscopy; analysis of specific cell fraction, e.g., lysosomes; and other proteomics approaches. For example, detection may utilize staining of cells or histological sections (e.g., from a biopsy sample) with labeled antibodies, performed in accordance with conventional methods. Cells can be permeabilized to stain cytoplasmic molecules. In general, antibodies that specifically bind a differentially expressed polypeptide are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g., fluorescein, rhodamine, Texas red, etc.). The presence or absence of antibody binding may be determined by various methods, including flow cytometry of dissociated cells, microscopy, radiography, scintillation counting, etc. Any suitable alternative methods can of qualitative or quantitative detection of levels or amounts of differentially expressed polypeptide can be used, for example ELISA, western blot, immunoprecipitation, radioimmunoassay, etc.

Conditioned media, i.e., media in which cells of the methods described herein have been grown for a period of time sufficient to allow secretion of soluble factors into the culture, may be isolated at various stages and the components analyzed for the presence of factors secreted by the cells. Separation can be achieved with HPLC, reversed phase-HPLC, gel electrophoresis, isoelectric focusing, dialysis, or other non-degradative techniques, which allow for separation by molecular weight, molecular volume, charge, combinations thereof, or the like. One or more of these techniques may be combined to enrich further for specific fractions.

Use of Induced Pluripotent Cell Lines to Elucidate Disease Progression and Mechanism In some embodiments, the cell lines and cell populations (iPSCs or differentiated iPSCs) described herein are used to study the mechanism of a disease of interest. In such embodiments, a molecular determinant of a disorder of interest is identified by contacting one or more test cells from a cell line derived by the method as described herein with an agent or condition which affects a pathway of interest, such as a cellular pathway, such as a disease-associated gene pathway, and observing any change or lack of change in the one or more test cells. A disease-associated gene pathway generally refers to genes and gene products comprising a disease-associated gene, and may include one or more genes that act upstream or downstream of a disease-associated gene in a disease related pathway; or any gene whose gene product interacts with, binds to, competes with, induces, enhances or inhibits, directly or indirectly, the expression or activity of a disease-associated gene; or any gene whose expression or activity is induced, enhanced or inhibited, directly or indirectly, by a disease-associated gene; or any gene whose gene product is induced, enhanced or inhibited, directly or indirectly, by a disease-associated gene. A disease-associated gene pathway may refer to one or more genes or the gene products which act in a signaling pathway. Direct and indirect mechanisms refer, respectively, to direct contact or modification of a molecular actor in a pathway and contact or modification of an intermediary molecule which in turn contacts or modifies a molecular actor in a pathway, as is known in the art. Indirect mechanisms may be one or more steps removed from direct influence on a pathway. "Molecular determinants," as used herein, refers to any of the genes or gene products which may act, directly or indirectly, in a disease-associated gene pathway.

In some embodiments, the test cells are compared to one or more control cells. In some of these embodiments, such control cells are cells of the test cell line that have not been contacted with the agent or condition as described above. In further embodiments, such control cells are from a second cell line derived from a cell type which is the same as that of the test cell line with the exception that it lacks the genetic variation of interest; i.e., the second cell line is produced by inducing dedifferentiation according to the same method used to dedifferentiate the test cell line; and the resulting control cell line is contacted with the same agent or condition as the test cell line during experimentation.

In the methods employing genetic agents, polynucleotides may be added to the cells in order to alter the genetic composition of the cells. Output parameters are monitored to determine whether there is a change in phenotype affecting particular pathways in cells derived from iPS cell lines obtained from subjects diagnosed with a disease relative to those without. In this way, genetic sequences may be identified that encode or affect expression of proteins in pathways of interest, particularly pathways associated with aberrant physiological states such as the disease of interest.

In some embodiments of the present method, agents of interest may be naturally occurring compounds such as, e.g., known compounds that have surface membrane receptors and induce a cellular signal that results in a modified phenotype, or synthetic compounds that mimic the naturally occurring agents. In some embodiments, agents of interest include inorganic compounds such as salts which are known to affect a particular cellular pathway or pathways. In some instances, the agents will act intracellularly by passing through the cell surface membrane and entering the cytosol with binding to components in the cytosol, nucleus or other organelle.

In some embodiments, the cells are subjected to a condition, which triggers the activities of known factors in response to the condition, using the activity of the naturally occurring factors to thereby identify pathways and molecules associated with the disease of interest. Such conditions include, for example, hypoxic or anoxic conditions or any condition resulting in oxidative, endoplasmic reticular or mitochondrial stress.

For assays with genetic agents, the same approach may be used. The genetic agents are added to cells, which may be derived from iPS obtained from a subject diagnosed with a disorder of interest, e.g., a disease. Parameters associated with the pathways related to the disease state are monitored. Where the parameters show a pattern indicating the up or down regulation of a pathway, the agent or condition is deduced to encode or affect the expression of a member of the pathway that has an effect on the disease state. In this way one can determine the role a gene plays in the physiological state of interest, as well as define targets for therapeutic application.

In some embodiments of the methods described herein, the change or lack of change in the cells is observed by staining, according to known methods. The staining may be for one or more markers, for example, one or more markers of cytotoxicity, oxidative stress, cellular transport, apoptosis, mitochondrial function, ubiquitin function, lysosomal function and proteasomal function. The change or lack of change may be observed by testing for one or more of ATP production, LDH release, activated caspase levels, and expression of alpha-synuclein according to methods as described. The change or lack of change in cells is observed by one or more of, for example, flow cytometry, quantitative real-time PCR, and induction of teratomas in mice.

Use of Induced Pluripotent Cell Lines for Diagnostics, Prognostics, and Theranostics Also provided herein are methods of determining the progression of a disorder and methods of determining the rate of progression of a disorder, useful for disease diagnosis, prognosis, and theranosis. The methods includes producing an iPS cell line from an individual diagnosed with the disorder according to the methods described herein, observing any change or lack of change in the cell line or progeny thereof, correlating the change or lack of change with progression and/or rate of progression, obtaining a tissue sample from a control subject and observing the change or lack of change in the tissue sample from the subject, where the change or lack of change is indicative of the progression of a disorder and/or rate of disease progression. The subject methods use an observed characteristic of an iPS, or its progeny derived from an individual diagnosed with the disorder, as a way of determining the progression and/or rate of progression of the disorder in, e.g., a second individual. The methods may further include contacting the iPS cell or its progeny with an agent or condition and observing the change or lack of change. In the subject methods, the change or lack of change is indicative of the progression and/or rate of progression of the disorder. The change or lack of change can be a change in one or more of morphology, gene expression, protein synthesis, and secretion of gene products from the cell line, as well as other changes known to those of skill in the art. This change or lack of change in the iPS cell or progeny obtained from a first individual may be correlated with disease progression and/or rate of disease progression by, for example, detecting relative amounts of the change or lack of change in tissue samples (for example, a primary tissue sample) from individuals with early and late stage progression of the disorder or slow-progressing and fast-progressing disorders. Once this correlation has been observed, the subject change or lack of change may be used as a signature to determine the stage, i.e., progression, of the disorder in the same or in another individual diagnosed with the disorder. Alternatively, or in addition, the change or lack of change may be used as a signature to determine the rate of progression of the disorder in the same or in another individual diagnosed with the disorder. For example, patients diagnosed with a disorder may be further classified as having a slow-progressing or a fast-progressing disorder. In this way, a characteristic of an iPS cell line or its progeny derived according to the methods herein is used to assess the progression or rate of progression of a disorder, the progression or rate thereof is directly or indirectly related to the characteristic.

Methods of Treatment

Methods of treating and/or preventing a disorder (e.g., disease) in a subject in need thereof are provided herein. The methods involve administering to the subject an agent, e.g., identified by the screening methods described herein, in an effective amount to treat or prevent the disorder.

Any disorder associated with CNV or any other genetic variation or mutation may be treated by the methods provided herein. Such disorders include, but are not limited to, Parkinson's disease, a toxicity-induced Parkinsonism, Alzheimer's disease, dementia, an autism spectrum disorder, susceptibility to viral infection such as HIV, and coloboma of the eye, heart defects, atresia of the choanae, retardation of growth and/or development, Genital and/or urinary abnormalities, and Ear abnormalities and deafness (CHARGE) syndrome. Autism spectrum disorders include Asperger syndrome, autism, PDD not otherwise specified, and Rett disorder.

Other known disorders related to CNV treatable by the methods described herein include, but are not limited to, 12q14 microdeletion syndrome, 15q13.3 microdeletion syndrome, 15q24 recurrent microdeletion syndrome, 16p11.2-p12.2 microdeletion syndrome, 17q21.3 microdeletion syndrome, 1p36 microdeletion syndrome, 1q21.1 recurrent microdeletion, 1q21.1 recurrent microduplication, 1q21.1 susceptibility locus for Thrombocytopenia-Absent Radius (TAR) syndrome, 22q11 deletion syndrome (Velocardiofacial/DiGeorge syndrome), 22q11 duplication syndrome, 22q11.2 distal deletion syndrome, 22q13 deletion syndrome (Phelan-Mcdermid syndrome), 2p15-16.1 microdeletion syndrome, 2q33.1 deletion syndrome, 2q37 monosomy, 3q29 microdeletion syndrome, 3q29 microduplication syndrome, 6p deletion syndrome, 7q11.23 duplication syndrome, 8p23.1 deletion syndrome, 9q subtelomeric deletion syndrome, Adult-onset autosomal dominant leukodystrophy (ADLD), Angelman syndrome (Type 1), Angelman syndrome (Type 2), ATR-16 syndrome, AZFa, AZFb, AZFb+AZFc, AZFc, Cat-Eye Syndrome (Type I), Charcot-Marie-Tooth syndrome type 1A (CMT1A), Cri du Chat Syndrome (5p deletion), Early-onset Alzheimer disease with cerebral amyloid angiopathy, Familial Adenomatous Polyposis, Hereditary Liability to Pressure Palsies (HNPP), Leri-Weill dyschondrostosis (LWD)-SHOX deletion, Miller-Dieker syndrome (MDS), NF1-microdeletion syndrome, Pelizaeus-Merzbacher disease, Potocki-Lupski syndrome (17p11.2 duplication syndrome), Potocki-Shaffer syndrome, Prader-Willi syndrome (Type 1), Prader-Willi Syndrome (Type 2), RCAD (renal cysts and diabetes), Rubinstein-Taybi Syndrome, Smith-Magenis Syndrome, Sotos syndrome, Split hand/foot malformation 1 (SHFM1), Steroid sulphatase deficiency (STS), WAGR 11p13 deletion syndrome, Williams-Beuren Syndrome (WBS), Wolf-Hirschhorn Syndrome, and Xq28 (MECP2) duplication.

In some embodiments, a subject with the genetic variation of interest has been diagnosed with a disorder or predisposition to a disorder associated with protein aggregation. Such disorders include, but are not limited to, Alzheimer's disease, Parkinson's disease, dementia, autism spectrum disorders, susceptibility to viral infection, diffuse Lewy body disease or any other Lewy body disorder or synucleinopathy, corticobasal degeneration, encephalitis lethargica, multiple system atrophy, pantothenate kinase-associated neurodegeneration (Hallervorden-Spatz syndrome), progressive supranuclear palsy, vascular Parkinsonism, Wilson disease, hereditary pancreatitis, glomerulonephritis, human systemic lupus erythematosus, paraneoplastic syndrome, frontotemporal dementia with Parkinsonism chromosome 17, Huntington's disease, spinocerebellar ataxias, amytropic lateral sclerosis, and Creutzfeldt-Jakob disease.

In some embodiments, the disorder is Parkinson's disease (PD) or a PD-related disease. PD-related diseases include diseases, conditions, symptoms or susceptibilities to diseases, conditions or symptoms, that involve, directly or indirectly, neurodegeneration including but not limited to the following: Alzheimer's disease, amyotrophic lateral sclerosis (ALS), Alpers' disease, Batten disease, Cockayne syndrome, corticobasal ganglionic degeneration, Huntington's disease, Lewy body disease, Pick's disease, motor neuron disease, multiple system atrophy, olivopontocerebellar atrophy, Parkinson's disease, postpoliomyelitis syndrome, prion diseases, progressive supranuclear palsy, Rett syndrome, Shy-Drager syndrome and tuberous sclerosis. Certain PD-related diseases are neurodegenerative diseases that affect neurons in the brain. A PD-related disease may be e.g. a condition that is a risk factor for developing PD, or may be a condition for which PD is a risk factor, or both.

The agents described herein can be administered in a variety of different ways. The therapeutic agents, identified by the screening methods described herein, may be incorporated into a variety of formulations for therapeutic administration by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds may be achieved in various ways, including intracranial, oral, buccal, rectal, parenteral, intraperitoneal, intravenous, intramuscular, topical, subcutaneous, subdermal, intradermal, transdermal, intrathecal, nasal, intracheal, etc., administration. The active agent may be systemic after administration or may be localized by the use of regional administration, intramural administration, or use of an implant that acts to retain the active dose at the site of implantation. For example, the agent may be intracranially administered using, e.g., an osmotic pump and microcatheter or other neurosurgical device to deliver therapeutic agents to selected regions of the brain under singular, repeated or chronic delivery regimens. In some embodiments, an agent can cross and or even readily pass through the blood-brain barrier, which permits, e.g., oral, parenteral or intravenous administration. Alternatively, the agent can be modified or otherwise altered so that it can cross or be transported across the blood brain barrier. Many strategies known in the art are available for molecules crossing the blood-brain barrier, including but not limited to, increasing the hydrophobic nature of a molecule; introducing the molecule as a conjugate to a carrier, such as transferring, targeted to a receptor in the blood-brain barrier, or to docosahexaenoic acid etc. In another embodiment, an agent is administered via the standard procedure of drilling a small hole in the skull to administer the agent. In another embodiment, the molecule can be administered intracranially or, for example, intraventricularly. In another embodiment, osmotic disruption of the blood-brain barrier can be used to effect delivery of agent to the brain (Nilayer et al., Proc. Natl. Acad. Sci. USA 92:9829-9833 (1995)). In yet another embodiment, an agent can be administered in a liposome targeted to the blood-brain barrier. Administration of pharmaceutical agents in liposomes is known (see Langer, Science 249:1527-1533 (1990); Treat et al., in Liposomes in the Therapy of infectious Disease and Cancer, Lopez-Berestein and Fidler (eds.), Liss, New York, pp. 317-327 and 353-365 (1989). All of such methods are envisioned herein.

Therapeutic agents may include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation may include other carriers, adjuvants, or non-toxic, nontherapeutic, nonimmunogenic stabilizers, excipients and the like. The compositions may also include additional substances to approximate physiological conditions, such as pH adjusting and buffering agents, toxicity adjusting agents, wetting agents, and detergents.

Further guidance regarding formulations that are suitable for various types of administration may be found in Remington's Pharmaceutical Sciences, Mace Publishing Company, Philadelphia, Pa., 17th ed. (1985). For a brief review of methods for drug delivery, see, Langer, Science 249:1527-1533 (1990).

In one embodiment, the agents are useful for modulating α-synuclein. Agents that can modulate α-synuclein can be selected from but not limited to those presented in Table 1. In certain embodiments modulation can include but not be limited to altered fibrillation, folding, ubiquitination, trafficking, synaptic targeting, lysosomal storage, expression, subcellular compartmentalization, and lipid-interactions.

TABLE 1

| Compounds that modulate α-synuclein function | | |
| --- | --- | --- |
| apomorphine | cefamandole sodium | fisetin |
| pyrogallol | cephaloridine | luteolin |
| 1,4-naphthoquinone | myricetin | fustin |
| cisplatin | 6,2',3'-trihydroxyflavone | epicatechin gallate |
| isoproterenol | 5,7,3',4',5'-pentahydroxyflavone | catechin |
| pyrogallin | 7,3',4',5'-tetrahydroxyflavone | alizarin |
| cianidanol | (5,6,7,4'-tetrahydroxyflavone) | tannic acid |
| sulfasalazine | baicalein | eriodyctol |
| quinalizarin | eriodictyol | carboplatin |
| benserazide | 7,3',4'-trihydroxyisoflavone | purpurogallin-4-carboxylic acid |
| hexachlorophene | epigallocatechin gallate | koparin |
| pyrvinium pamoate | quercetin | 2,3,4-trihydroxy-4'-ethexybenzophenone |
| dobutamine | gossypetin (3,5,7,8,3',4'-hexahydroxyflavone) | baeomycesic acid |
| methyl-dopa | 2',3'-dihydroxyflavone | hamtoxylin |
| curcumin | 3',4'-dihydroxyflavone | iriginol hexaaceatate |
| berberine chloride | 5,6-dihydroxy-7-methoxyflavone | 4-acetoxyphenol |
| daidzein | baicalein-7-methyl ether | theaflavin monogallate |
| merbromin | Levodopa (L-Dopa) | theaflavin digallate |
| norepinephrine | DOPAC | stictic acid |
| dopamine hydrochloride | homogentisic acid | purpurogallin |
| carbidopa | 6-hydroxydopamine | 2,5-dihydroxy-3,4-dimethoxy-4'-ethoxybenzophenone |
| ethylnorepinephrine hydrochloride | epinephrine | promethazine hydrochloride |
| tannic acid | 3,4-dihydroxycinnamic acid | oxidopamine hydrochloride |
| elaidyphosphocholine | 2,3-dihydroxynaphthalene | pyrantel pamoate |
| hydroquinone | 3,4-dihydroxybenzoic acid | elaidylphosphocholine |
| chlorophyllide Cu complex Na salt | 3,4,5-trihydroxybenzoic acid | amphotericin B |
| methyldopa | 1,2,3-trihydroxybenzoic acid | gallic acid |
| isoproterenol hydrochloride | gallate (gallic acid) | fumarprotocetraric acid |

TABLE 1-continued

Compounds that modulate α-synuclein function

| | | |
|---|---|---|
| benserazide hydrochloride | benzoquinone | theaflavin |
| dopamine | catechol | haematoxylin pentaacetate |
| dobutamine hydrochloride | rifampicin | 4-methoxydalbergione |
| thyroid hormone | rosmarinic acid | epigallocatechin-3-monogallate |
| purpurin | baicalin | rolitetracycline |
| Sodium beta-nicotinamide adenine dinucleotide phosphate | tanshinones I and II | 7,3'-dimethoxyflavone |
| lansoprazole | emodin | liquiritigenin dimethyl ether |
| dyclonine hydrochloride | procyanidin B4 | catechin pentaacetate |
| pramoxine hydrochloride | resveratrol | apigenin |
| azobenzene | rutin | 3,4-dedesmethyl-5-deshydroxy-3'-ethoxyscleroin |

The agents identified by the subject methods can be administered for prophylactic and/or therapeutic treatments. Toxicity and therapeutic efficacy of the active ingredient may be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are used in some embodiments.

The data obtained from cell culture and/or animal studies may be used in formulating a range of dosages for humans. The dosage of the active ingredient typically lines within a range of circulating concentrations that include the ED50 with low toxicity. The dosage may vary within this range depending upon the dosage form employed and the route of administration utilized.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The effective amount of a therapeutic agent to be given to a particular patient will depend on a variety of factors, several of which will be different from patient to patient. A competent clinician will be able to determine an effective amount of a therapeutic agent to administer to a patient. Dosage of the agent will depend on the treatment, route of administration, the nature of the therapeutics, sensitivity of the patient to the therapeutics, etc. Utilizing LD50 animal data, and other information, a clinician can determine the maximum safe dose for an individual, depending on the route of administration. Utilizing ordinary skill, the competent clinician will be able to optimize the dosage of a particular therapeutic composition in the course of routine clinical trials. The compositions can be administered to the subject in a series of more than one administration. For therapeutic compositions, regular periodic administration will sometimes be required, or may be desirable. Therapeutic regimens will vary with the agent, e.g., some agents may be taken for extended periods of time on a daily or semi-daily basis, while more selective agents may be administered for more defined time courses, e.g., one, two three or more days, one or more weeks, one or more months, etc., taken daily, semi-daily, semi-weekly, weekly, etc.

A pharmaceutically or therapeutically effective amount of the agent is delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. For purposes of the present method, generally a therapeutic amount may be in the range of about 0.001 mg/kg to about 100 mg/kg body weight, in at least one dose. The subject may be administered in as many doses as is required to reduce and/or alleviate the signs, symptoms, or causes of the disorder in question, or bring about any other desired alteration of a biological system.

Creation of Cell Lines from Induced Pluripotent Stem Cells Specific to Parkinson's Disease and Parkinson's-Like Disease Overview:

Because most available therapies for Parkinson's disease or related Parkinson's-like diseases are only symptomatic and lead to dose-limiting side-effects over time, there is a great need for the development of new and safe therapies to halt or even reverse disease progression.

The methods and cell lines disclosed herein are now described with respect to Parkinson's disease and Parkinson's-like disease, though one of skill in the art will appreciate that the methods of generating and screening cell lines described herein are generally applicable to all diseases and disorders involving CNV and other genetic variations.

To date, several different genes have been identified that are related to Parkinson's disease (Farrer, M. J. Genetics of Parkinson disease: paradigm shifts and future prospects. *Nat Rev Genet.* 7, 306-18 (2006). Several of these have provided major insights into proteins and pathways that are likely to be important for sporadic Parkinson's disease. A fundamental insightful observation came from the discovery that overexpression of the normal SNCA gene in familial cases of Parkinson's disease due to SNCA duplications or triplications leads to many features of PD (Singleton, A. B. et al. alpha-Synuclein locus triplication causes Parkinson's disease. *Science* 302, 841 (2003); Chartier-Harlin, M. C. et al. Alpha-synuclein locus duplication as a cause of familial Parkinson's disease. *Lancet* 364, 1167-9 (2004)). In humans, normal α-synuclein, when overexpressed can induce many of the clinical and pathological features of Parkinson's disease.

Using the methods described herein, human iPSCs may be generated from patients with Parkinson's disease, for example due to a triplication of the SNCA gene or due to a mutation in the LRRK2 gene or due to any other genetic variation/mutation relevant to Parkinson's disease or related Parkinson's-like diseases. The iPSCs are differentiated into cell types of interest known to be affected in Parkinson's disease or Parkinson's disease. These cells can be central or peripheral cells; can be neuronal or glial; can be autonomic or sympathetic; or can be for example dopaminergic neurons, serotonergic neurons, cholinergic neurons, GABAergic neurons, glutamatergic neurons, or peptidergic, neurons.

Generation of a Bank of iPSCs from Humans with Parkinson's Disease or Parkinson's Related Disease:

In some embodiments, the first step will be to create and expand a cell bank of iPSC lines from adult patients with specific genetic forms of Parkinson's disease, from adult patients with idiopathic Parkinson's disease, from adult patients presenting with atypical Parkinson's disease (Parkinson's-like disease) and from age-matched, gender-matched healthy control subjects. Patients with specific genetic variations may have copy number variations or mutations in the genes that encode α-synuclein (PARK1), or in the gene that encodes parkin (PARKA), or in the gene that encodes PINK 1 (PARK6), or in the gene that encodes LRRK2 (PARK5). Standard protocols as disclosed herein will be used to isolate somatic cells, for example dermal fibroblasts, from the patients, and dedifferentiate/reprogram them in to iPSC cell lines. In some embodiments a retroviral or lentiviral method is used for reprogramming. In other embodiments a method free of viral reprogramming factors is used.

Differentiation of the Parkinson's Disease-Specific iPSCs into Cellular Populations Involved in Parkinson's Disease and Parkinson's-Related Disease:

Following the creation, expansion, and maintenance of a bank of Parkinson's disease patient-specific iPSC cells (along with controls), the iPSCs can be differentiated to adopt a cell fate of interest, typically a cell known to be affected during the natural progression of Parkinson's disease or related diseases. For example, the iPSCs can be differentiated to be central or peripheral cells; neuronal or glial; autonomic or sympathetic; for example dopaminergic neurons, serotonergic neurons, cholinergic neurons, GABAergic neurons, glutamatergic neurons, or peptidergic, neurons. Exemplary cell types include but are not limited to neuronal and/or glial populations known to be affected in Parkinson's disease and Parkinson's related diseases such as olfactory bulb neurons; glial cells such as microglia and oligodendrocytes; cholinergic neurons such as those of the nucleus basalis of Meynert; neuronal populations of the spinal cord, for example IML neurons; peripheral autonomic nervous system cells, for example superior sympathetic cervical ganglia; neuronal populations in heart, bladder, gut, and other organs known to be affected in Parkinson's disease; cardiac cells with extrinsic and intrinsic autonomic innervation; brainstem nuclei such as pigmented nuclei; or brainstem catecholaminergic and serotonergic nuclei.

Characterization of Differentiated Cell Lines:

In some embodiments, the iPSC line is differentiated to adopt a midbrain dopaminergic cell fate. Objective measures of the dopaminergic phenotype will be examined and include tyrosine hydroxylase positivity, and the ability of the cells to synthesize and release dopamine. Additionally, neurophysiologic characteristics of dopaminergic neurons will be examined as will the development of a neurodegenerative phenotype (in vitro) reminiscent of Parkinson's disease.

Use of Parkinson's Disease-Specific Differentiated iPSC Lines for Assessing Disease Mechanisms and Screening for Therapeutic Agents Useful for Treatment of Parkinson's Disease and Parkinson's-Like Diseases:

In some embodiments, the cell lines and cell populations described herein are used to study the mechanism of Parkinson's disease or related diseases. In some embodiments, the differentiated patient-specific cells are compared to one or more control cells. In some embodiments, a toxicant, such as, MPTP/MPP+, 6-OHDA, rotenone, a mitochondrial toxin, or paraquat, or other such agents is applied to examine the cellular response of the patient-specific cell line. In some embodiments, the agent or condition produces cytotoxicity, oxidative stress, cell damage, cell degeneration, cell dysfunction, apoptosis, or mitochondrial dysfunction. Exemplary toxins include 1-methyl-4-phenyl-1,2,3,6-tetrahydropyridine (MPTP) and structurally related compounds, for example, rotenone and paraquat. Additionally, the toxin may be a toxin or metabolite that interferes with Complex I respiration in a cell's electron transport chain. MPTP structurally resembles a number of known environmental agents, including well-known herbicides such as paraquat (Di Monte, D., et al., Comparative Studies on the Mechanisms of Paraquat and 1-methyl-4-phenylpyridine (MPP+) Cytotoxicity, Biochem. Biophys. Res. Commun., 137:303-09 (1986)) and garden insecticides/fish toxins, such as rotenone (McNaught, K. S., et al., Effects of Isoquinoline Derivatives Structurally Related to 1-methyl-4-phenyl-1,2,3,6-tetrahydropyridine (MPTP) on Mitochondrial Respiration, Biochem. Pharmacol, 51:1503-11 (1996)) that have been shown to induce dopamine cell degeneration (Brooks, A. I., et al., Paraquat Elicited Neurobehavioral Syndrome Caused by Dopaminergic Neuron Loss, Brain Res., 823:1-10 (1999)). MPTP is a lipophillic molecule that rapidly enters the brain and is taken-up into glial cells by a number of mechanisms including monoamine (Brooks W J, et al., Astrocytes as a Primary Locus for the Conversion MPTP into MPP+, J. Neural. Transm. 76:1-12 (1989)) and glutamate (Hazell A S, et al., 1-Methyl-4-phenyl-1,2,3,6-tetrahydropyridine (MPTP) Decreases Glutamate Uptake in Cultured Astrocytes, J. Neurochem. 68:2216-19 (1997)) transporters or pH-dependent antiporters (Kopin I J, Features of the Dopaminergic Neurotoxin MPTP, Ann NY Acad. Sci. 648:96-04 (1992)). Once in glial cells, MPTP is metabolized by the enzyme MAOB to the unstable 1-methyl-4-phenyl-2,3-dihydropyridium (MPP+) which then rehydrogenates or deprotonates to generate MPTP or the corresponding pyridium species, MPP+, respectively. MPP+ is then released from glia and taken up by neuronal dopamine transporters where it interferes with Complex I respiration in the electron transport chain (Nicklas W J, et al., MPTP, MPP+ and Mitochondrial Function, Life Sci. 40:721-29 (1987)). MPP+ also binds to neuromelanin which is believed to contribute to its neurotoxicity (D'Amato R J, et al., Selectivity of the Parkinsonian Neurotoxin MPTP: Toxic Metabolite MPP+Binds to Neuromelanin, Science 231:987-89 (1986)). The toxicity of MPTP is determined by the response of glial cells following drug intoxication (Smeyne M, et al., Strain-Dependent Susceptibility to MPTP and MPP+-Induced Parkinsonism is Determined by Glia, Glia 74:73-80 (2001)). This is supported by numerous in vitro studies (Di Monte D A, et al., Production and Disposition of 1-methyl-4-phenylpyridinium in Primary Cultures of Mouse Astrocytes, Glia 5:48-55 (1992)). The cells of the present method and the toxicant are contacted, for example at 37° Celsius, for a predetermined amount of time, after which cells in the biological sample are observed and analyzed as discussed above.

In the present methods which use agents or conditions, the effect of the agent or condition is assessed by monitoring one or more output parameters such as, for example, changes in ATP production, LDH release, activated caspase levels, and expression of alpha-synuclein. The result is an analysis whereby the effect of an agent or condition on a family of parameters permits the identification of pathways and molecules therein affected by the disorder. The effect may be assessed by measuring the degree of change relative to the absence of the agent or condition or, alternatively, relative to contacting a control cell obtained from a subject who does not have a diagnosis of a disorder of interest with the agent or condition. Pathways of interest include the dopamine or other neurotransmitter metabolism pathways, the O-glycosylation pathway, the caspase activation and other apoptotic pathways, signal transduction relating to Lewy bodies, mitochondrial function, ubiquitination, proteasome function/degradation, lysosome function/degradation, and/or endoplasmic reticular stress.

Human induced pluripotent stem cell (human iPSC) lines from patients with Parkinson's disease due to a genetic basis such as a triplication of the α-synuclein (SNCA) gene, or a homozygous mutation of the LRRK2 gene, once differentiated can recapitulate key molecular aspects of neural degeneration associated with Parkinson's disease in vitro, including α-synuclein-positive inclusions and neuritic pathology. In other embodiment, human iPSC lines from individual presenting with idiopathic forms of Parkinson's disease can establish disease mechanisms of relevance to disease progression and useful for screening for agents that are disease modifying and provide tools for diagnosis of sporadic Parkinson's disease.

In some embodiments the compounds listed in Table 1 can be screened for effects in various differentiated Parkinson's disease or related disease-specific iPSC lines.

The cell lines can provide an entirely new experimental pre-clinical model of Parkinson's disease characterized by, for example, synuclein mis-folding and/or aggregation derived from humans with genetic Parkinson's disease to study cellular phenotypes and disease mechanisms unique to Parkinson's disease. The model can be also be used to screen for new agents that slow or block progression of disease.

The following examples are put forth so as to provide those of ordinary skill in the art with a complete disclosure and description of how to make and use the subject methods, and are not intended to limit the scope of what is regarded as the invention.

EXAMPLES

Example 1

Experimental Procedures

The following experimental procedures are utilized in the subsequent examples.

Patient Selection:

Potential patient with familial/genetic or sporadic/idiopathic forms of Parkinson's disease (typical or atypical) and healthy volunteers were informed of the study through poster advertising and referrals through patient advocacy and disease focus organizations (Parkinson's Institute). Potential donors were screened for men and women between the ages of 18 and 75 that had the familial or sporadic/idiopathic forms Parkinson's disease. The individuals in Table 2 were identified for participation in the study. Participants were informed about the nature and purpose of the study and its implications and appropriately consented. After informed consent was obtained, subjects underwent a skin punch biopsy. This tissue was utilized for the studies for creation of cell lines.

TABLE 2

Patients identified for participation in study

| Cell Line | Derivation Date | Sex | Age | Phenotype/comment |
|---|---|---|---|---|
| HUF1 | Oct. 31, 2007 | M | 28 | Healthy control |
| HUF2 | Nov. 28, 2007 | M | 62 | Sporadic/Idiopathic PD |
| HUF3 | Jan. 5, 2008 | F | 30 | Healthy control |
| HUF4 | Aug. 5, 2008 | M | 42 | Familial PD; SNCA triplication (Iowa Kindred) |
| HUF5 | Aug. 11, 2008 | F | 46 | Unaffected sibling to HUF4 |
| HUF6 | Sep. 16, 2008 | F | 60 | Familial PD; LRRK2, G2019S, homozygous |
| HUF7 | Sep. 18, 2008 | M | 35 | Offspring to HUF6 (asymptomatic); LRRK2, G2019S, heterozygous |
| — | — | M | 74 | Familial PD; LRRK2, G2019S, heterozygous |
| — | — | F | 18 | Juvenile-onset PD; PARKIN, Ex2del, c. 102delAG |
| — | — | F | 40 | Early-onset PD |
| — | — | F | 55 | Sporadic/Idiopathic PD |
| — | — | M | 49 | Sporadic/Idiopathic PD |
| — | — | M | 54 | Sporadic/Idiopathic PD |
| — | — | F | 49 | Sporadic/Idiopathic PD |
| — | — | F | 54 | Sporadic/Idiopathic PD |

Two living (and possibility the only remaining) patients with Parkinson's disease secondary to documented triplication of the SNCA gene have been identified; both are members of the Iowa kindred (Singleton, A. B. et al. alpha-synuclein locus triplication causes Parkinson's disease. *Science* 302, 841 (2003); Wszolek, Z. K. et al. Rapidly progressive autosomal dominant parkinsonism and dementia with pallido-ponto-nigral degeneration. *Ann Neurol* 32, 312-20 (1992)). The HUF-4 line was created from one individual with the SNCA gene triplication.

Participants were informed about the nature and purpose of the study and its implications and appropriately consented.

Primary Cell Derivation and Culture:

After informed consent was obtained, primary Human dermal fibroblasts (HDF) from the medial arm dermus were obtained by first cleaning the region with an alcohol swab and injecting 2-3 ml of 1% lidocaine with 1:100,000 diluted epinephrine. Then, a 4 mm dermal specimen was removed with a core punch biopsy instrument and placed in sterile PBS, while the skin defect was closed with a 4-0 nylon suture and covered with a double antibiotic ointment bandage. Sutures were removed after 2 weeks. The skin tissue biopsy was washed in $Ca^{2+}$ and $Mg^{2+}$ free Dulbecco PBS (Invitrogen, Carlsbad, Calif.) and minced into small pieces before being seeded onto gelatin coated 6-well cell culture flasks (Corning, Acton, Mass.) containing DMEM/F12 supplemented with 100 IU/ml penicillin, 100 μg/ml streptomycin (Invitrogen), 10% FBS (DMEM/FBS culture media) and cultured at 37° C. in 5% $CO_2$. A minimal amount of culture media was used to promote tissue attachment to the gelatin-coated surface (1 ml of culture media per well). The media was brought up to 4 ml per well once the skin fragments attached and the media was changed every 2 days. Once fibroblasts began to migrate out, the attached biopsy fragments and any connected epithelial cells were removed and the fibroblasts were cultured to 80-90% confluence (FIG. 1). This primary culture was passaged through brief exposure to 0.15% trypsin-EDTA (Invitrogen, Grand Island, N.Y.) and seeded into four gelatin-coated 175 cm cell culture flasks with fresh DMEM-F12/FBS culture media. These somatic cells were cultured until they reached 90% confluence and subsequently frozen in DMEM/FBS culture media supplemented with 10% dimethyyl sulphoxide (DMSO, Sigma, St. Louis, Mo.) in aliquots of one million cells per cryovial. These somatic cells were thawed as required for reprogramming/dedifferentiation studies. As such, a bank of somatic cells were created from the donors listed in Table 2.

hESC and iPSC Maintenance:

To maintain and expand human embryonic stem cells (hESC) and induced pluripotent stem cell (iPSC) pluripotency in vitro, colonies were co-cultured with irradiated mouse embryonic fibroblasts (MEF) in 6-well plates or 10 cm dishes with hESC medium (76% DMEM-F12 medium supplemented with 20% knock-out serum replacer (KOSR), 1% NEAA, 1% 100×BME, 1% 100×L-glutamine, 1% 100× Penicillin-Streptomycin and 10 ng/ml bFGF). MEFs were prepared by sacrificing pregnant CF-1 mice (Charles River Laboratories), transferring fetuses to fresh PBS and repeating until blood was absent. The fetal heads and visceral organs were mechanically removed and the remaining carcass was transferred between PBS dishes until blood was removed, finishing in a dish containing 5 ml Trypsin. Carcass tissue was cut into small pieces using scalpels, transferred from individual fetuses to a 15 ml centrifuge tube and incubated in 5% $CO_2$ at 37° C. for 20 min. 10 ml feeder medium was added to neutralize the Trypsin and the solution was pipetted up and down with a 25 ml stripper pipette. The sample was centrifuged at 1000 RPM for 5 min, the supernatant was aspirated and the sample was resuspended in 10 ml fresh feeder medium—repeated until solution was devoid of blood. Cells were plated at one fetus per T175 gelatin coated flasks with 30 ml feeder medium and incubated in 5% $CO_2$ at 37° C. Cells were subsequently passaged every 2-6 days (when flasks neared 90% confluency) for 5-7 passages, irradiated with 3000 rad gamma waves and then frozen down in DMSO.

iPSC Generation using Retroviruses:

For retroviral production, 293FT cells were cultured in T175 flasks to ~90% confluence on the day of transfection. For each 293FT T175 flask, two premixes were prepared; (1) 10 ug VSVG, 15 ug Δ8.9, 10 ug retroviral vectors carrying Oct3/4, Sox2, Klf4 and c-Myc in 10 ml Opti-MEM; and (2) 120 ul Lipofectamine in 5 ml Opti-MEM. The two premix solutions were incubated for 5 min at room temperature and then mixed gently by hand inversion. The resulting mix was then allowed to sit for 20 min at room temperature. The 293FT cells were treated with the resulting 15 ml mix and incubated in 5% $CO_2$ at 37° C. for 6 hours, after which the transfection mixture was replaced with 18 ml of 10% FBS in DMEM+Glutamax and incubated in 5% $CO_2$ at 37° C. for 72 hours. The supernatant was harvested in 50 ml conical tubes and spun down at 2000 rpm for 5 minutes. The supernatant was filtered through a Millex-HV 0.45 filter unit and stored briefly for concentrating. To concentrate the virus, 30 ml fresh viral supernatant was concentrated 100× by centrifugation at 17,100 rpm for 2:20 hours at 20° C. in a Beckman Coulter Optima L-80XP Ultracentrifuge and re-suspended in 300 ul of 10% FBS/DMEM. 100× viral stock was stored at −80° C.

Target fibroblasts were prepared at $1\times10^5$ cells per well of a 6-well plate. The four prepared viral supernatants were mixed to the appropriate concentrations with fresh MEF medium and supplemented with 8 ng/mL polyprene and cultured with the cells overnight. The next day, cells were washed once with medium and incubated overnight with MEF medium to allow recovery from the infection. The retroviral infection was repeated. After the second infection round, cells were rinsed three times with PBS, replaced with MEF medium and incubated for three days with media changes every day. On the third day, infected cells were trypsinized and seeded at $1\times10^5$ cells/10 cm dish with fresh MEF medium and x CF1 MEFs. Eight days after infection, the medium was changed to hESC medium. Starting on day 19 post-infection, potential iPSC colonies were identified based on morphology and manually picked and transferred to either 12- or 24-well plates with xCF1 MEF feeders in iPSC medium.

In certain experiments iPSCs were generated from fibroblasts with the use of three factors, Oct4, Sox2, and Klf4. The generation of the HUF6 line, from a patient carrying a LRRK2 homozygous mutation, the iPSCs were generated using these three 3 factors.

iPSC Generation using Lentiviruses:

For plasmid construction, the coding regions of Oct4, Sox2, Nanog, Lin28, Klf4 and cMyc were amplified by RT-PCR from the cDNA of H9 hESCs (Thomson et al., Science, 1998); the coding regions of SV40 Large T and hTERT were amplified from pBABE-puro-SV40 LT vector (plasmid 13970, T. Roberts) and pBABE-hygro-hTERT vector (plasmid 1773, R. Weinberg), respectively, purchased from Addgene. The genes were initially cloned into pENTR™/D-TOPO® (Invitrogen) and then, together with Ubiquitin C promoter, recombined with p2K7-bsd lentiviral vector (Suter et al., 2006) by the Gateway (LR plus clonase enzyme mix) system (Invitrogen). Additionally, lentiviral vectors created by J. Thompson and colleagues, pSin-EF2-Oct4-Pur (Plasmid 16579, J. Thompson), pSin-EF2-Sox2-Pur (Plasmid 16577), pSin-EF2-Nanog-Pur (Plasmid 16578), and pSin-EF2-Lin28-Pur (Plasmid 16580), were purchased from Addgene.

For lentiviral production and infection, 293FT cells (Invitrogen), maintained in MEF medium supplemented with 0.5 mg/ml Geneticin (Invitrogen), were allowed to expand until reaching 90-95% confluence. One day prior to infection, fresh antibiotic-free culture medium were added to the cells. For each 175-cm flask, 293FT cells were transfected with 10 μg of plasmid DNA carrying the transgenes along with 10 μg VSVG and 15 μg Δ8.9 of the packaging plasmids. The transfection was facilitated by 120 ul of Lipofectamine 2000 (Invitrogen) and 15 ml opti-MEM (Invitrogen) for 6 hours and then replaced with 17 ml of fresh MEF medium without antibiotics. After 3 days, the viral supernatant was collected by spinning and passing through a Millex-HV 0.45 um filter unit (Millipore). The viral supernatants were concentrated by ultracentrifugation (Optima L-80XP, Beckman Coulter) at 17,100 RPM for 2.2 hours at 20° C.

For lentiviral infection and iPSC generation, one day before transduction, human fibroblast cells were seeded at $8\times10^4$ cells per well of a 6-well plate. Next day, equal volumes (0.5 ml) of fresh supernatants, supplemented with 8 ng/ml polyprene, carrying each of the six lentiviruses were mixed and added to the growing fibroblasts. 24 hours later, the viral supernatants were washed with PBS and replaced with fresh MEF medium. 5 days post-transduction, the cells were resuspended with trypsin, counted, and seeded, at $5\times10^4$ cells/dish, onto 10-cm dishes pre-plated with irradiated CF1 feeders. After overnight incubation, the MEF medium was replaced with hESC medium, and thereafter, the medium was changed every other day or every day, if required. hESC-like colonies started to appear among hundreds of backgrounds colonies around 14-20 days posttransductions. The colonies were manually picked and transferred to 24-well plates pre-plated with CF1 feeders. Colonies that continued to expand and maintained their hESC-like morphology were further passaged into larger vessels; whereas, those that failed to expand and/or exhibited early signs of differentiation were discarded. FIG. 2 illustrates the creation of the HUF1 line (see Table 2) using a lentiviral-mediated protocol and establishment of colonies.

iPSC Generation Using Non-Virally Mediated Direct Delivery of Reprogramming Proteins:

Plasmids are constructed by amplifying human ESC cDNA for Oct4, Sox2, Klf4, and c-Myc and cloned into pcDNA3.1/myc-HisA (Invitrogen) constructs. The protein extracts are prepared by transfecting HEK 293 cells using a reagent such as Lipofectamine. About 2 ug of plasmid DNA is transfected per about 4×10^5 cells and stably expressing cell lines are established by selection with an antibiotic such as with about 500 ug/ml neomycin (G418). To prepare protein extracts, cells are washed in PBS, centrifuged at about 400×g, and lysed in ~1 volume of cold lysis buffer (about 100 mM HEPES, about 50 mM NaCl, about 5 mM MgCl2, about 2 mM dithiothreitol, and protease inhibitors) for about 45 min on ice. Cells are sonicated on ice and lysates are sedimented at about 15,000 g for about 15 min at about 4° C. to pellet debris. Supernatant is then filtered through a ~0.2 um membrane, aliquoted, and snap-frozen on crushed dry ice.

For protein transduction, human fibroblasts are incubated with all four protein factors for about 8 hrs a week up to about 6 weeks and cultured in DMEM media supplemented with about 2 mM L-glutamine, about 1 mM beta-mercaptoethanol, ~1× non-essential amino acids, about 20% fetal bovine serum, about 1500 U/ml LIF. After ~6 weeks, cells are dissociated and transferred to inactivated mouse feeder cells and cultured with hESC media consistent of KO-DMEM, about 20% KSOR, about 2 mM L-glutamine, about 1 mM beta-mercaptoethanol, ~1× non-essential amino acids, about 16 ng/ml bFGF until iPSC colonies are formed.

Reverse Transcription, Pre-Amplification and RT-PCR:

RNA was purified using QIAGEN Quick Prep-Mini kit or cell sorting directly into the pre-amplification reaction mix. Samples were then reverse transcribed and pre-amplified with 5 ul CellsDirect 2× Reaction Mix, 10 ul Superscript III TR/Platinum Taq Mix (Invitrogen, CellsDirect One-Step qRT-PCR kit), 2.5 ul of 0.5× pooled primers and probes, 1.5 ul TE Buffer (QIAGEN) and 0.1 ul SUPERaseIn (Applied Biosystems). RT-PCR was performed in 20 ul volumes with 10 ul ABI 2× Reaction Mix (Applied Biosystems), 1 ul FAM probe, 1 ul VIC probe, 0.5-2 ul of pre-amplified sample, were mixed with water and amplified as follows: Pre-amp thermocycle: 95° C. for 10 min, 18 cycles of 95° C. for 15 seconds, 60° C. for 4 min, and then hold at 4° C.

Immunocytochemistry and Alkaline Phosphatase Staining:

Alkaline Phosphatase (AP) staining was performed with Vector® Red Alkaline Phosphatase Substrate Kit I (Vector Laboratories, CA), according to the manufacturer's protocol. For immunocytochemistry, cells were fixed in 4% paraformaldehyde/PBS for 10 minutes, washed twice with PBS, and blocked with 1-3% donkey, goat or chicken serum in PBS for 1 hour—all procedures were done at room temperature. For nuclear or intracellular staining, after fixation, the cells were permeabilized with 0.3% Triton-X100 for 30 minutes at room temperature. Subsequently, the primary antibodies were added to PBS and incubated for 1 hour at room temperature or overnight at 4° C. The cells were then washed with PBS before fluorescent-conjugated secondary antibodies were added and incubated for an hour at room temperature. Finally, the cells were rinsed with PBS three times and counter stained with DAPI. Stained samples were imaged directly on a LEICA inverted microscope or, if the samples were on coverslips, were mounted in PVA-DAVCO overnight and then imaged on an inverted confocal microscope. Primary antibodies and their dilutions were used as follows: Oct4 (diluted at 1:100, Santa Cruz), Sox2 (1:200, Millipore), SSEA1 (1:200, Millipore), SSEA4 (1:200, Millipore), TRA1-60 (1:200, Millipore), TRA1-81 (1:200, Millipore), Nanog (1:100, Abcam), α-Fetoprotein (1:200, Abcam), 131II Tubulin (1:200, Abcam), α-Smooth muscle actin (1:200, Abcam), Vasa (1:200, Abcam) Nestin (1:200, Santa Cruz), Doublecortin (1:200, Santa Cruz), Tyrosine hydroxylase (1:500, Pel-Freez Biologicals). Secondary antibodies were raised in either donkey, goat or rabbit with conjugates: Alexa 488-conjugated anti-rabbit IgG (1:500, Invitrogen), Alexa 594-conjugated anti-rabbit (1:500, Invitrogen), Alexa 647-conjugated anti-rabbit (1:500, Invitrogen), Alexa 488-conjugated anti-mouse IgM (1:500, Invitrogen) and Alexa 488 anti-mouse IgG (1:500, Invitrogen), FITC anti-Mouse conjugated, Cy3 anti-Rabbit, and Cy5 anti-Goat.

Directed Midbrain Dopaminergic Differentiation:

To direct differentiation of pluripotent cell colonies towards a midbrain dopaminergic cell fate, two or three hESC or iPSC colonies were mechanically harvested and gently dissected into 4-6 pieces per colony. Cells were then plated onto a 6 cm co-culture dish with irradiated MS-5 (xMS-5) stromal cells (MS-5 cells were expanded in MS-5 stromal cell culture medium: 455 ml alpha-MEM, 2 mM L-glutamine, 50 ml heat inactivated FBS, Pen-strep) and cultured for 16 days in Serum Replacement Media (15% KOSR in KO-DMEM), with media changes every two days. After 16 days, media was changed to N2+/+ (Progesterone 20 nM, Putrescine 100 uM, Sodium Selenite 30 nM, Insulin 5 ug/ml, Transferrin 0.1 mg/ml in DMEM-F12). At day 28, neural rosettes in the colonies were passaged through mechanical micro-dissection and transferred onto Poly/Laminin coated (15 ug/ml polyornithine, 1 ug/ml laminin) 6-well plates and cultured for one week in 200 ng/ml Sonic Hedgehog (SHH), 100 ng/ml Fibroblast Growth Factor 8 (FGF-8), 20 ng/ml Brain Derived Neurotrophic Factor (BDNF), and 0.2 mM Ascorbic Acid (AA) in N2+/+ media. On day 35, when cultures are approximately 80% confluent, colonies were passaged through digestion in $Ca^{2+}/Mg^{2+}$ free HBSS at room temperature for 1 hour and subsequent mechanical dissociation. Removed cell aggregates were centrifuged at 200 g for 5 minutes, resuspended and plated on Poly/Laminin coated dishes at $50\text{-}100\times10^3$ cells/$cm^2$ in N2+/+ media with the previously noted, day 28, growth factors. On day 42, differentiation was induced for 8 days through growth factor withdrawal by changing media to N2+/+ with 20 ng/ml BDNF, 20 ng/ml Glial Derived Neurotrophic Factor (GDNF), 1 ng/ml Transforming Growth Factor β3 (TGF-133), 1 mM Dibutyryl Cyclic Adenosine Monophosphate (cAMP) and 0.2 mM AA in N2+/+ media. On day 50, cell cultures were harvested for analysis.

Figure 3:
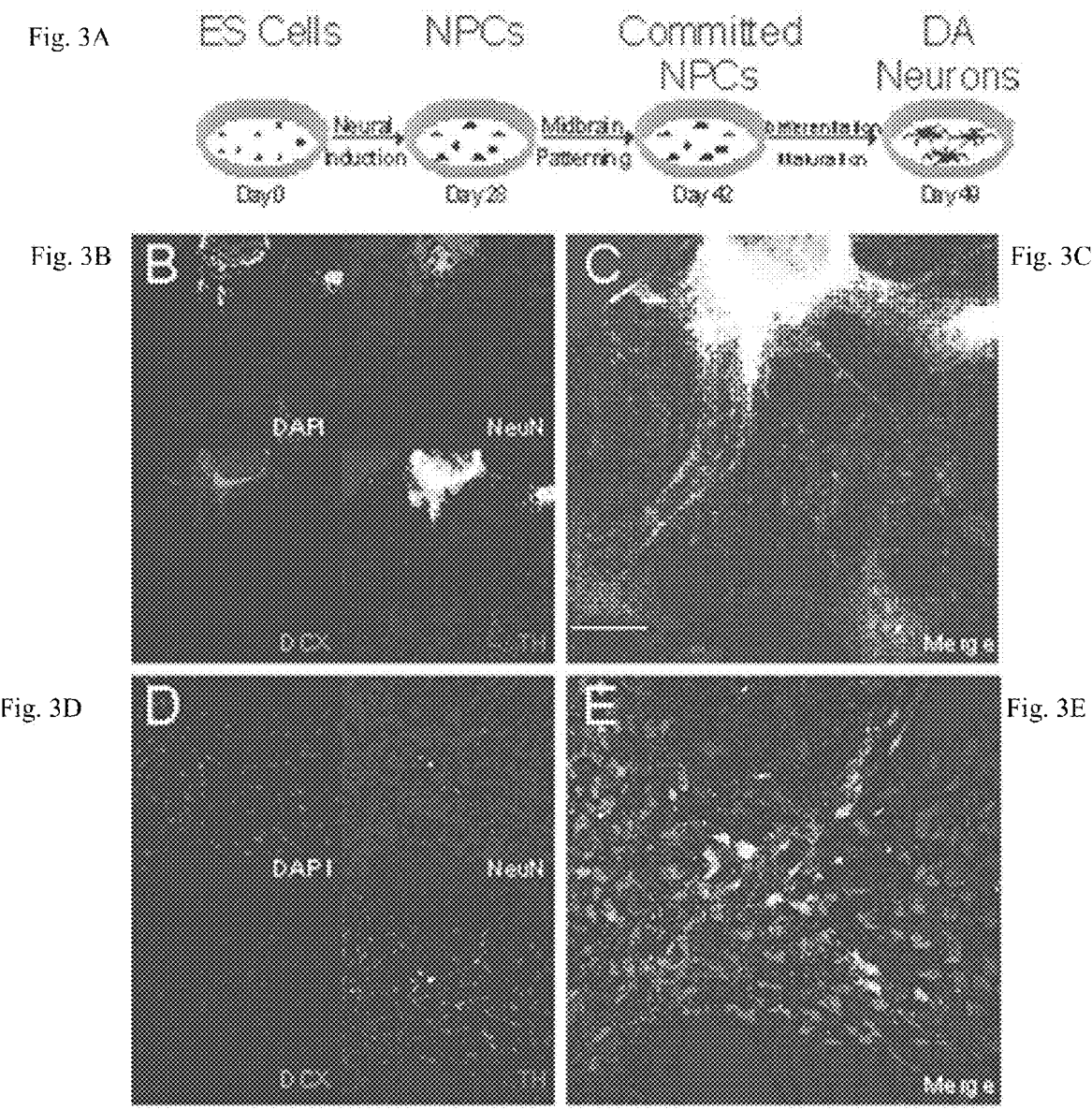
FIG. 3 illustrates hESCs subjected to 49 days of patterning and differentiation to generate cultures containing dopaminergic neurons.

Generation of ES-derived dopaminergic neurons is demonstrated in FIG. 3. Dopaminergic neuron production from the hESC H9 line is demonstrated by the accumulation of TH-positive, NeuN positive neurons. These neurons form fasciculated bundles of neurites that course between neuronal cell aggregates. This protocol and the like can be used to differentiate the newly generated hiPSC lines.

Phenotypes of the differentiated cells can be evaluated using immunofluorescent staining for markers associated with midbrain-specific dopaminergic neurons as well as other neuronal and glial cell subtypes. For example, multiple staining for generic neuronal and glial markers may provide information on the overall makeup of differentiated cell populations. Neuronal markers that may be used include Map2 (immature and mature neurons), type III beta tubulin (immature neuron), doublecortin (immature), and NeuN (mature). Glial markers that may be used include glial fibrillary acidic protein (astrocytes), S100-beta (astrocytes), NG2 (oligodendrocytes), and GalC (oligodendrocytes). The fraction of neurons exhibiting a midbrain-specific dopaminergic phenotype may be further evaluated by staining for tyrosine hydroxylase (TH) and evaluating cells for co-expression of midbrain-consistent markers such as TH, aromatic amino acid decarboxylase, Grk2, and absence of markers for non-midbrain neuronal subtypes such glutamate transporter, GAD or dopamine beta hydroxylase.

Human iPSCs from patients with genetic variations are compared to controls. The cells are tested for markers of (1) general cytotoxicity in cell viability assays, (2) apoptosis, (3) oxidative stress, and (4) mitochondrial function. These markers are to determine if there are differences in the survival and viability between cells SNCA triplication and controls. The cells are also tested for several parameters such as ATP, LDH release, and activated caspase levels using luminescent assays on a multi-well microplate luminometer. Furthermore, the expression of α-synuclein is assessed by qRT-PCR and immunohistochemistry to investigate α-synuclein pathology in this cellular model.

Alternatively, different feeder cells are used and/or the recombinant growth factors are modified to produce a neuronal dopaminergic phenotype (Yan, Y. et al. Directed differentiation of dopaminergic neuronal subtypes from human embryonic stem cells. *Stem Cells* 23, 781-90 (2005); Park, C. H. & Lee, S. H. Efficient generation of dopamine neurons from human embryonic stem cells. *Methods Mol Biol* 407, 311-22 (2007)). In another alternative, the differentiated cells are exposed to various toxicants known to induce neurodegeneration and cellular damage such as MPTP and paraquat.

Bisulfite Sequencing:

To determine methylation status, indicative of active transcription, bisulfite sequencing was performed on genomic DNA isolated from hESCs and iPSCs, grown on feeder-free media, with Methyl Easy Xceed Rapid DNA Bisulfite Modification Kit (Human Genetic Signatures, Sydney, New South Wales, Australia) per manufacturers directions. The promoter regions of Oct3/4 and Nanog were amplified by PCR, as described by Deb-Rinker at al. (Deb-Rinker et al., 2005). The PCR products were subcloned into pCR2.1 TOPO (Invitrogen), and twelve clones from each sample were analyzed by sequencing with M13 universal primer.

In Vitro Differentiation:

To investigate in vitro differentiation, cell culture medium was replaced with ~80% KO DMEM, 20% fetal bovine serum (FBS), 1% 100×L-glutamine, 1% 100× betamercaptoethanol (BME), 1% 100× non-essential amino acids (NEAA), and 1% 100× Penicillin-Streptomycin. After culturing for the desired time period, cells were either examined by immunocytochemistry or harvested for protein or RNA analysis.

In Vivo Teratoma Formation and Immunohistochemistry:

To determine iPSC potential to form all three germ layers in vivo, hESCs and iPSCs cells were harvested from 6-well or 10 cm plates through brief Collagenase IV treatment and transferred to 200 ul of hESC medium. The cells were either grafted subcutaneously behind the neck or in the hind limp muscles of female SCID mice (Charles River). After 8-10 weeks post-transplantation, grafts were dissected and fixed with 4% paraformaldehyde/PBS overnight. The tissues were then paraffin embedded, sectioned and stained with Masson's Trichrome, Mayer's Mucicarmine, Saffron O and Hematoxylin and Eosin.

Karyotyping:

To prepare the karyotyping metaphase spread, 10 μl/mL colcemid was added to the cell culture and incubate for up to 2 hours. The growth medium was removed and collected while the cells were rinsed with HBSS. Cells were treated with 2 mL trypsin and re-incubated at 37° C. for 5-7 min. The collected colcemid medium from the earlier step was re-applied to the cells to neutralize the trypsin and resuspend the cells. The resulting solution was centrifuged at 1000 RPM for 6 min and the supernatant was partially aspirated and resuspended in the native solution by flicking the tube. 5 drops of pre-warmed hypotonic solution were slowly added against the side, while flicking with a finger, until 1 ml had been added. Volume was then brought to 2 mL with hypotonic solution. The sample was incubated at 37° C. for 7 min and then centrifuged at 1000 RMP for 6 min. Medium was added to resuspend the cells. To fix the cells, 5 drops of fixative were slowly added against the side of the tube and the volume was brought to 2 mL with fixative. Cells were "reverse bubbled" to fully mix the cells and then the cells were left to fix for 30 min at room temperature. After fixing, the sample was centrifuged, aspirated, and resuspended with the finger as before. Any clumps were removed by vacuum from the side of tube, and 2 ml of fixative were added to the tube. Sample was then "reverse bubbled", let stand for 20 min at room temperature, and then centrifuged, aspirated, and resuspended with finger, as before. Sample was resuspended in 2 ml of fixative and then transferred onto pre-cleaned slides in ~100 ul drops, left to dry overnight, and then analyzed on a SKY microscope.

Characterization of Phenotype:

To characterize the differentiated cell lines, several assays will be used. Differentiated iPSCs will be examined for signs of spontaneous pathology starting with measures of dopaminergic cell abundance and survival (% dopaminergic neurons after differentiation) and general morphological attributes such as inclusion bodies, or dystrophic neurites. Markers which implicate selected mechanisms of pathology will also be evaluated including 1) apoptosis (TUNEL, caspase activation), 2) necrosis (CytoTox-Glo), 3) oxidative stress (glutathione, ROS and 4-HNE), 4) mitochondrial dysfunction (MitoExpress, ATP content); 5) Protein aggregation of α-synuclein will be assessed with antibodies against total, phosphorylated and nigrated α-synuclein to detect aggregates, inclusion bodies, and neuritic pathology. Cells from affected individuals will be compared to those from healthy controls.

Example 2

Derivation of Control Human Fibroblasts (HUF1 Line)

The HUF1 line was created from a healthy control volunteer. Similar to the techniques presented in Example 1, after informed consent was obtained, the patient's skin was cleaned with an alcohol swab, and a few milliliters of 1% lidocaine with epinephrine diluted 1:100,000 was injected into the skin to achieve local anesthesia. A 4 mm core punch biopsy instrument was used to remove a piece of skin and the specimen was placed on saline Patient participation lasted approximately 1 hour. The skin defect was closed with 4-0 nylon suture and a double antibiotic ointment covered bandaid was applied to the wound. Sutures were removed in 2 weeks. A primary somatic fibroblast cell culture was established from the skin biopsy. The skin tissue biopsy was washed in Ca and Mg free Dulbecco PBS (Invitrogen, Carlsbad, Calif.) and minced into small pieces. Tissue pieces were seeded onto gelatin coated 6-well cell culture flasks (Corning, Acton, Mass.) containing DMEM supplemented with 100 IU/ml penicillin, 100 µg/ml streptomycin (Invitrogen), 10% FBS (DMEM/FBS culture media) and cultured at 37 C in 5% CO2. A minimal amount of culture media was used to promote tissue attachment to the gelatin coated surface (1 ml of culture media per well). The media was brought up to 4 ml per well once the skin fragments attached and the media was changed every 2 days. Once fibroblasts began to grow, the attached biopsy fragments were removed and the fibroblasts were be cultured to confluence. This primary culture was passaged through brief exposure to 0.25% trypsin-EDTA (Invitrogen, Grand Island, N.Y.) and seeded into several new T175 cell culture flasks with fresh DMEM/FBS culture media. These somatic cells were cultured until they reached ~90% confluence and then frozen down at passage 1 in DMEM/FBS culture media supplemented with 10% dimethyyl sulphoxide (DMSO, Sigma, St. Louis, Mo.) in aliquots of one million cells per cryovial. These somatic cells were thawed as required for further reprogramming research. Manually dissected human skin biopsy fragments demonstrated attachment to a gelatin coated surface and primary human fibroblasts outgrowths formed over a 2 week period (see FIG. 3).

Lentiviral Transduction of Primary Human Fibroblasts FUGW UbC-GFP Lentiviral Supernatant Production:

A 90% confluent T175 of 293T cells (p13) were Lipofectamine 2000 transfected with 10 ug VSV-G, 15 ug Δ8.9 and 10 ug FUGW. Plasmids were premixed in 10 ml of Opti-MEM and 120 ul of Lipofectamine was premixed in 5 ml Opti-MEM. Following a 5 minute incubation at room temperature the plasmids and lipofectamine were mixed together and incubated a further 20 minutes at room temperature to allow DNA-lipofectamine complexes to form. Following this incubation the plasmid-lipofectamine mixture was gently laid over the 293T cells and incubated for 6 hours in a 37 C incubator. Following this transfection the mixture was replaced with 15 mls of DMEM+10% FBS and incubated for 3 days in the lentiviral room. Following the 3 day incubation the viral supernatant was spun down at 2000 rpm for 5 min and filtered through a 0.4 um Millex-HV filter unit and then used fresh.

Infection of Primary Human Fibroblasts (HUF1):

Primary human fibroblasts (p4) were transduced at 40-50% confluence on a 6 well plate. This level of confluence allowed for the determination of the post-transductional viability based on the ability of the cells to proliferate. 2 ml of four-fold dilute fresh supernatant was appropriately diluted in DMEM+10% FBS, mixed with polybrene to a final concentration of 8ug/ml and incubated with the HUF1 cells overnight at 37 C. Following overnight transduction the cells were washed twice in PBS and incubated for 3 days in DMEM+10% FBS in regular 37 C incubator. At the end of the 3 day incubation the cells were examined for GFP expression both by fluorescence microscopy and FACS analysis. Results are shown in FIG. 4.

Transduction of Primary Human Fibroblasts with Reprogramming Factors:

The cDNAs for the open reading frames (ORFs) of human LIN28, cMYC and KLF4 genes were obtained by direct PCR of human ES cell cDNA and after sequence verification, the cDNAs for each gene were cloned into a 2K7 lentiviral vector backbone (Ubiquitin C promoter), which was derived from a recombinant HIV-1-based, replication-defective vector, pLENTI-Block-iT-DEST (Invitrogen). The OCT4, SOX2 and NANOG lentiviral vectors were provided courtesy of Professor Jamie Thomson (pSIN vector backbone, EF1a promoter). These combination of the OCT4, SOX2, NANOG and LIN28 genes represent the Thomson reprogramming factors (Yu, Vodyanik et al. 2007). We also investigated if the addition of cMYC and KLF4 could increase the iPS reprogramming efficiency. The 293T cell line (Invitrogen) was used to produce transgene-expressing lentivirus supernatant which was used fresh. Lentiviral transductions of the human primary fibroblasts (HUF1, p2) were carried out with cells in attachment (~80% confluence/2 ml/well of 12-well gelatin-coated plate) using a equal mixture of the viral supernatants (2 ml total volume) in the presence of polybrene (8 µg/ml final concentration, Sigma). One HUF1 sample was transduced with just the Thomson reprogramming factors (OCT4, SOX2, NANOG and LIN28) and a second sample was transduced with the Thomson reprogramming factors plus cMYC and KLF4 (six factors total). Following overnight incubation with lentivirus, the human somatic cells were cultured for 72 hours and then trypsinized and transferred to gelatin coated T175 flasks. Cells were incubated in MEF conditioned embryonic stem (ES) cell media until the formation of iPS colonies with human embryonic stem cell morphology. MEF conditioned media was replaced every two days. For ES media DMEM/F12 culture media was supplemented with 0.1 mM non-essential amino acids, 1 mM L-glutamine, 0.1 mM B-mercaptoethanol, 8 ng/ml basic fibroblast growth factor (FGF) and 20% knock-out serum replacer (KSR).

Figure 5:
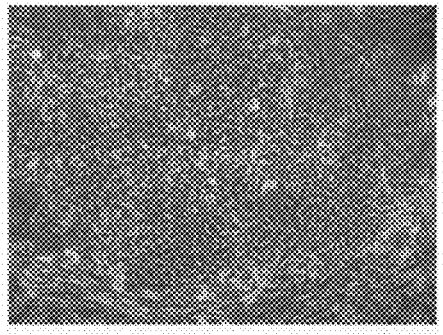
FIG. 5 illustrates the morphologies of the reprogrammed/dedifferentiated cell lines.
Figure 5:
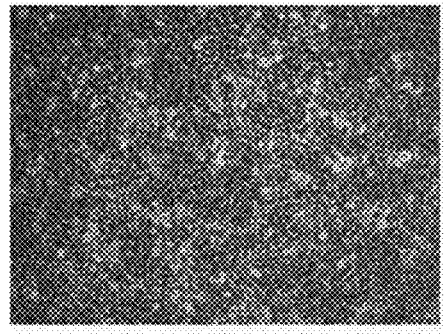
Figure 5:
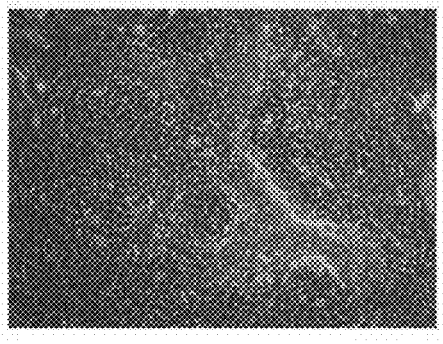
Figure 5:
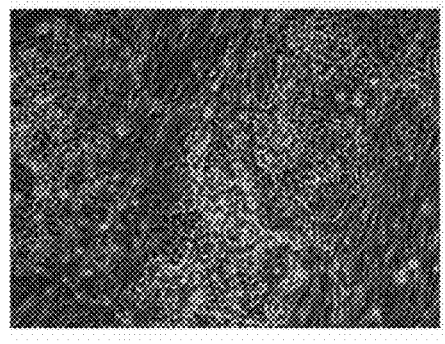
Figure 5:
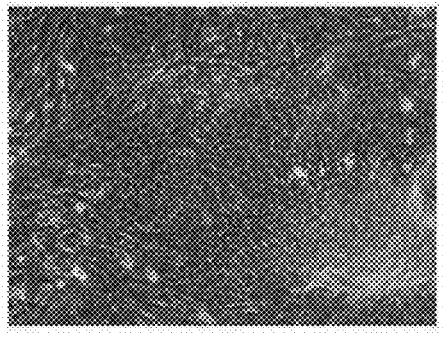
Figure 5:
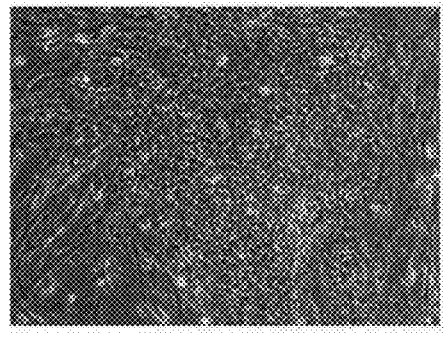
Figure 6:
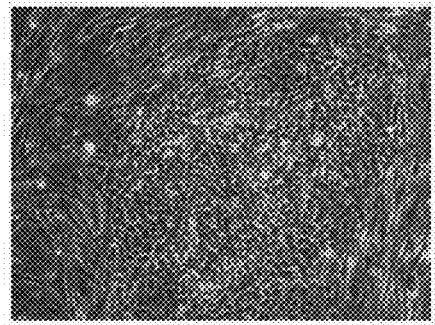
FIG. 6 illustrates the morphologies of the reprogrammed/dedifferentiated cell lines.
Figure 6:
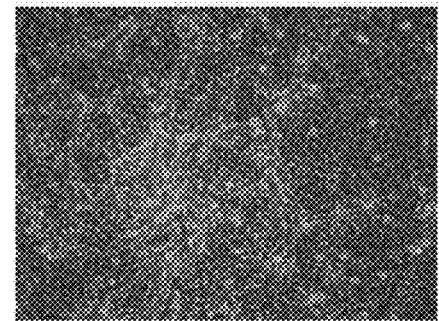
Figure 6:
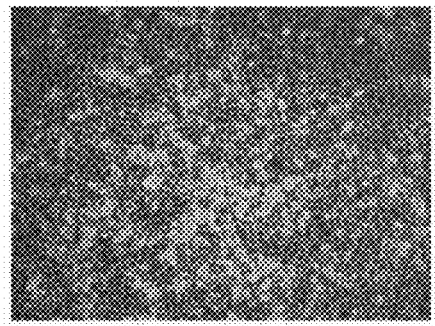
Figure 6:
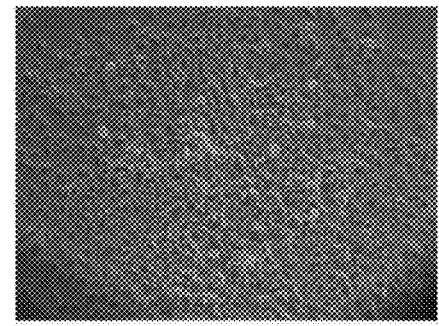
Figure 6:
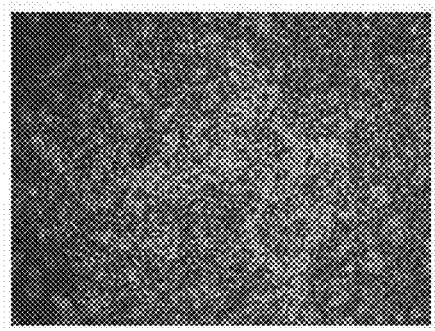
Figure 6:
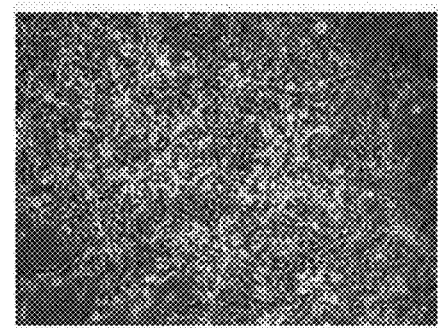
Figure 7:
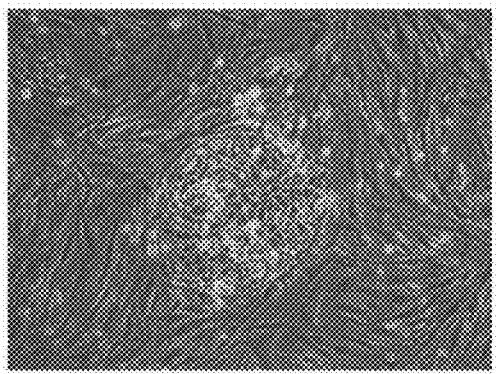
FIG. 7 illustrates the morphologies of the reprogrammed/dedifferentiated cell lines.
Figure 7:
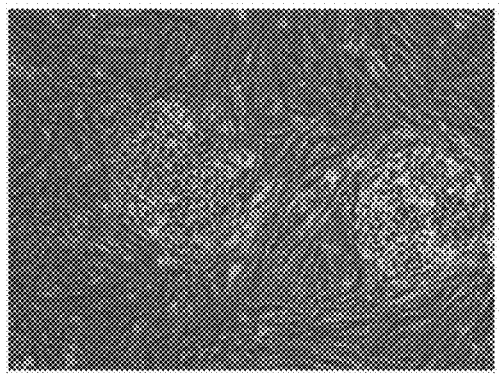
Figure 7:
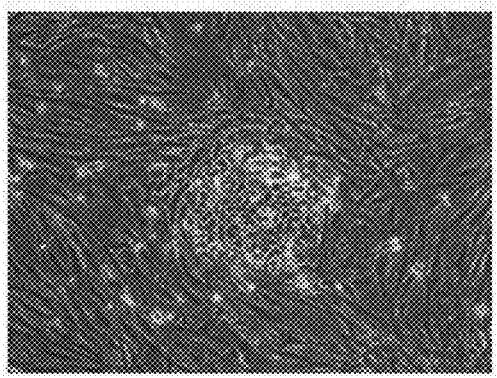
Figure 7:
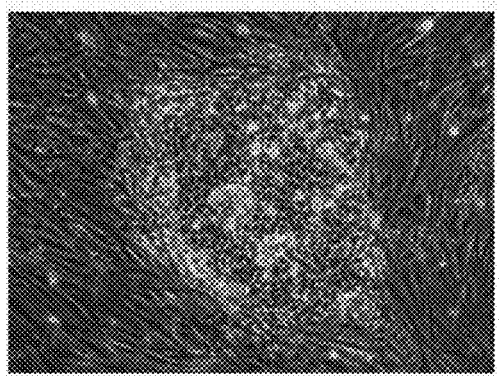

Results:

Colonies formed after 4 weeks; those with characteristics that resembled hESCs were manually dissected into small pieces and cultured on fresh MEFs, 8 from the Thomson factor transduced HUF1 cells and 8 from the Thomson factor+cMyc and Klf4 transduced HUF1 cells. Some colonies produced outgrowths and formed lines with characteristic morphology as shown in FIGS. 5-7.

Example 3

Derivation, Characterization and Differentiation of Human iPSCs from a Parkinson's Disease Patient with a Triplication of the SNCA Gene iPSC lines were generated from human fibroblasts of a patient (obtained by skin biopsy) with Parkinson's disease due to a SNCA triplication (HUF4 line) and his unaffected female sibling (HUF5 line), using a retroviral system with factors known to reprogram somatic cells, according to the methods of Example 1.

Figure 8:
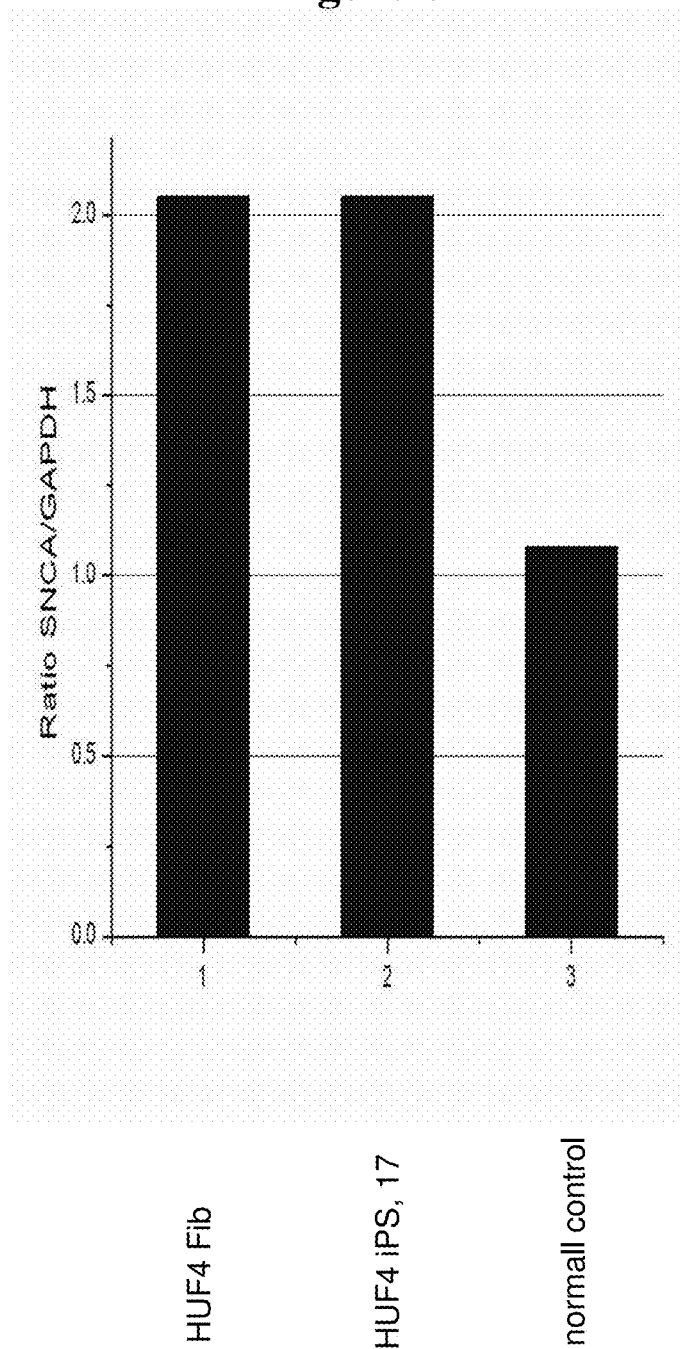
FIG. 8 illustrates gene dosage of Exon 3 of the SNCA gene and confirms SNCA triplication in the HUF4 iPSC clone 17 line, as assessed by qPCR.

FIG. 8 illustrates SNCA triplication as confirmed in HUF4 iPSC clone 17 line, by qPCR. Quantitative real-time PCR (qRT-PCR) analysis for the SNCA gene was performed using 40 ng of genomic DNA and SYBR® Green PCR Master Mix. Reactions were performed in triplicate, wherein each target region was co-amplified with an internal control (GAPDH) using the ABI 7000 RT-PCR system (Applied Biosystems). Primers used were:

```
SNCA Exon 3 forward primer
TGACAAATGTTGGAGGAGCA

SNCA Exon 3 reverse primer
CTGGGCTACTGCTGTCACAC

GAPDH forward primer
TGGGCTACACTGAGCACCAG

GAPDH reverse primer
GGGTGTCGCTGTTGAAGTCA
```

Gene copy number was determined with the standard curve method. The ratio of target gene compared to an internal control gene of 0.8-1.0 is equivalent to a normal copy number of 2 (alleles). A ratio of 1.8-2.2 is considered a copy number of 4 and is equivalent to a triplication of the target gene. FIG. 8 depicts the gene dosage SNCA Exon3

Figure 10:
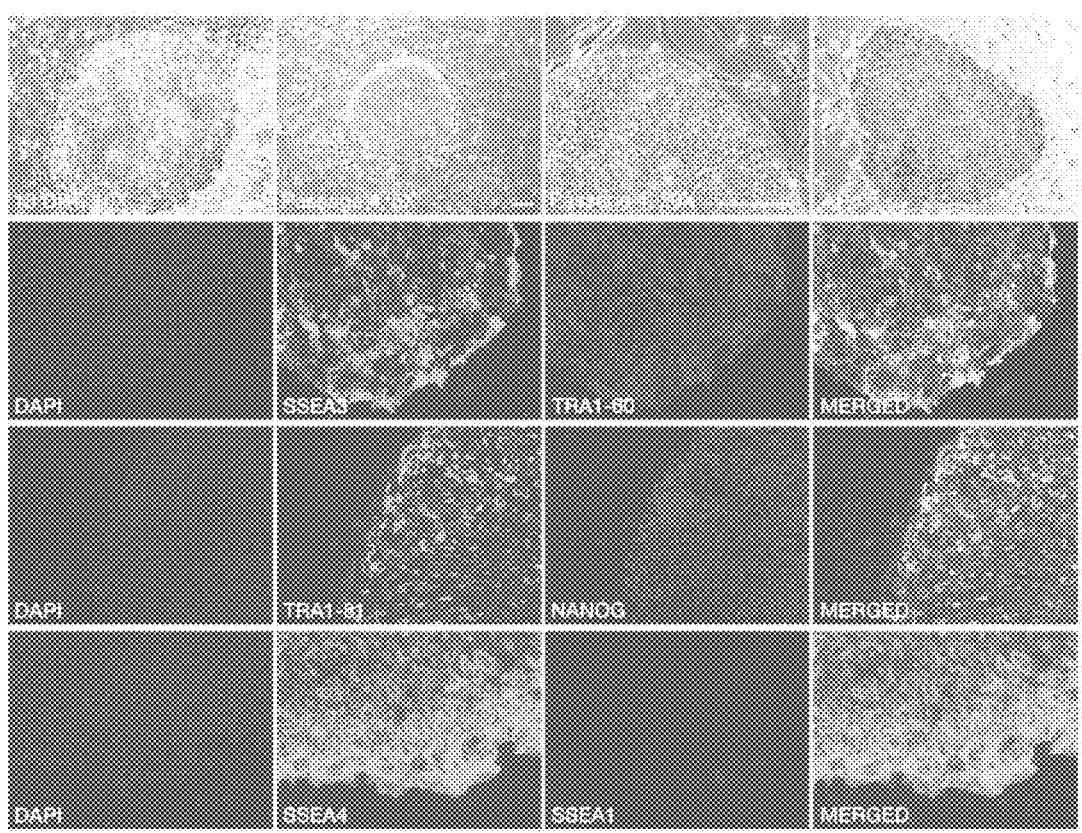
FIG. 10 illustrates HUF4 (clone 17) phase contrast images of morphology on MEF feeder layer at 10×, 5× and 20× (Panels 1-3), alkaline phosphatase staining (Panel 4), nuclear staining with DAPI and immunocytochemistry of pluripotency factors; SSEA, Tra1-60, TRA1-81, NANOG, SSEA4, and SSEA1.
Figure 11:
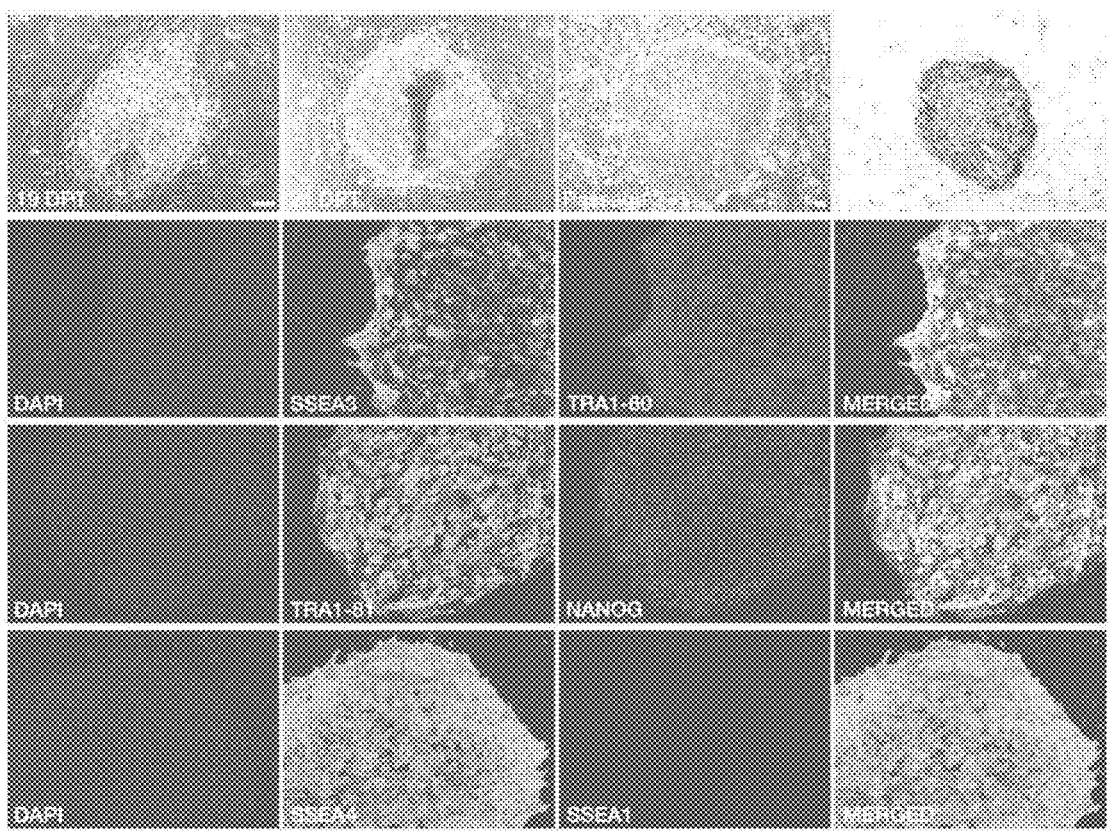
FIG. 11 illustrates HUF5 (clone 2) phase contrast images of morphology on MEF feeder layer at 10×, 5× and 20× (Panels 1-3), alkaline phosphatase staining (Panel 4), nuclear staining with DAPI and immunocytochemistry of pluripotency factors; SSEA, Tra1-60, TRA1-81, NANOG, SSEA4, and SSEA1.

FIG. 9 illustrates the untransduced fibroblasts used for the generation of the HUF4 and HUF5 lines. The HUF4 and HUF5 lines were stained and imaged to assess pluripotency. Pluripotency stains show successful reprogramming/dedifferentiation of the HUF4 clone 17 (FIG. 10) and HUF5 clone 2 (FIG. 11) lines.

Figure 12:
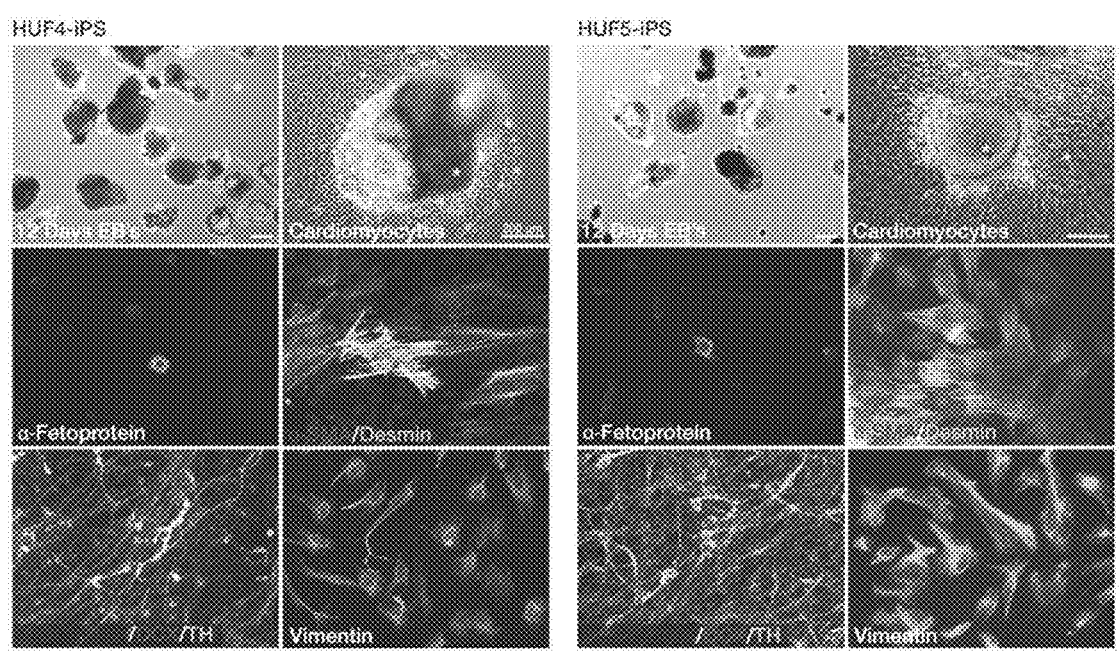
FIG. 12 illustrates in vitro differentiation of HUF4 (clone 17) (left panel) and HUF5 (clone 2) (right panel) to embryoid bodies, functional cardiac myocyte differentiation and the three germ layers; endoderm (α-Fetalprotien), mesoderm (α-SMA and Desmin) and ectoderm (β-III-Tubulin, DCX and TH).

To further assess pluripotency status of the cell lines, in vitro differentiation of the HUF4 clone 17 and HUF5 clone 2 lines were carried out. FIG. 12 illustrates that both HUF4 and HUF5 cells formed embryoid bodies, functional cardiac myocyte differentiation, and the three germ layers, as assessed by staining for germ layer-specific markers. Endoderm formation was assessed by staining for α-fetalprotein; mesoderm formation was assessed by staining for α-SMA and desmin; and ectoderm formation was assessed by staining for β-III-tubulin, doublecortin (DCX) and tyrosine hydroxylase (TH) (FIG. 12).

Figure 13:
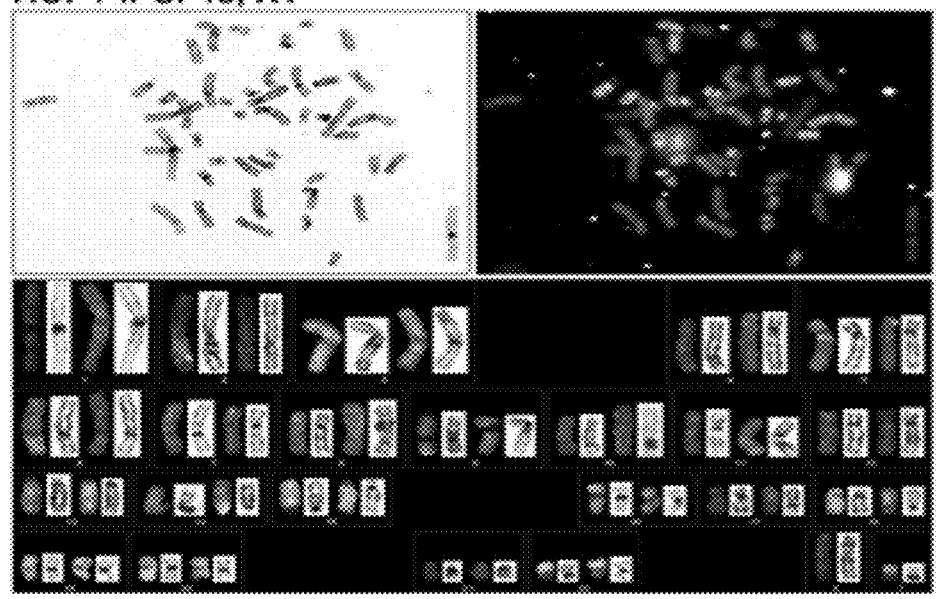
FIG. 13 illustrates a karyotype analysis of HUF4 (clone 17) and HUF5 (clone 2) derived iPSC lines. 20 replicates showed no translocations, triplications, or deletions.
Figure 13:
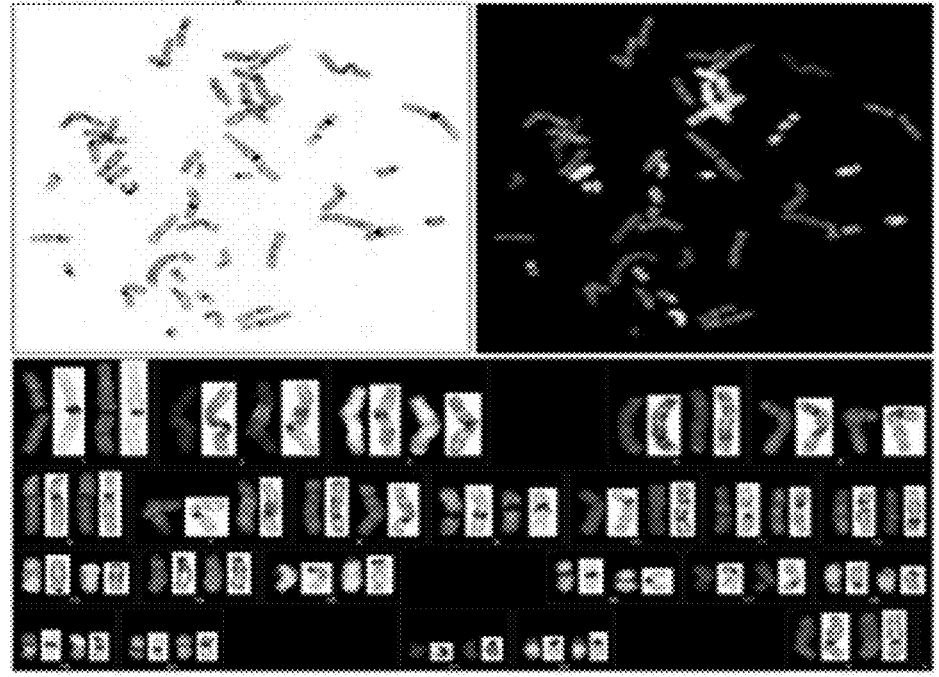

Karyotype analyses of the HUF4 clone 17 and HUF5 clone 2 lines were carried out to assess for any aberrant, macroscopic chromosomal abnormalities. The results of the analysis indicated no translocations, triplications, or deletions (FIG. 13).

Figure 14:
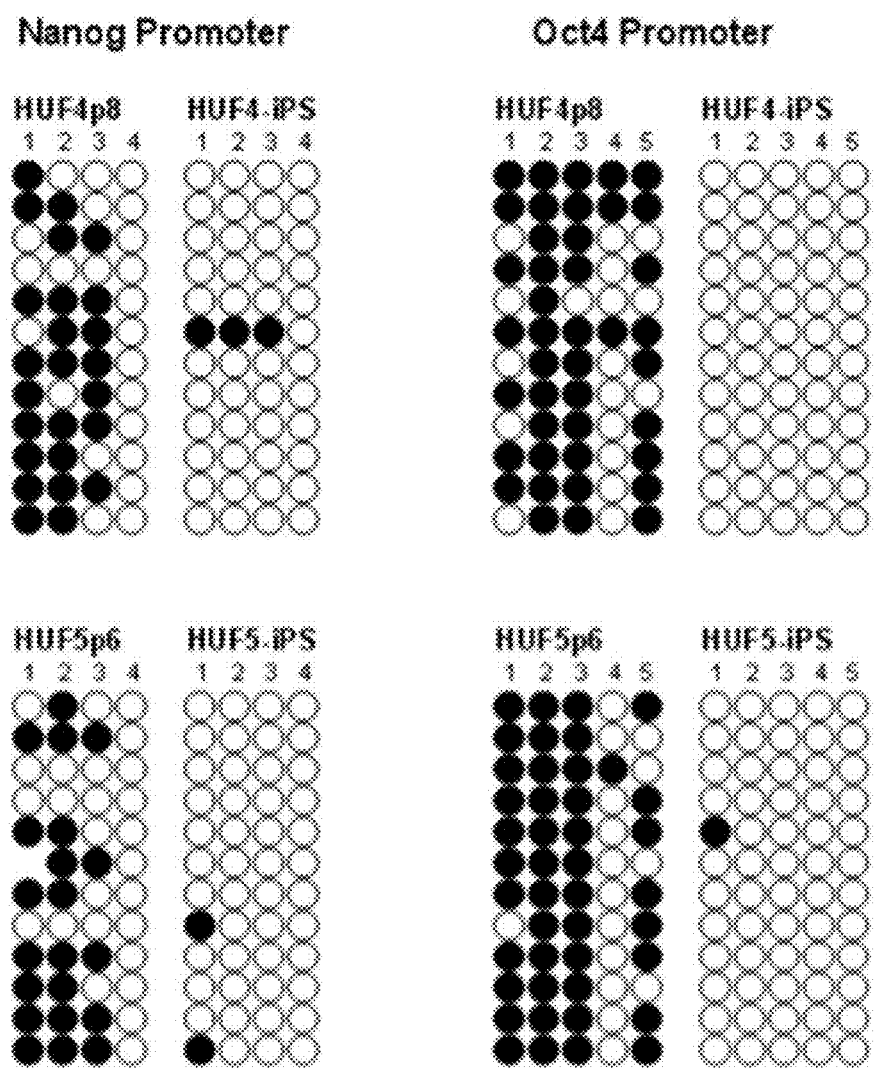
FIG. 14 illustrates the methylation status of Nanog and Oct4 promoters as determined by bisulfite sequencing in untransduced fibroblasts (HUF4 clone 17 p8 and HUF5 clone 2 p6) and pluripotent iPSC lines (HUF4-iPS and HUF5-iPS).

The methylation status of the Nanog and Oct4 promoters was determined by carrying out bisulfite sequencing, as described in the methods of Example 1. These two endogenous transcription factors are related to pluripotency. FIG. 14 shows the methylation status of the two lines at different stages.

Figure 15:
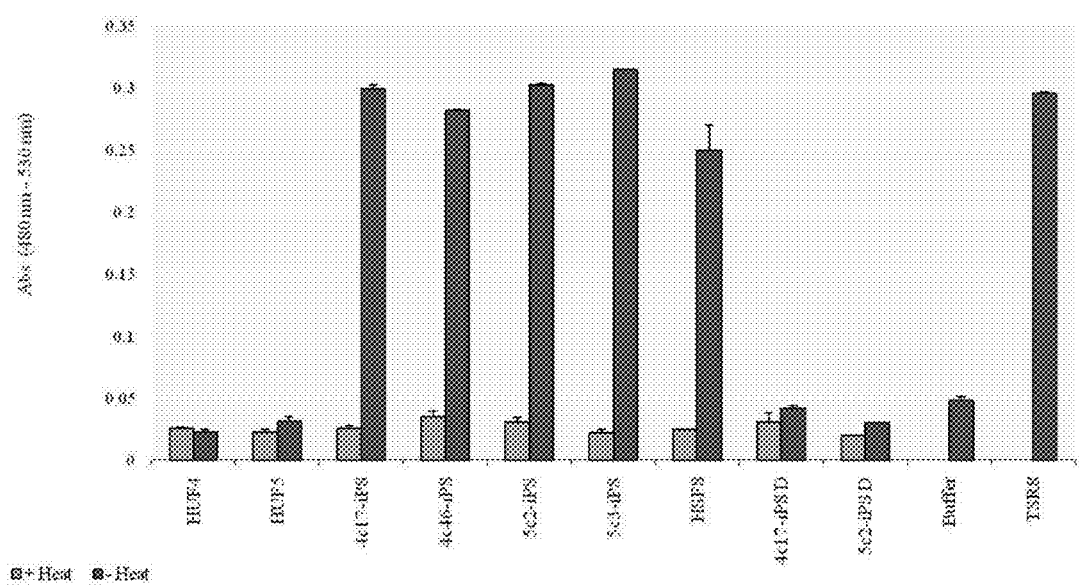
FIG. 15 illustrates the relative telomerase activity in: untransduced fibroblast lines (HUF4 and HUF5); pluripotent iPSC lines HUF4 (clones c17, c46) and HUF5 (clones c2 and c3); pluripotent hESC line HSF8; differentiated iPSC lines HUF4 (c17) and HUF5 (c2); negative buffer only control; and TSR8 positive control.

Relative telomerase activity was assessed in untransduced HUF4 and HUF5 cell lines, pluripotent iPSC lines, and pluripotent hESC lines, and differentiated iPSC lines HUF4 and HUF5. The results are presented in FIG. 15.

Figure 16:
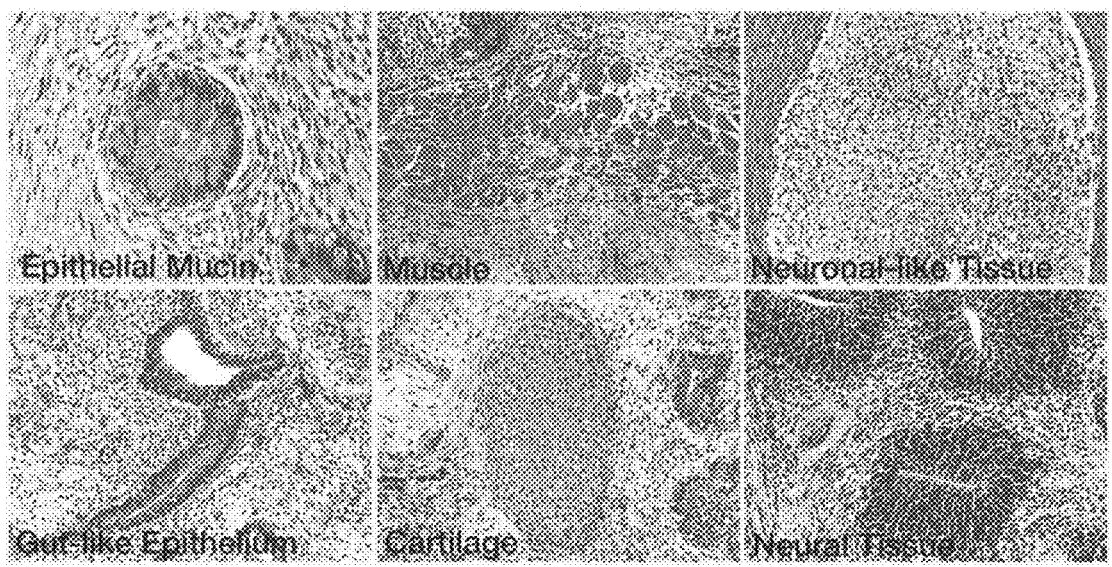
FIG. 16 illustrates HUF4 (clone 17) teratoma sectioning pathology. Formation of the endoderm is exemplified by the formation of the epithelial mucin and gut-like epithelium; formation of the mesoderm is exemplified by formation of the smooth muscle and cartilage; and formation of the ectoderm is exemplified by formation of neural tissue.
Figure 17:
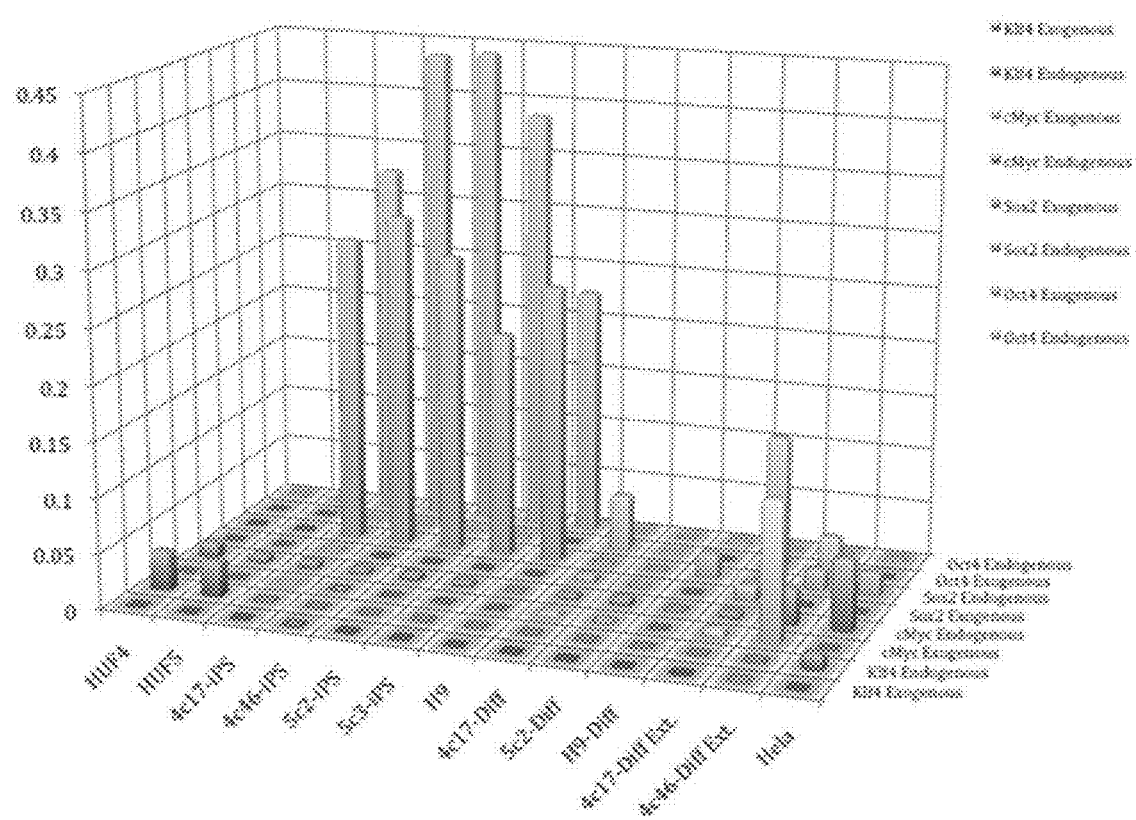
FIGS. 17-21 illustrate expression of endogenous and exogenous transcription factors following reprogramming in HUF4 and HUF 5 lines (parental, iPSCs, differentiated, different clones) as well as control H9 and Hela cells. Endogenous and exogenous expression of Oct4, Sox2, cMyc, and Klf4 expression are examined.
Figure 18:
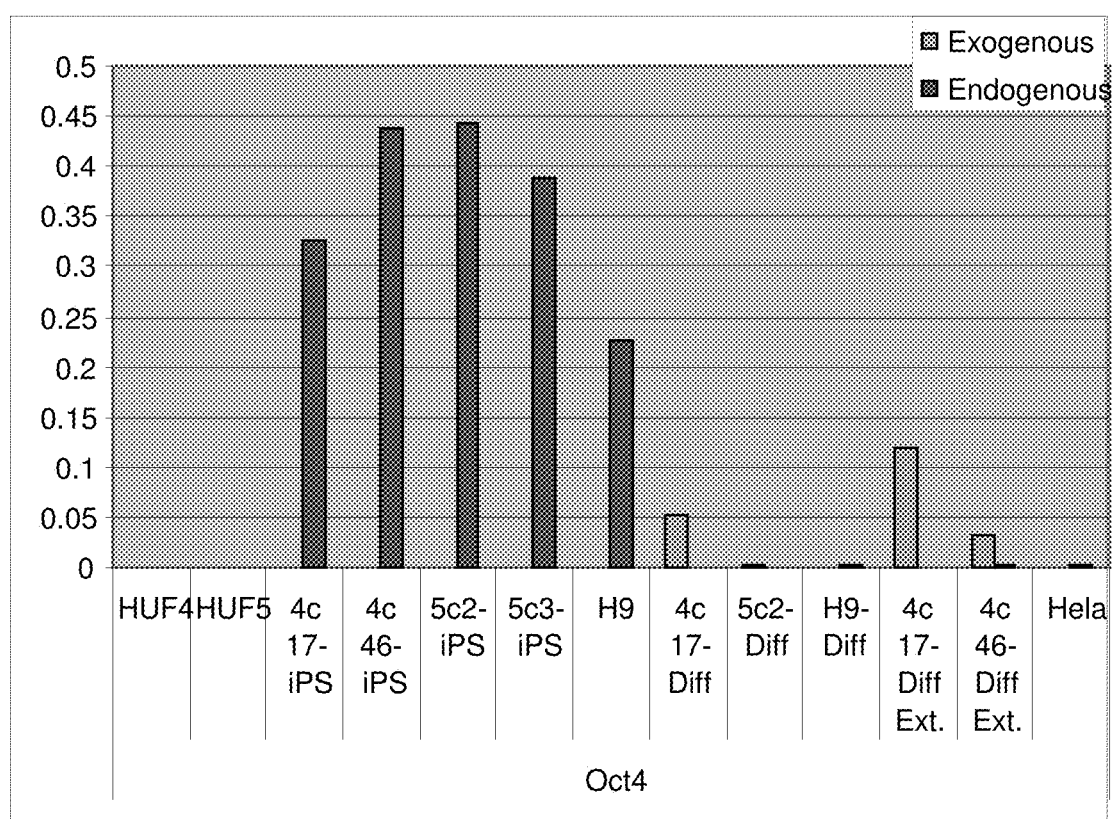
Figure 19:
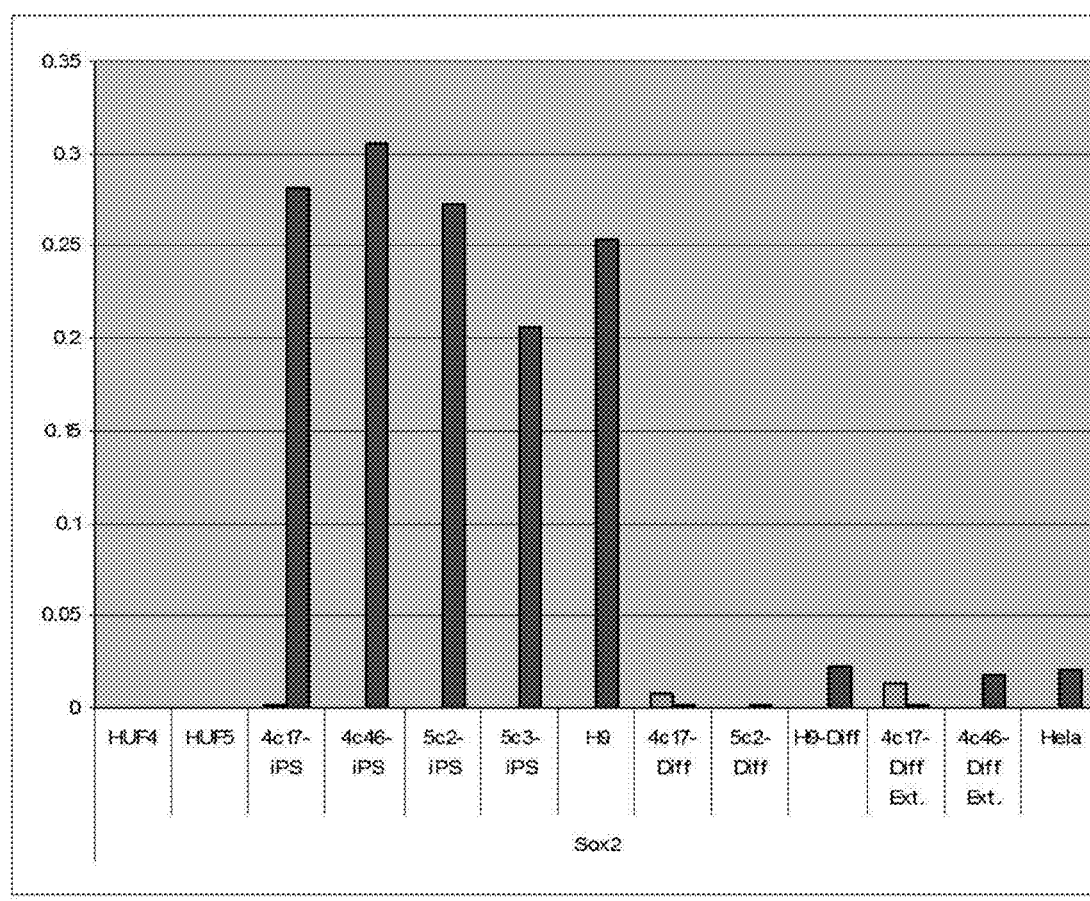
Figure 20:
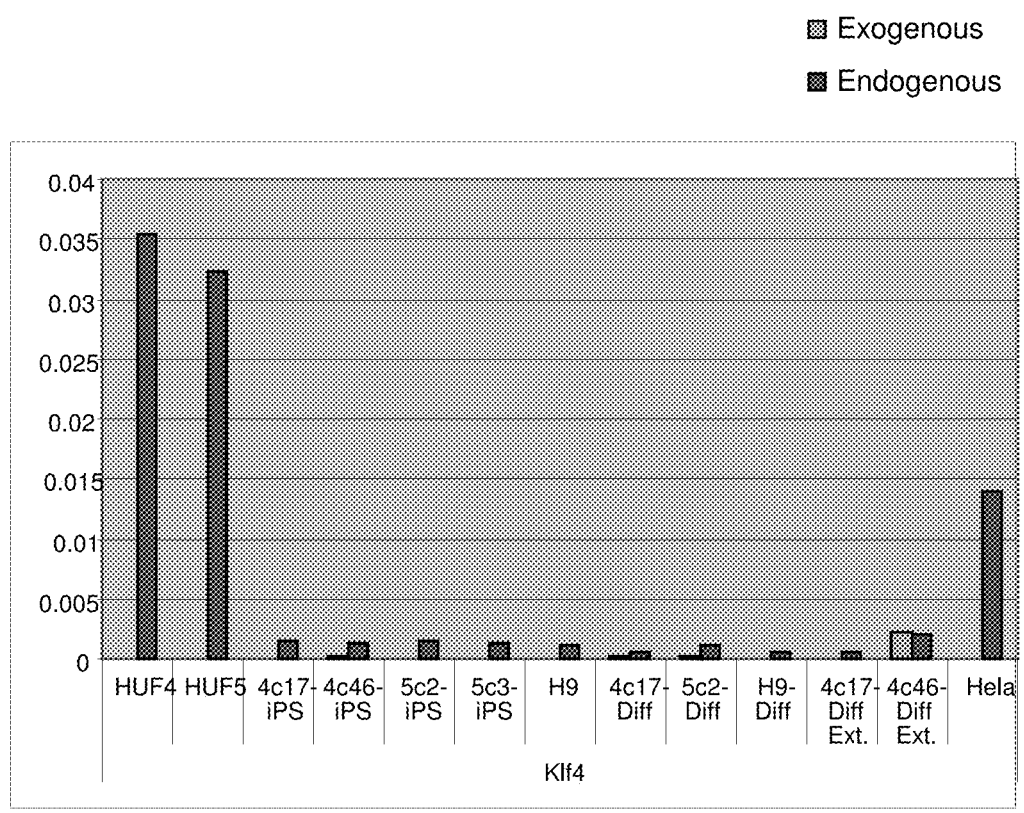
Figure 21:
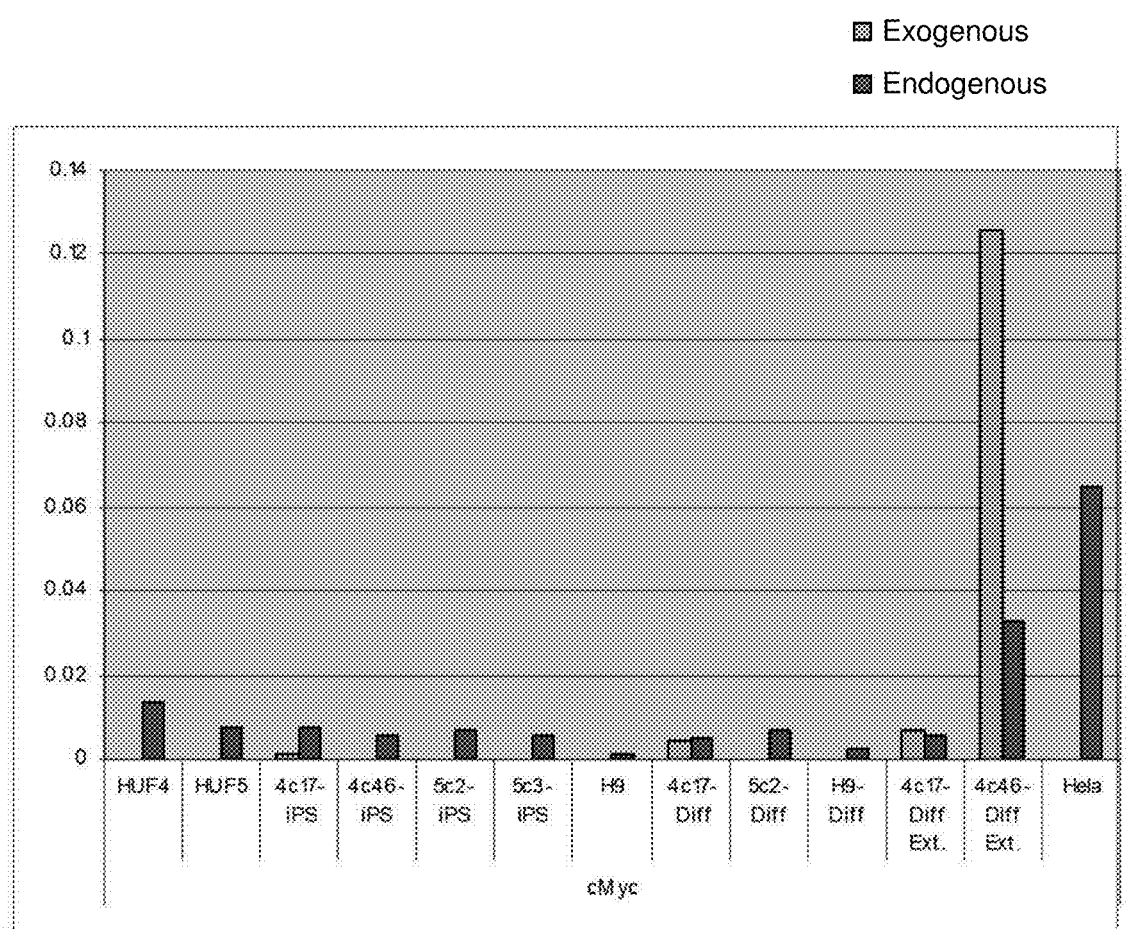

Teratoma sectioning was carried out, as an in vivo demonstration of the formation of the three germ layers, endoderm, mesoderm, and ectoderm. The results are presented in FIG. 16 for the HUF4 clone 17 line.

FIG. 17-21 illustrate qPCR expression of endogenous and exogenous transcription factors following reprogramming in HUF4 and HUF 5 lines (parental, iPSCs, differentiated) as well as control H9 and Hela cells. Endogenous and exogenous expression of Oct4, Sox2, cMyc, and Klf4 expression are examined. Primers used for the qPCR were as follows:
Primers for Exogenous Transcription Factor Expression Analysis:

```
pMXs-AS3200:
ttatcgtcgaccactgtgctgctg
(Used as Reverse primer for all exogenous
transcription factor analysis expression)

Oct4-Forward:
ccccagggccccattttggtacc

Sox2-Forward:
ggcacccctggcatggctcttggctc

Klf4-Forward:
acgatcgtggccccggaaaaggacc cMyc-Forward:
caacaaccgaaaatgcaccagcccag
```

Primers for Endogenous Transcription Factor Expression Analysis:

```
Oct4-Forward:
ccccagggccccattttggtacc

Oct4-Reverse:
cctagctcctccccctccccctgtc

Sox2-Forward:
ggcacccctggcatggctcttggctc

Sox2-Reverse:
cctcttttgcacccctcccatttccc

Klf4-Forward:
acgatcgtggccccggaaaaggacc

Klf4-Reverse:
tgattgtagtgctttctggctgggctcc cMyc-Foward:
ttgaggggcatcgtcgcgggaggctg cMyc-Reverse:
cgagaggacccccgtggatgcagag
```

Known techniques were used to differentiate the generated cell lines (from Example 2) into dopaminergic neuronal cells (FIG. 3, Methods in Example 1). Neural differentiation was carried out and neural induction parameters were examined. Further midbrain specification was then promoted by addition of specific factors.

Figures 22, 22A, 22B, 22C, 22D, 22E, 22F:
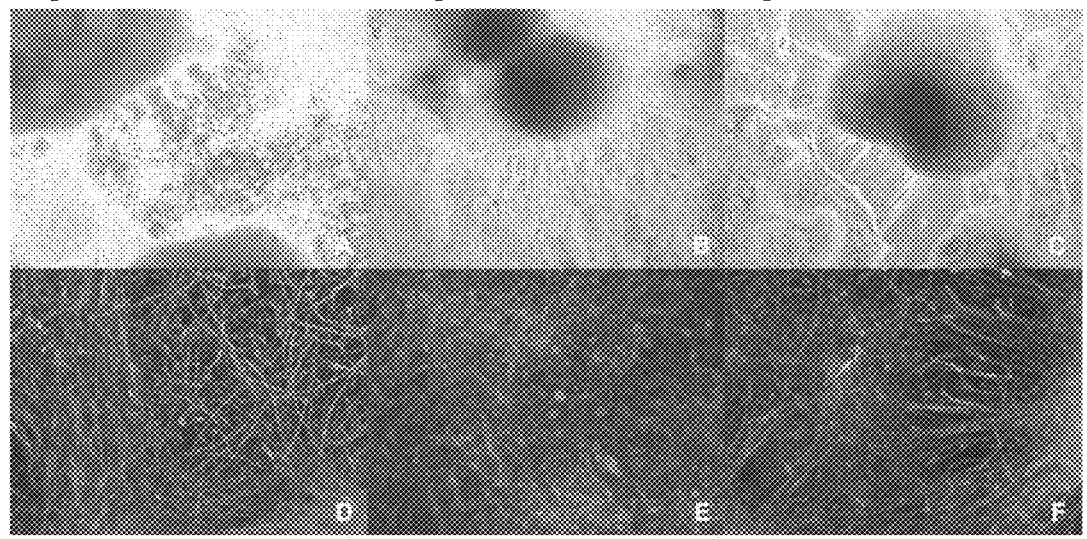
FIG. 22 illustrates neural induction at day 28 (phase contrast images) and day 50 (neural immunocytochemistry images for TH and NESTIN; H9 (FIG. 22A and FIG. 22D), HUF4 clone 17 (FIG. 22B and FIG. 22E) and HUF5 clone 2 (FIG. 22C and FIG. 22F). TH positive cells show the presence of dopaminergic neurons in culture, while lack of colocalization between TH and NESTIN indicate olfactory bulb neuron absence and midbrain dopaminergic neuron presence.

Markers of neural induction were examined at day 28 and day 50. TH, Nestin markers were visualized and analyzed. FIG. 22 shows the results and indicates midbrain dopaminergic neuron presence.

Figures 23, 23A, 23B, 23C, 23D, 23E, 23F:
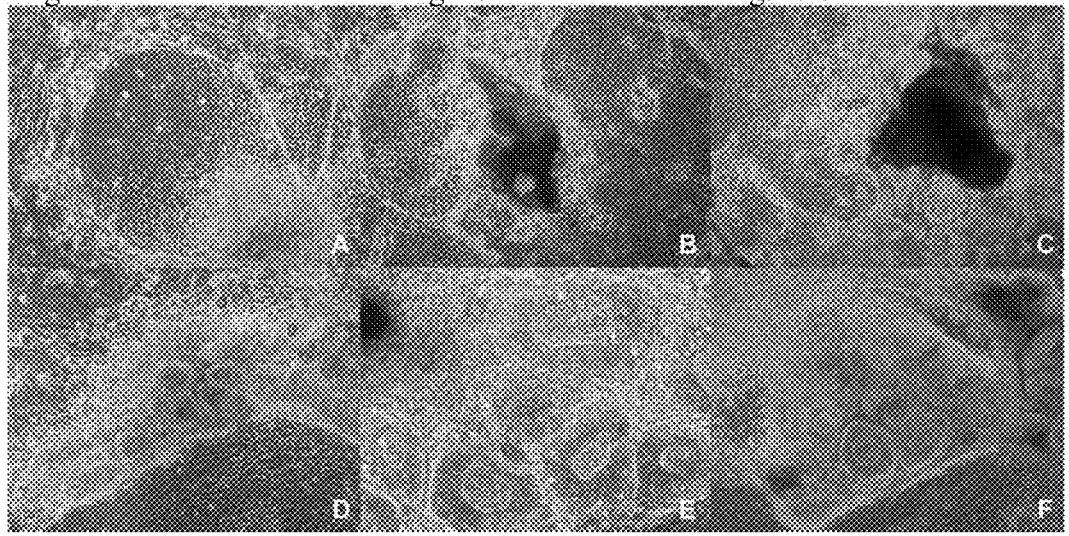
FIG. 23 illustrates HUF4 clone 17 neural induction time course phase contrast images 5× isolocation (FIGS. 23A-23F, except where noted): Days 3, 6, 9, 9 (left-inferior), 12 (left-inferior 10×), 14 (left-inferior). Formation of neural rosettes are visible begging on day 9 and continue to expand and proliferate through day 14 and beyond.
Figures 24, 24A, 24B, 24C, 24D, 24E, 24F:
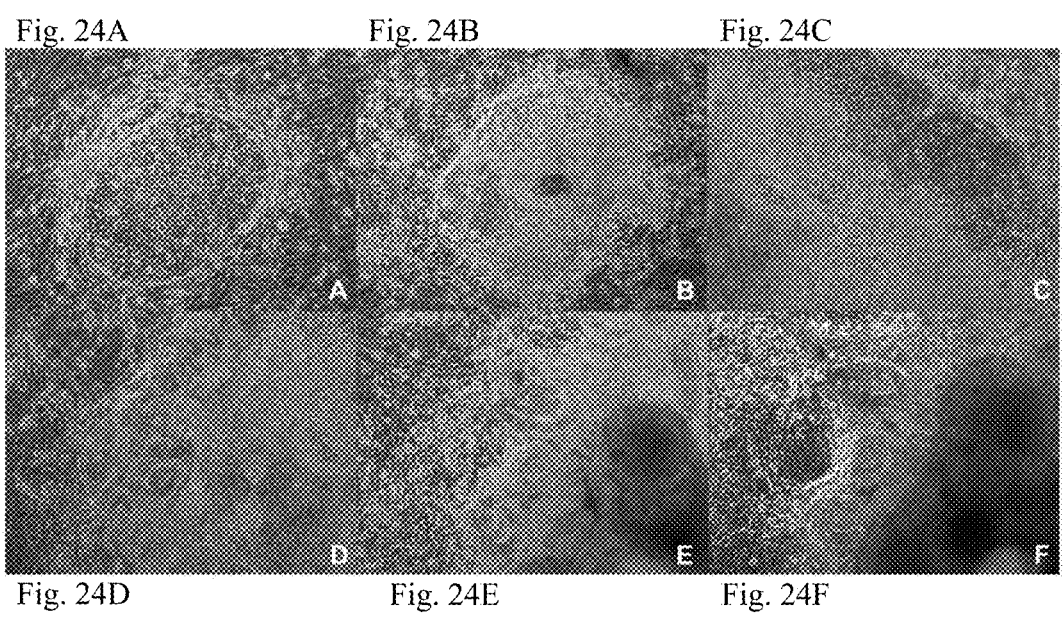
FIG. 24 illustrates HUF5 clone 2 neural induction time course phase contrast images 5× isolocation (FIGS. 24A-24F, except where noted): Days 3, 6, 9, 9 (left-inferior), 12 (left-inferior 10.times.), 14 (left-inferior).

FIGS. 23 and 24 show images of the time course of neural induction. Clover-like rosette patterns are visible in the HUF4 clone 17 line (FIG. 23) and HUF5 clone 2 line (FIG. 24).

Figure 25:
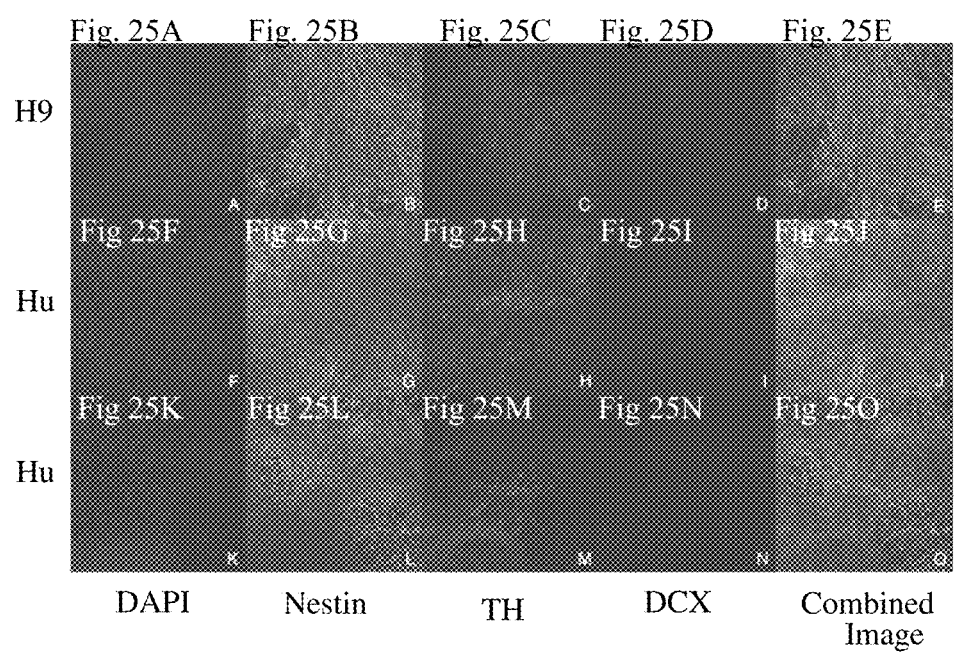
FIG. 25 illustrates somatic gene expression in H9 ESCs (FIGS. 25A-25E), and differentiated HUF4 (FIGS. 25F-25J) and HUF5 (FIGS. 25K-25O) iPSCs.

Expression of known neural fate markers were examined in the H9 ESCs, and the differentiated HUF4 and HUF5 lines, and are depicted in FIG. 25.

Figure 26:
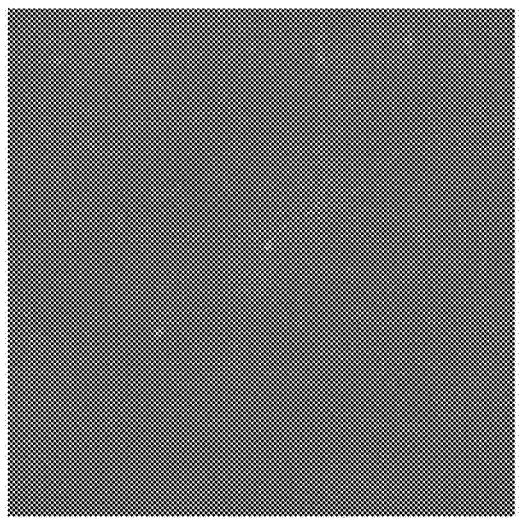
FIG. 26 illustrates α-synuclein staining of HUF4 cells.
Figure 26:
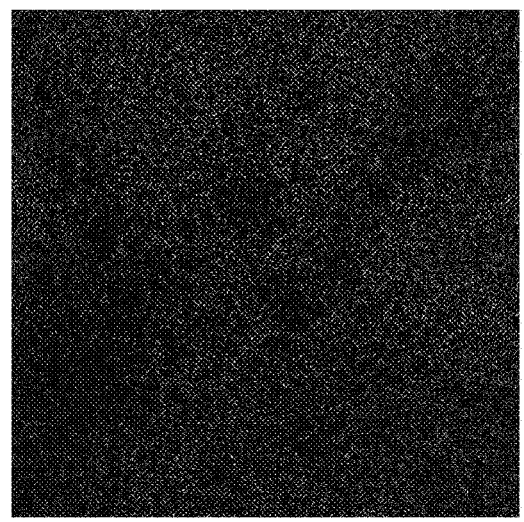

FIG. 26 illustrates α-synuclein staining of HUF4 cells.

A 96-gene panel of qPCR was run to compare the quantitative gene expression in H9 ESCs, HUF4 and HUF5 cell lines. The primer sets listed in Table 3 were purchased from Invitrogen and examined on parental fibroblast, iPSC, ESC, and dopaminergic differentiated cell lines. The experiment was performed to detect quantitative differences in classes of genes involved in ES cell function, neural progenitor function, dopamine neuron function, netrin receptor function, slit receptor function, ephrin receptor function, and pathological function.

TABLE 3

Taqman primers purchased from Invitrogen for analysis on 96-gene array

| | | | |
|---|---|---|---|
| Oct4 | Lmx1b | GAD2 | DNAJA1 |
| Klf4 | Msx1 | GAD1 | HSPB1 |
| SOX2 | Msx2 | SPON1 | robo4 |
| DNMT3B | Ngn2 | CALB1 | robo3 |
| c-Myc | Engrailed 1 | BDNF | robo2 |
| LIN28 | Engrailed 2 | SNCG | robo1 |
| TERT | ALDH1A1 | Nkx6.1 | MAOB |
| NANOG | NR4A2 | Chat | MAOA |
| GAPDH | B3GAT1 (beta III tubulin) | MNX1 (Hb9) | HMOX2 |
| CTNNB1 | Pitx3 | TPH2 | HMOX1 |
| EEF1A1 | TH | PNMT | CASP9 |
| CENTB3 (CENTRIN) | DDC | DBH | HSPA1A |
| Sox2 (TYPE2) | SLC6A3 | UCHL1 | GSTP1 |
| Gata6 | Pax2 | PARK7 | MT2A |
| Sox17 | Pax6 | PARK2 | MT1A |
| Pdx-1 | FoxA1 | SNCA | GPX1 |
| Brachyury | FoxA2 (Hnf-3b) | Olig2 | SOD2 |
| Gata-1 | SHH | GFAP | NOX1 |
| NCAM | NTN1 | DCC | ISL-1 |
| PRPH (Peripherin 1) | gdnf | NTN1 | FOXD3 |
| Nes | RET | HTRA2 | PROX1 |
| Sox1 | SLC18A2 | ATP13A2 | NKX2.1 |
| Otx2 | DRD2 | LRRK2 | NEFL (Neurofilament Light Protein) |
| Lmx1a | KCNJ6 | PINK1 | Map2 |

Example 4

Derivation, Characterization and Differentiation of Human iPSCs from a Parkinson's Disease Patient Carrying a Homozygous Mutation at the LRRK2 Locus iPSC lines were generated from human fibroblasts of a female patient (obtained by skin biopsy) with Parkinson's disease due to homozygous mutation at the LRRK2 locus (HUF6 line, Table 2) and her asymptomatic son (HUF7 line, Table 2), using a retroviral system with factors known to reprogram somatic cells, according to the methods of Example 1.

Figure 27:
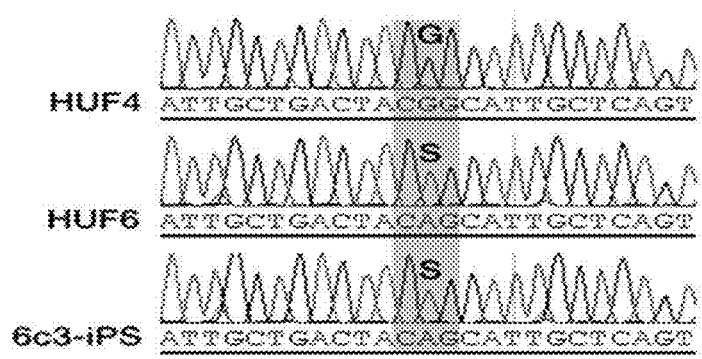
FIG. 27 illustrates the G2019S mutation in the HUF6, but not HUF4 lines.
Figure 28:
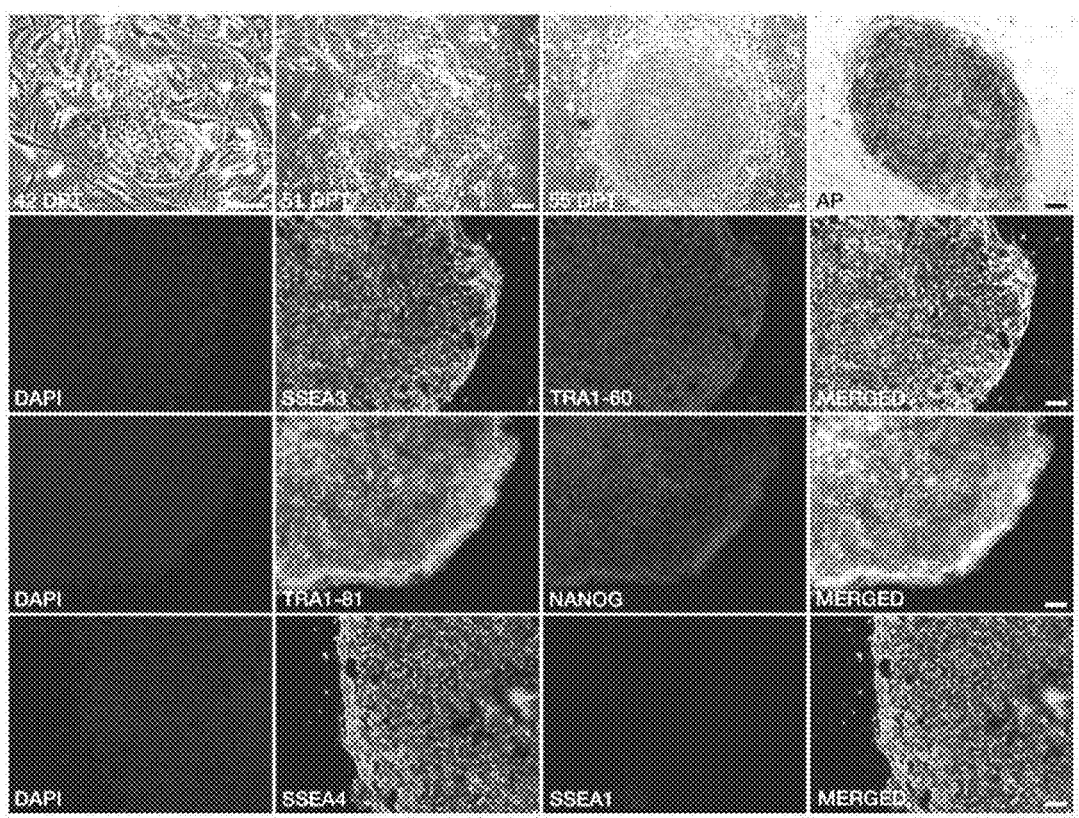
FIG. 28 illustrates the generation of the HUF6 iPSC line with 3 factors: Oct4, Sox2, and Klf4. The figure illustrates staining with pluripotency markers.

FIG. 27 shows the glycine to serine G2019S mutation in the HUF6 parental fibroblasts and the reprogrammed/dedifferentiated iPSC line HUF6 (clone 3), but not the HUF4 line. The HUF6 iPSC line was derived from the HUF6 parental fibroblasts and with the use of three factors: Oct4, Sox2, and KLF4. Staining for pluripotency markers are presented in FIG. 28.

Figure 29:
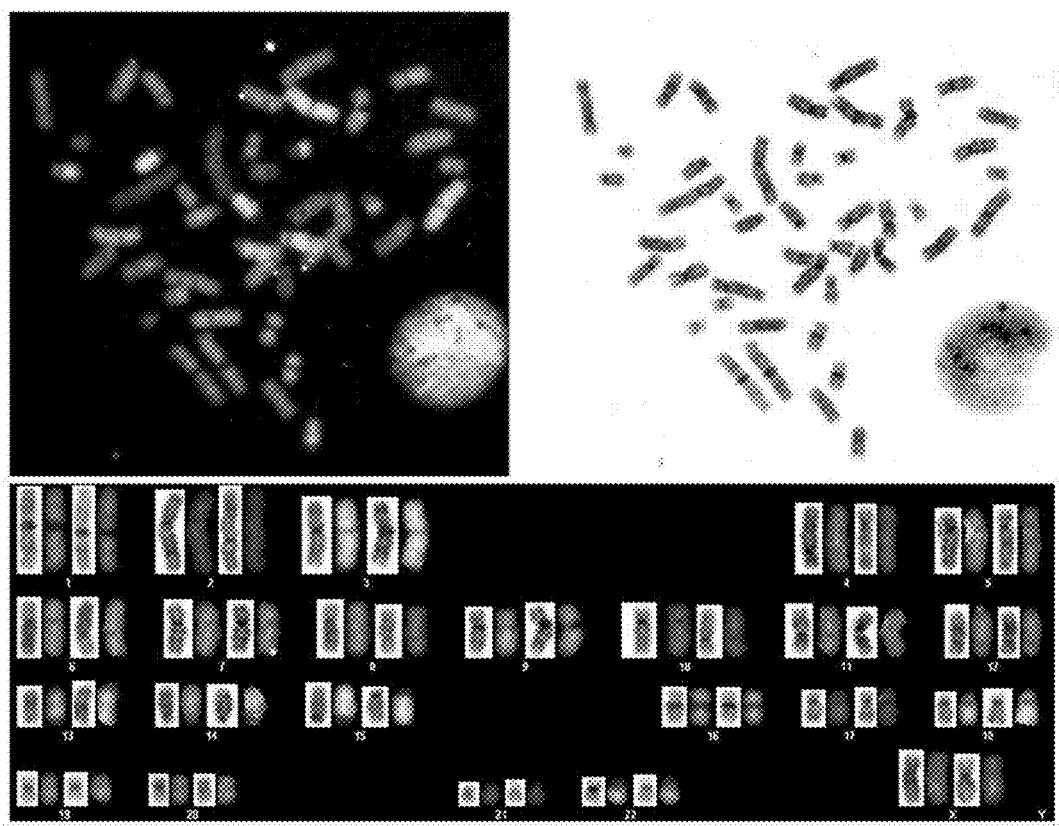
FIG. 29 illustrates the spectral karyotype analysis of the HUF6 iPSC line.

Karyotype analysis was carried out with the HUF6 iPSC line and is presented in FIG. 29. No gross chromosomal abnormalities were observed.

Figure 30:
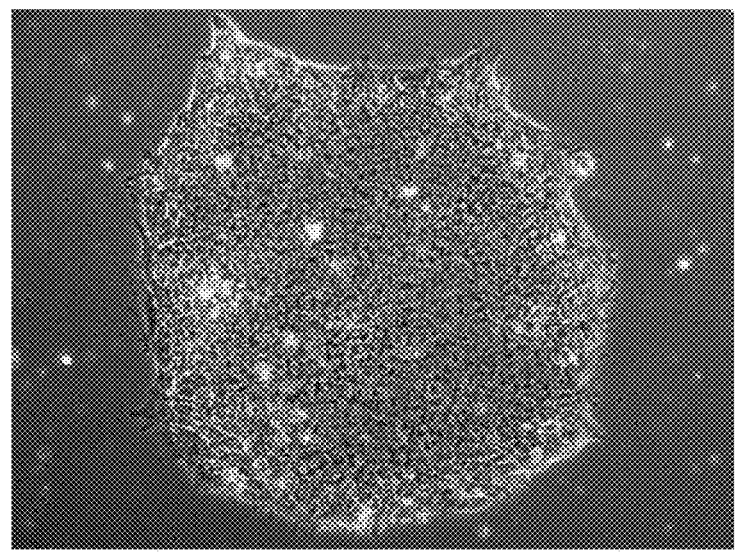
FIG. 30 shows growth and expansion of HUF6 iPS cells on matrigel and feeders.
Figure 30:
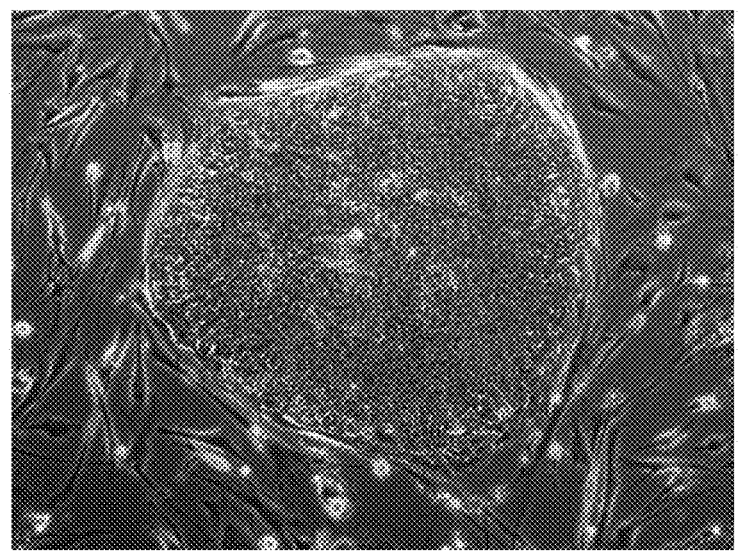

Growth on matrigel and feeders was examined and is presented in FIG. 30. The figure shows growth and expansion of HUF6 iPS cells on matrigel and feeders, indicative of stem cell-like morphology.

Figure 31:
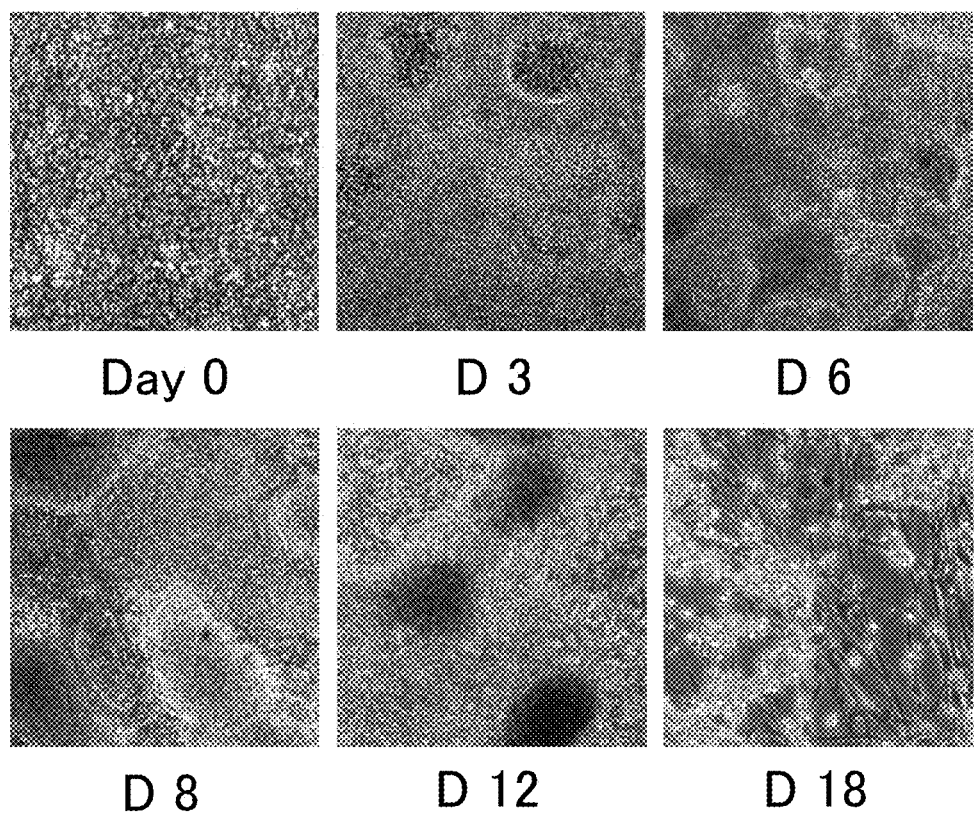
FIG. 31 illustrates differentiation of the HUF6 iPSCs to dopaminergic neurons using a 20-day protocol. The figure presents images of the cells during the time course of differentiation to dopaminergic neurons. D: day of differentiation.
Figure 32:
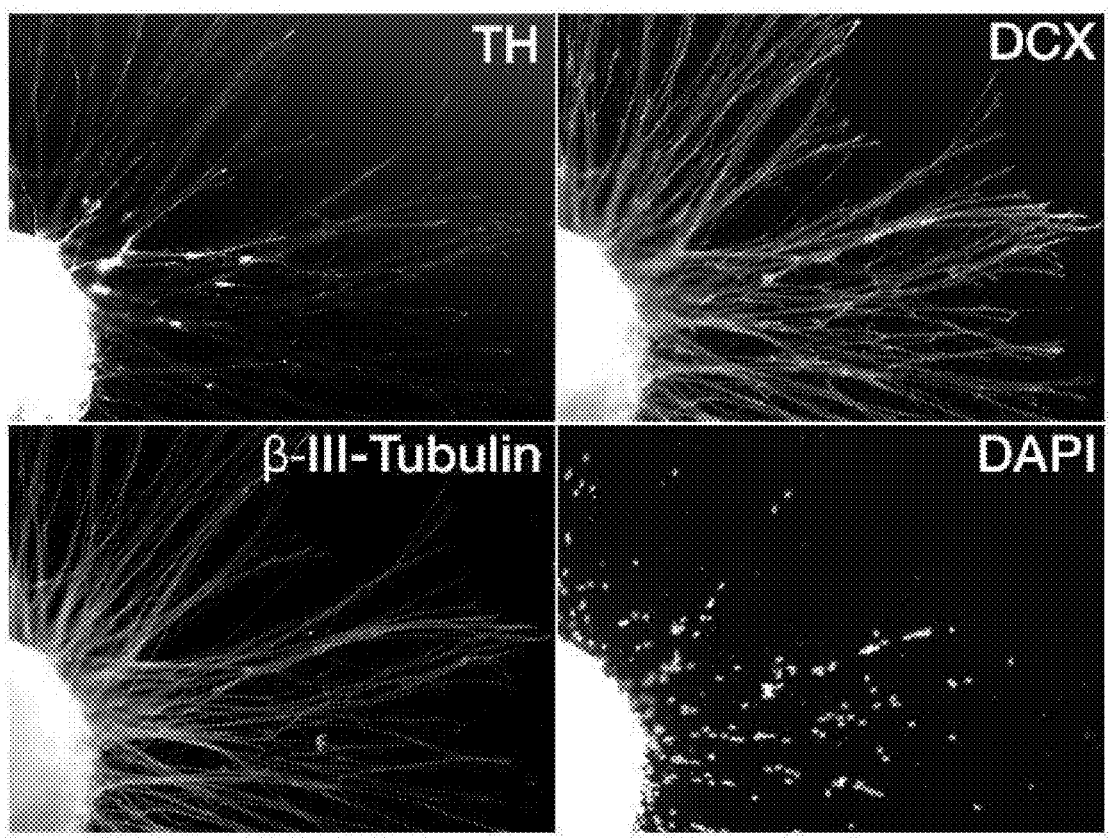
FIG. 32 illustrates the differentiation of HUF6-iPSCs into dopaminergic neurons after 20 days.

A 20-day protocol was carried out to differentiate the HUF6 line to dopaminergic neurons. The 20-day protocol is presented below. Cells were visualized along the time course of differentiation and are presented in FIG. 31. Between Day 1 and Day 5 of the differentiation protocol, Noggin was expressed and the small molecule SB431542 was applied in SRM media. Between Day 5 and Day 9 of the differentiation protocol Sonic hedgehog was expressed in N2 media. Between Day 9 and Day 12, BDNF, AA, SHH, and FGF8b were expressed in N2 media. Between Day 12 and Day 20, BDNF, AA, GDNF, TGF-13, and cAMP were expressed in N2 media. (protocol in Chambers et al. 2009). FIG. 32 depicts the differentiation of HUF6-iPSCs into dopaminergic neurons after 20 days.

Example 5

Figure 33:
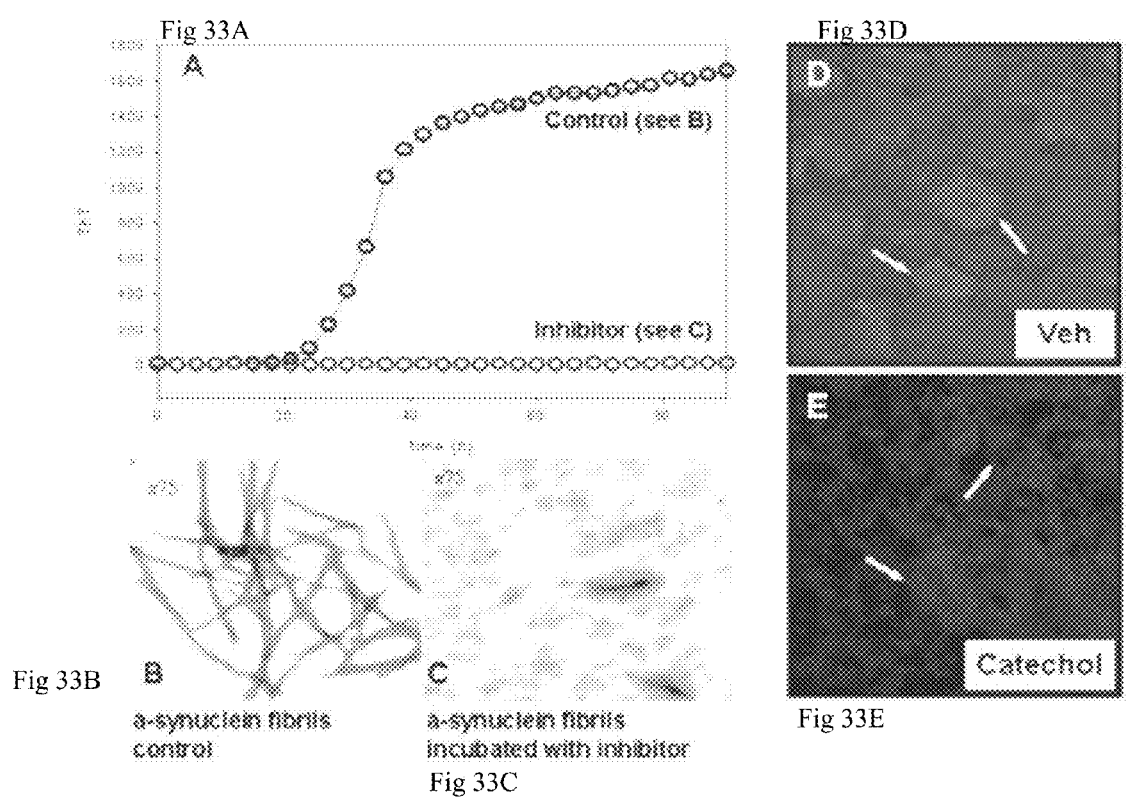
FIG. 33 illustrates that specific agents can be used to block or reverse pathological phenotypes such as .alpha.-synuclein aggregation. The figure shows in vitro and ex vivo methods for rapid screening of anti-aggregation compounds.

Non-Viral Derivation of Human iPSCs from a Parkinson's Disease Patient Carrying a Homozygous Mutation at the LRRK2 Locus iPSC lines are generated from human fibroblasts of a female patient (obtained by skin biopsy) with Parkinson's disease due to homozygous mutation at the LRRK2 locus using a non-viral system with factors known to reprogram somatic cells, according to the methods of Example 1. This non-viral system is free of viral reprogramming/dedifferentiating factors. Fibroblasts are reprogrammed and differentiated into dopaminergic neurons. Making the iPSCs free of viral reprogramming factors involves use of cre-recombinase excisable viruses. The cells are then differentiated into brainstem nuclei, olfactory neurons, dopaminergic neurons and cholinergic neurons and the lines are maintained. If any of the differentiated cell lines display spontaneous formation of α-synuclein mediated aggregation, the lines are used as a tool for screening candidate agents (such as those in Table 1) for their ability to dis-aggregate or prevent aggregation of α-synuclein. Such cells lines can be used as a tool for screening candidate agents (such as those in Table 1) for their ability to dis-aggregate or prevent aggregation of α-synuclein. As shown in FIG. 33, in vitro and ex vivo methods for rapid screening of anti-aggregation compounds are used for the screening. FIG. 33 shows: (A) Inhibition of fibrillation of α-synuclein upon incubation with a specific inhibitor, detected by Thioflavin T fluorescein and (B-C) confirmed by electron microscopy of α-synuclein fibrils. (D-E) Diminished Thioflavin S deposits (which label aggregate protein) detected in paraquat-treated mouse brain with Catechol (250 uM), indicative of treatment-induced dissolution of aggregate structure.

While embodiments of the present methods have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the claimed methods. It is intended that the following claims define the scope of the invention and that methods and structures within the scope of these claims and their equivalents be covered thereby.

What is claimed is:

1. A method of producing a differentiated dopaminergic cell line, the method comprising:
   a) producing induced pluripotent stem cells (iPSCs) from somatic cells harvested from a subject diagnosed with a neurodegenerative disease, wherein the somatic cells carry a genetic variation that is associated with the disease; and
   b) differentiating the iPSCs towards a dopaminergic cell type, wherein the dopaminergic cell type is associated with the neurodegenerative disease and displays a phenotype of cellular protein aggregation, thereby resulting in the differentiated dopaminergic cell line.

2. The method of claim 1, wherein the somatic cells are fibroblasts.

3. The method of claim 1, wherein the genetic variation is a copy number variation.

4. The method of claim 3, wherein the genetic variation is a triplication.

5. The method of claim 1, wherein the genetic variation is a deletion, an insertion, a complex multi-state variant, a substitution, a transition, a transversion, or a duplication, of one or more nucleotides in a gene that is associated with the disease.

6. The method of claim 1, wherein the neurodegenerative disease is Parkinson's disease, Alzheimer's disease, diffuse Lewy body disease or any other Lewy body disorder or synucleinopathy, corticobasal degeneration, multiple system atrophy, progressive supranuclear palsy, frontotemporal dementia with Parkinsonism chromosome 17, Huntington's disease, spinocerebellar ataxias, amytropic lateral sclerosis, or Creutzfeld Jakob disease.

7. The method of claim 1, wherein the neurodegenerative disease is Parkinson's disease or Parkinson's-like disease.

8. The method of claim 7, wherein the genetic variation is in a gene selected from PARK1 (SNCA or α-synuclein), PARK2 (Parkin), PARK5 (UCHL1), PARK6 (PINK1), PARK7 (DJ-1), PARK8 (LRRK2), and PARK 11 (GIGFY2).

9. The method of claim 8, wherein the gene is PARK1 (SNCA or α-synuclein).

10. The method of claim 8, wherein the gene is PARK8 (LRRK2).

11. The method of claim 9 wherein the variation is triplication of the SNCA gene.

12. The method of claim 10, wherein the genetic variation comprises a G2019S mutation.

13. The method of claim 1, wherein the iPSCs are differentiated towards a midbrain dopaminergic cell type.

14. The method of claim 1, wherein the iPSCs are differentiated to adopt the cell type within 20 days.

15. The method of claim 1, wherein the iPSCs are produced without the use of a retrovirus or a lentivirus.

16. The method of claim 1, wherein the iPSCs are produced with a method comprising the use of three factors.

17. The method of claim 16, wherein the three factors are OCT4, SOX2, and KLF4.

18. The method of claim 1, wherein the differentiated dopaminergic cell line further displays a phenotype of cell viability, inclusion bodies, dystrophic neurites, apoptosis, necrosis, oxidative stress, mitochondrial dysfunction, or α-synuclein aggregation.

19. The method of claim 1, wherein the phenotype changes when the differentiated dopaminergic cell line is in contact with a putative therapeutic agent.

20. The method of claim 1, wherein the dopaminergic cell type is a cell type that is affected in the natural progression of the neurodegenerative disease.

21. A method of screening a putative therapeutic agent for usefulness in the treatment of a neurodegenerative disease, the method comprising:
   a) producing a differentiated dopaminergic cell line by the method of claim 1;
   b) contacting the dopaminergic cell line with an agent;
   c) detecting a response to the agent in the dopaminergic cell line; and
   d) determining whether the agent is useful in the treatment based on the detected response.

* * * * *

SEQUENCE LISTING

<160> NUMBER OF SEQ ID NOS: 17

<210> SEQ ID NO 1

-continued

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgacaaatgt tggaggagca                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctgggctact gctgtcacac                                                  20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgggctacac tgagcaccag                                                  20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gggtgtcgct gttgaagtca                                                  20

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttatcgtcga ccactgtgct gctg                                             24

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccccagggcc ccattttggt acc                                              23

<210> SEQ ID NO 7
<211> LENGTH: 26
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggcacccctg gcatggctct tggctc                                        26

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
acgatcgtgg ccccggaaaa ggacc                                         25

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caacaaccga aaatgcacca gccccag                                       27

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cctagctcct cccctccccc tgtc                                          24

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cctcttttgc acccctccca tttccc                                        26

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgattgtagt gctttctggc tgggctcc                                      28

<210> SEQ ID NO 13
<211> LENGTH: 26
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 13
ttgaggggca tcgtcgcggg aggctg                                          26

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgagaggacc ccgtggatgc agag                                            24

<210> SEQ ID NO 15
<211> LENGTH: 25
<212> TYPE: DNA
<213> ORGANISM: Homo sapiens

<400> SEQUENCE: 15
attgctgact acggcattgc tcagt                                           25

<210> SEQ ID NO 16
<211> LENGTH: 25
<212> TYPE: DNA
<213> ORGANISM: Homo sapiens

<400> SEQUENCE: 16
attgctgact acagcattgc tcagt                                           25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
attgctgact acagcattgc tcagt                                           25
```